United States Patent
Bellet et al.

(10) Patent No.: US 12,144,811 B2
(45) Date of Patent: Nov. 19, 2024

(54) COMBINATION OF A 4-PYRIMIDINESULFAMIDE DERIVATIVE WITH AN SGLT-2 INHIBITOR FOR THE TREATMENT OF ENDOTHELIN RELATED DISEASES

(71) Applicant: IDORSIA PHARMACEUTICALS LTD, Allschwil (CH)

(72) Inventors: Marc Bellet, Allschwil (CH); Marc Iglarz, Allschwil (CH); Martin Bolli, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

(21) Appl. No.: 16/768,604

(22) PCT Filed: Nov. 29, 2018

(86) PCT No.: PCT/EP2018/082947
§ 371 (c)(1),
(2) Date: May 29, 2020

(87) PCT Pub. No.: WO2019/106066
PCT Pub. Date: Jun. 6, 2019

(65) Prior Publication Data
US 2021/0169881 A1 Jun. 10, 2021

(30) Foreign Application Priority Data
Nov. 30, 2017 (WO) .................. PCT/EP2017/081050

(51) Int. Cl.
*A61K 31/506* (2006.01)
*A61K 9/00* (2006.01)
(Continued)

(52) U.S. Cl.
CPC .......... *A61K 31/506* (2013.01); *A61K 9/0053* (2013.01); *A61K 9/2018* (2013.01);
(Continued)

(58) Field of Classification Search
CPC .. A61K 31/506; A61K 9/0053; A61K 9/2018; A61K 9/2054; A61K 31/7004;
(Continued)

(56) References Cited

U.S. PATENT DOCUMENTS 5,612,359 A   3/1997  Murugesan
6,043,265 A   3/2000  Murugesan et al.
(Continued)

FOREIGN PATENT DOCUMENTS

AU   2005225511 B2   1/2009
AU   2005225511 C1   4/2023
(Continued)

OTHER PUBLICATIONS

Demir et al., New strategies to tackle diabetic kidney disease, Current Opinion in Nephrology and Hypertension, vol. 25, No. 4, 348-354, Jul. 2016 (Year: 2016).*
(Continued)

*Primary Examiner* — Kortney L. Klinkel
*Assistant Examiner* — Padmaja S Rao
(74) *Attorney, Agent, or Firm* — Hoxie & Associates LLC

(57) ABSTRACT

The present invention concerns the compound aprocitentan, {5-(4-bromo-phenyl)-6-[2-(5-bromo-pyrimidin-2-yloxy)-ethoxy]-pyrimidin-4-yl}-sulfamide:
(Continued)

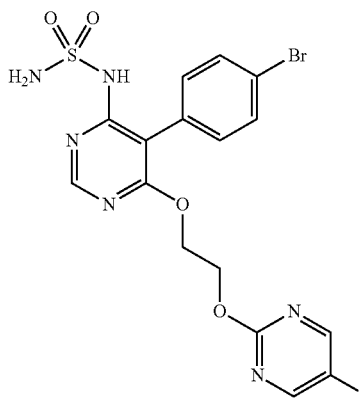

and its use as endothelin receptor antagonist, in combination with an SGLT-2 inhibitor. The invention further relates to pharmaceutical compositions comprising aprocitentan in combination with said SGLT-2 inhibitor. The invention further relates to such pharmaceutical compositions comprising crystalline forms of aprocitentan.

31 Claims, 9 Drawing Sheets

(51) Int. Cl.
  *A61K 9/20* (2006.01)
  *A61K 31/7004* (2006.01)
  *A61K 31/7048* (2006.01)
  *A61P 3/10* (2006.01)
  *A61P 7/00* (2006.01)
  *A61P 13/12* (2006.01)
(52) U.S. Cl.
  CPC ........ *A61K 9/2054* (2013.01); *A61K 31/7004* (2013.01); *A61K 31/7048* (2013.01); *A61P 3/10* (2018.01); *A61P 7/00* (2018.01); *A61P 13/12* (2018.01)
(58) Field of Classification Search
  CPC ................ A61K 31/7048; A61K 31/70; A61K 31/7042; A61K 31/7056; A61K 2300/00; A61P 3/10; A61P 7/00; A61P 13/12; A61P 9/10; A61P 9/12; A61P 17/02
  See application file for complete search history.

(56) References Cited

U.S. PATENT DOCUMENTS

| | | |
|---|---|---|
| 7,521,430 B2 | 4/2009 | Nomura et al. |
| 7,732,596 B2 | 6/2010 | Fushimi et al. |
| 7,943,582 B2 | 5/2011 | Nomura et al. |
| 7,943,788 B2 | 5/2011 | Nomura et al. |
| 7,989,424 B2 | 8/2011 | Fujikura et al. |
| 8,080,580 B2 | 12/2011 | Mascitti et al. |
| 8,101,599 B2 | 1/2012 | Shetty et al. |
| 8,202,984 B2 | 6/2012 | Nomura et al. |
| 8,222,219 B2 | 7/2012 | Nomura et al. |
| 8,324,232 B2 | 12/2012 | Bolli et al. |
| 8,475,839 B2 | 7/2013 | Cao et al. |
| 8,513,202 B2 | 8/2013 | Nomura et al. |
| 8,685,934 B2 | 4/2014 | Strumph et al. |
| 9,938,244 B2 | 4/2018 | Abele et al. |
| 10,919,881 B2 | 2/2021 | Bolli et al. |
| 11,174,247 B2 | 11/2021 | Bellet et al. |
| 11,680,058 B2 | 6/2023 | Bolli et al. |
| 11,787,782 B2 | 10/2023 | Bellet et al. |
| 2005/0209166 A1 | 9/2005 | Eckhardt et al. |
| 2012/0071403 A1* | 3/2012 | Strumph .................. A61P 3/10 514/23 |
| 2012/0142716 A1 | 6/2012 | Bolli et al. |
| 2016/0368882 A1 | 12/2016 | Abele et al. |
| 2017/0145000 A1 | 5/2017 | Sheng et al. |
| 2020/0002317 A1 | 1/2020 | Bolli et al. |
| 2020/0061061 A1 | 2/2020 | Bellet et al. |
| 2021/0206750 A1 | 7/2021 | Bolli et al. |
| 2022/0064149 A1 | 3/2022 | Bellet et al. |
| 2023/0391757 A1 | 12/2023 | Bolli et al. |

FOREIGN PATENT DOCUMENTS

| | | |
|---|---|---|
| EP | 1 364 958 | 11/2003 |
| EP | 1 651 658 B1 | 1/2013 |
| EP | 1 654 269 B1 | 10/2014 |
| WO | WO 02/053557 | 7/2002 |
| WO | WO 03/097045 | 11/2003 |
| WO | WO 2005/012321 A1 | 2/2005 |
| WO | WO 2005/012326 A1 | 2/2005 |
| WO | WO 2005/092877 A1 | 10/2005 |
| WO | WO 2007/098390 | 8/2007 |
| WO | WO 2007/146900 | 12/2007 |
| WO | WO 2009/024906 | 2/2009 |
| WO | WO 2010/138535 A1 | 12/2010 |
| WO | WO 2014/161918 | 10/2014 |
| WO | WO 2015/116880 A1 | 8/2015 |
| WO | WO 2015/121397 | 8/2015 |
| WO | WO 2015/173584 A1 | 11/2015 |
| WO | WO 2016/073846 | 5/2016 |
| WO | WO 2016/073846 A1 | 5/2016 |
| WO | WO 2017/064679 A1 | 4/2017 |
| WO | WO 2018/153513 | 8/2018 |
| WO | WO 2018/154101 | 8/2018 |

OTHER PUBLICATIONS

Heerspink, H. et al., "Atrasentan and Renal Events in Patients with Type 2 Diabetes and Chronic Kidney Disease (SONAR): A Double-blind, Randomised, Placebo-Controlled Trial," Lancet, 2019, 393, 1937-1947.
Heerspink, H. et al., "New Insights from SONAR Indicate Adding Sodium Glucose Co-transporter 2 Inhibitors to an Endothelin Receptor Antagonist Mitigates Fluid Retention and Enhances Albuminuria Reduction," Kidney International, 2021, 99, 346-349.
Trensz, F. et al., "Pharmacological Characterization of Aprocitentan, a Dual Endothelin Receptor Antagonist, Alone and in Combination with Blockers of the Renin Angiotensin System, in Two Models of Experimental Hypertension," The Journal of Pharmacology and Experimental Therapeutics, 2019, 368, 462-473 and supplemental information.
Verweij, P. et al., "Randomized Dose-Response Study of the New Dual Endothelin Receptor Antagonist Aprocitentan in Hypertension," Hypertension, 2020, 75, doi: 10.1161/hypertensionaha.119. 14504, online data supplement, 10 pages.
Wheeler, D. et al., "The Dapagliflozin and Prevention of Adverse Outcomes in Chronic Kidney Disease (DAPA-CKD) Trial: Baseline Characteristics," Nephrology Dialysis Transplantation, 2020, 35, 1700-1711.
5.11. Characters section in monographs, *European Pharmacopoeia 8.0*, pp. 695.
"Actelion provides an update on the progress towards launching Idorsia—Key results for pipeline assets to be developed by Idorsia," Actelion—Media Release, pp. 1-7 (2017).
"Actelion's Cardiovascular Pipeline Investor Webcast," Actelion, pp. 1-52 (2016).
"Actelion Ltd Cardiovascular Pipeline Update Corporate Call," *Thomson Reuters—Final Transcript*, pp. 1-17 (2016).
Atanur et al., "The genome sequence of the spontaneously hypertensive rat: Analysis and functional significance," *Genome Research*, 20:791-803 (2010).

(56) References Cited

OTHER PUBLICATIONS

Aversa et al., "Comparative Safety and Tolerability of Endothelin Receptor Antagonists in Pulmonary Arterial Hypertension," *Drug Saf*, 17 pages (2015).
Baltatu et al., "Avosentan is protective in hypertensive nephropathy at doses notcausing fluid retention," *Pharmacological Research*, pp. 1-5 (2013).
Bolli et al., "The Discovery of N-[5-(4-Bromophenyl)-6-[2-[(5-bromo-2-pyrimidinyl)oxy]ethoxy]-4-pyrimidinyl]-N'-propylsulfamide (Macitentan), an Orally Active, Potent Dual Endothelin Receptor Antagonist," *J. Med. Chem.*, 55:7849-7861 (2012).
Bolli "The Discovery of Macitentan—A Standard Medicinal Chemistry Program?" *CHIMIA*, 71:420-429 (2017).
Boss et al., "From bosentan (Tracleer®) to macitentan (Opsumit®): The medicinal chemistry perspective," *Bioorganic & Medicinal Chemistry Letters*, 26:3381-3394 (2016).
Bruderer et al., "Absorption, distribution, metabolism, and excretion of macitentan, a dual endothelin receptor antagonist, in humans," *Xenobiotica*, pp. 1-10 (2012).
Burnier, "Update on Endothelin Receptor Antagonists in Hypertension," *Current Hypertension Reports*, 20(51), pp. 1-7 (2018).
Chow et al., "Quarter-dose quadruple combination therapy for initial treatment of hypertension: placebo-controlled, crossover, randomised trial and systematic review," *Lancet*, 389:1035-42 (2017).
Davenport et al., "Endothelin," *Pharmacol Rev*, 68:357-418 (2016).
De Kanter et al., "Physiologically-Based Pharmacokinetic Modeling of Macitentan: Prediction of Drug-Drug Interactions," *Clin Pharmacokinet*, 12 pages (2015).
Demir et al., "New strategies to tackle diabetic kidney disease," *Curr Opin Nephrol Hypertens*, 25(4):348-354 (2016).
Denolle et al., "Management of resistant hypertension: expert consensus statement from the French Society of Hypertension, an affiliate of the French Society of Cardiology," *Journal of Human Hypertension*, 30:657-663 (2016).
Egido et al., "Atrasentan for the treatment of diabetic Nephropathy," *Expert Opinion on Investigational Drugs*, 22 pages (2017).
Eirin et al., "Emerging concepts for patients with treatment-resistant hypertension," *Trends in Cardiovascular Medicine*, pp. 1-7 (2016).
EMA/527460/2013; EMEA/H/C/001068 "Exforge HCT: amlodipine / valsartan / hydrochlorothiazide," *EPAR summary for the public—European Medicines Agency*, 3 pages (2013).
Feld et al., "Renal lesions and proteinuria in the spontaneously hypertensive rat made normotensive by treatment," *Kidney International*, 20:606-614 (1981).
Fox et al., "Optimising hypertension treatment: NICE/BHS guideline implementation and audit for best practice," *The British Journal of Cardiology*, 20(Supp. 1), 16 pages (2013).
Galie et al., "SERAPHIN haemodynamic substudy: the effect of the dual endothelin receptor antagonist macitentan on haemodynamic parameters and NT-proBNP levels and their association with disease progression in patients with pulmonary arterial hypertension," *European Heart Journal*, 38:1147-1155 (2017).
Gavras et al., "Malignant Hypertension Resulting from Deoxycorticosterone Acetate and Salt Excess," *Circulation Research*, 36:300-309 (1975).
Goddard et al., "Endothelin A Receptor Antagonism and Angiotensin-Converting Enzyme Inhibition Are Synergistic via an Endothelin B Receptor-Mediated and Nitric Oxide-Dependent Mechanism," *J Am Soc Nephrol*, 15:2601-2610 (2004).
Gradman et al., "Combination therapy in hypertension," *Journal of the American Society of Hypertension*, 4(1):42-50 (2010).
Griesser, "Chapter 8—The Importance of Solvates," Polymorphism in the Pharmaceutical Industry, 211-233; pp. 1-19 (2006).
Heerspink et al., "Sodium Glucose Cotransporter 2 Inhibitors in the Treatment of Diabetes Mellitus, Cardiovascular and Kidney Effects, Potential Mechanisms, and Clinical Applications," *Circulation*, 134:752-772 (2016).
Heerspink, et al., "Baseline characteristics and enrichment results from the SONAR trial," *Diabetes Obes Metab.*, 20:1829-1835 (2018).
Heerspink et al., "Rationale and protocol of the Study Of diabetic Nephropathy with AtRasentan (SONAR) trial: A clinical trial design novel to diabetic nephropathy," *Diabetes Obes Metab.*, 20:1369-1376 (2018).
Hunter et al., "First-in-Man Demonstration of Direct Endothelin-Mediated Natriuresis and Diuresis," *Hypertension*, 1-9 (2017).
Iglarz et al., "Pharmacology of Macitentan, an Orally Active Tissue-Targeting Dual Endothelin Receptor Antagonist," *The Journal of Pharmacology and Experimental Therapeutics*, 327(3):736-745 (2008).
Iglarz et al., "Vascular Effects of Endothelin Receptor Antagonists Depends on Their Selectivity for ETA Versus ETB Receptors and on the Functionality of Endothelial ETB Receptors," *J Cardiovasc Pharmacol*, 66(4):332-337 (2015).
Iglarz et al., "Comparison of pharmacological activity of macitentan and bosentan in preclinical models of systemic and pulmonary hypertension," *Life Sciences*, 118:333-339 (2014).
Janiak et al., "Long-term blockade of angiotensin AT1 receptors increases survival of obese Zucker rats," *European Journal of Pharmacology*, 534:271-279 (2006).
Kim et al., "Pharmacologic Management for Heart Failure and Emerging Therapies," *Curr Cardiol Rep*, 19:94; pp. 1-6 (2017).
Kohan et al., "Predictors of Atrasentan-Associated Fluid Retention and Change in Albuminuria in Patients with Diabetic Nephropathy," *Clin J Am Soc Nephrol*, 10:1568-1574 (2015).
Kohan et al., "Endothelin antagonists for diabetic and non-diabetic chronic kidney disease," *British Journal of Clinical Pharmacology*, 76(4):573-579 (2012).
Laffin et al., "Endothelin Antagonism and Hypertension: An Evolving Target," *Seminars in Nephrology*, 35(2):168-175 (2015).
Lepist et al., "Evaluation of the Endothelin Receptor Antagonists Ambrisentan, Bosentan, Macitentan, and Sitaxsentan as Hepatobiliary Transporter Inhibitors and Substrates in Sandwich-Cultured Human Hepatocytes," *PLOS One*, 9(1) e87548; pp. 1-10 (2014).
Maguire et al., "Endothelin Receptors and Their Antagonists," *Seminars in Nephrology*, 35(2):125-136 (2015).
Mann et al., "Avosentan for Overt Diabetic Nephropathy," *J Am Soc Nephrol.*, 21(3):527-535; pp. 1-19 (2010).
Mancia et al., "2013 ESH/ESC Guidelines for the management of arterial hypertension—The Task Force for the management of arterial hypertension of the European Society of Hypertension (ESH) and of the European Society of Cardiology (ESC)," ESH and ESC Guidelines, *Journal of Hypertension*, 31:1281-1357 (2013).
Martens et al., "Promise of SGLT2 Inhibitors in Heart Failure: Diabetes and Beyond," *Curr Treat Options Cardio Med*, 19:23; pp. 1-14 (2017).
Nielsen et al., "Dual Endothelin Receptor Blockade Abrogates Right Ventricular Remodeling and Biventricular Fibrosis in Isolated Elevated Right Ventricular Afterload," *PLOS One*, 11(1): e0146767, pp. 1-18 (2016).
Palmer et al., "Comparative efficacy and safety of blood pressure-lowering agents in adults with diabetes and kidney disease: a network meta-analysis," *Lancet*, 385: 2047-56 (2015).
Pinto et al., "Lessons from rat models of hypertension: from Goldblatt to genetic Engineering," *Cardiovascular Research*, 39:77-88 (1998).
Potenza et al., "Insulin resistance in spontaneously hypertensive rats is associated with endothelial dysfunction characterized by imbalance between NO and ET-1 production," *Am J Physiol Heart Circ Physiol*, 289:H813-H822 (2005).
Rabelink et al., "Endothelin Receptor Blockade in Patients with Diabetic Nephropathy," *Contrib Nephrol.*, 172:235-242 (2011).
Rapp et al., "Dahl Salt-Susceptible and Salt-Resistant Rats," *Hypertension*, 4:753-763 (1982).
Remington, "Part 5—Pharmaceutical Manufacturing," *The Science and Practice of Pharmacy*, 21$^{st}$ Edition, 5 pages (2005).
Saleh et al., "Distinct Actions of Endothelin A-Selective Versus Combined Endothelin A/B Receptor Antagonists in Early Diabetic Kidney Disease," *JPET*, 338(1):263-270 (2011).
Sen et al., "Renal, retinal and cardiac changes in type 2 diabetes are attenuated by macitentan, a dual endothelin receptor antagonist," *Life Sciences*, pp. 1-11,(2012).

(56) References Cited

OTHER PUBLICATIONS

Sharma et al., "Did all thiazides take undue credit of good work of chlorthalidone?" *Indian J Pharmacol.*, 48(5):479-480; 3 pages (2016).
Sidharta et al., "Clinical Pharmacokinetics and Pharmacodynamics of the Endothelin Receptor Antagonist Macitentan," *Clin Pharmacokinet*, 54:457-471 (2015).
Sidharta et al., "Single-And Multiple-Dose Safety, Pharmacokinetics, and Pharmacodynamics of the Dual Endothelin Receptor Antagonist Aprocitentan in Healthy Adult and Elderly Subjects," PII-121— *Abstracts, Clinical Pharmacology & Therapeutics*, 103(Supp. S1) 1 page (2018).
Sidharta et al., "Pharmacokinetics of the Novel Dual Endothelin Receptor Antagonist Macitentan in Subjects with Hepatic or Renal Impairment," *The Journal of Clinical Pharmacology*, 54(3) 291-300 (2013).
Sidharta et al., "Macitentan: entry-into-humans study with a new endothelin receptor antagonist," *Eur J Clin Pharmacol*, pp. 1-8 (2011).
Sloop et al., "The role of chronic hyperviscosity in vascular disease," *Ther Adv Cardiovasc Dis.*, 9(1):19-25 (2015).
Su et al., "Longitudinal Changes in Measured Glomerular Filtration Rate, Renal Fibrosis and Biomarkers in a Rat Model of Type 2 Diabetic Nephropathy," *Am J Nephrol*, 44:339-353 (2016).
Treiber et al., "The metabolism of the dual endothelin receptor antagonist macitentan in rat and dog," *Xenobiotica*, pp. 1-15 (2015).
Treiber et al., "Macitentan Does Not Interfere with Hepatic Bile Salt Transport," *J Pharmacol Exp Ther*, 350:130-143 (2014).
Trensz, "Pharmacology of ACT-132577 (aprocitentan): A dual endothelin receptor antagonist for the treatment of resistant hypertension," *Idorsia—ET-15 Conference*—Prague, 19 pages (2017).
Trensz et al., "Pharmacology of ACT-132577, a Dual Endothelin Receptor Antagonist for the Treatment of Resistant Hypertension," *Program & Abstract Book*, ET-15—Prague—Czech Republic, 2 pages (2017).
Tullos et al., "Chronic blockade of endothelin A and B receptors using macitentan in experimental renovascular disease," *Nephrol Dial Transplant*, 0: 1-10 (2014).
Valero-Munoz et al., "Dual Endothelin-A/Endothelin-B Receptor Blockade and Cardiac Remodeling in Heart Failure With Preserved Ejection Fraction," *Circ Heart Fail.*, 9:e003381 pp. 1-9; Supplemental Material, pp. 1-12; pp. 1-12 (2016).
Vercauteren et al., "Endothelin ETA Receptor Blockade, by Activating ETB Receptors, Increases Vascular Permeability and Induces Exaggerated Fluid Retentions," *The Journal of Pharmacology and Experimental Therapeutics*, 361:322-333; Supplementary Material 2 pages (2017).
Wald et al., "Combination Therapy Versus Monotherapy in Reducing Blood Pressure: Meta-analysis on 11,000 Participants from 42 Trials," *The American Journal of Medicine*, 122(3): 290-300 (2009).
Wan et al., "A promising choice in hypertension treatment: Fixed-dose combinations," *Asian Journal of Pharmaceutical Sciences*, 9:1-7 (2014).
Weber et al., "Clinical Practice Guidelines for the Management of Hypertension in the Community A Statement by the American Society of Hypertension and the International Society of Hypertension," *The Journal of Clinical Hypertension*, 16(1):14-26 (2014).
Weber et al., " A selective endothelin-receptor antagonist to reduce blood pressure in patients with treatment-resistant hypertension: a randomized, double-blind, placebo-controlled trial," *The Lancet*, 374: 1423-1431 (2009).
Whelton et al., "2017 ACC/AHA/AAPA/ABC/ACPM/AGS/APhA/ASH/ASPC/NMA/PCNA Guideline for the Prevention, Detection, Evaluation, and Management of High Blood Pressure in Adults," *High Blood Pressure Clinical Practice Guideline*, 481 pages (2017).
Zhang et al., "Pharmacokinetic study of ACT-132577 in rat plasma by ultra performance liquid chromatography-tandem mass spectrometry," *Int J Clin Exp Med*, 8(10):18420-18426 (2015).

Bakris et al., "Divergent Results Using Clinic and Ambulatory Blood Pressures, Report of a Darusentan-Resistant Hypertension Trial," *Hypertension*, 56:824-830 (2010).
Bolli et al., Supporting Information (30 pages) for: "The Discovery of N-[5-(4-Bromophenyl)-6-[2-[(5-bromo-2-pyrimidinyl)oxy]ethoxy]-4-pyrimidinyl]-N'- propylsulfamide (Macitentan), an Orally Active, Potent Dual Endothelin Receptor Antagonist," *J. Med. Chem.*, 55: 7849-7861 (2012).
European Patent Application No. EP 18814821.7/EP3716979 Further Processing—Reply to Rule 161(1) and 162 EPC Communication, 6 pages, filed with the European Patent Office on Apr. 13, 2021.
Gilmore et al., "Inhibitors of NF-kappaB signaling: 785 and counting," 1 page, abstract for *Oncogene*, 25(51): 6887-6899 (2006).
Mann et al., "Avosentan for Overt Diabetic Nephropathy," *J Am Soc Nephrology*, 21(3): 527-535 (2010).
Vercauteren et al., "Endothelin $ET_A$ Receptor Blockade, by Activating $ET_B$ Receptors, Increases Vascular Permeability and Induces Exaggerated Fluid Retention," *The Journal of Pharmacology and Experimental Therapeutics*, 361:322-333; Supplementary Material 2 pages (2017).
Schlaich, M. et al., "Dual Endothelin Antagonist Aprocitentan for Resistant Hypertension (Precision): A Multicentre, Blinded, Randomised, Parallel-group, Phase 3 Trial," The Lancet, 2022, 11 pages, https://doi.org/10.1016/S0140-6736(22)02034-7.
Supplementary Appendix for "Dual Endothelin Antagonist Aprocitentan for Resistant Hypertension (Precision): A Multicentre, Blinded, Randomised, Parallel-group, Phase 3 Trial," The Lancet, 2022, https://doi.org/10.1016/S0140-6736(22)02034-7, 47 pages.
Murugesan, N. et al., "Biphenylsulfonamide Endothelin Antagonists: Structure-Activity Relationships of a Series of Mono- and Disubstituted Analogues and Pharmacology of the Orally Active Endothelin Antagonist 2'-Amino-N-(3,4-dimethyl-5-isoxazolyl)-4'-(2-methylpropyl)[1,1'-biphenyl]-2-sulfonamide (BMS-187308)," Journal of Medicinal Chemistry, 1998, 41, 5198-5218.
Murugesan, N. et al., "Biphenylsulfonamide Endothelin Receptor Antagonists. 2. Discovery of 4'-Oxazolyl Biphenylsulfonamides as a New Class of Potent, Highly Selective $ET_A$ Antagonists," Journal of Medicinal Chemistry, 2000, 43, 3111-3117.
Murugesan, N. et al., "Biphenylsulfonamide Endothelin Receptor Antagonists. 4. Discovery of N-[[2'-[[(4,5-Dimethyl-3-isoxazlyl)amino]sulfonyl]-4-(2-oxazolyl)[1,1'-biphenyl]-2-yl]methyl]-N,3,3-trimethylbutanamide (BMS-207940), A Highly Potent and Orally Active $ET_A$ Selective Antagonist," Journal of Medicinal Chemistry, 2003, 46, 125-137.
Wu, C. et al., "Discovery, Modeling, and Human Pharmacokinetics of N-(2-Acetyl-4,6-dimethylphenyl)-3-(3,4-dimethylisoxazol-5-ylsulfamoyl)-thoiphene-2-carboxamide (TBC3711), a Second Generation, $ET_A$ Selective, and Orally Bioavailable Endothelin Antagonist," Journal of Medicinal Chemistry, 2004, 47, 1969-1986.
U.S. Appl. No. 18/319,402, filed May 17, 2023, Bolli et al.
Anguiano, L. et al., "Endothelin Blockade in Diabetic Kidney Disease," Journal of Clinical Medicine, 2015, 4, 1171-1192.
Baker, W. et al., "Effects of sodium-glucose co-transporter 2 inhibitors on blood pressure: A systematic review and meta-analysis," Journal of the American Society of Hypertension, 2014, 8 (4), 262-275 and 275.e1-275.e9.
Barnett, A. et al., "Efficacy and safety of empagliflozin added to existing antidiabetes treatment in patients with type 2 diabetes and chronic kidney disease: a randomised, double-blind, placebo-controlled trial," The Lancet, Diabetes & Endocrinology, 2014, 2, 369-384.
Benz, K. et al., "Endothelin in Diabetic Renal Disease," Contributions to Nephrology, 2011, 172, 139-148.
Campbell, D. et al., "Defining, Treating, and Understanding Chronic Kidney Disease—A Complex Disorder," The Journal of Clinical Hypertension, 2015, 17 (7), 514-527.
Fadini, G. et al., "SGTL2 inhibitors and amputations in the US FDA Adverse Event Reporting System," The Lancet, Diabetes & Endocrinology, 2017, 5, 680-681.
Fadini, G. et al., Supplementary Appendix for "SGTL2 inhibitors and amputations in the US FDA Adverse Event Reporting System," The Lancet, Diabetes & Endocrinology, 2017, 25 pages.

(56) References Cited

OTHER PUBLICATIONS

Fernandez-Fernandez, B. et al., "Canagliflozin and Renal Events in Diabetes with Established Nephropathy Clinical Evaluation and Study of Diabetic Nephropathy with Atrasentan: what was learned about the treatment of diabetic kidney disease with canagliflozin and atrasentan?" Clinical Kidney Journal, 2019, 12 (3), 313-321.

Garg, S. et al., "Effects of Sotagliflozin Added to Insulin in Patients with Type 1 Diabetes," The New England Journal of Medicine, 2017, 11 pages, doi: 10.1056/NEJMoa1708337.

Georgianos, P., et al. "Endothelin A receptor antagonists in diabetic kidney disease," Current Opinion in Nephrology and Hypertension, 2017, 26 (5), 338-344.

Heerspink, H. et al., "Canagliflozin Slows Progression of Renal Function Decline Independently of Glycemic Effects," Journal of the American Society of Nephrology, 2016, 28, 8 pages, doi: 10.1681/ASN2016030278.

Heerspink, H. et al., "Dapagliflozin a glucose-regulating drug with diuretic properties in subjects with type 2 diabetes," Diabetes, Obesity and Metabolism, 2013, 15 (9), 853-862.

Heise, T. et al., "Acute Pharmacodynamic Effects of Empagliflozin With and Without Diuretic Agents in Patients With Type 2 Diabetes Mellitus," Clinical Therapeutics, 2016, 38 (10), 2248-2264 and 2264.e1-2264.e5.

Heise, T. et al., "Pharmacodynamic Effects of Single and Multiple Doses of Empagliflozin in Patients With Type 2 Diabetes," Clinical Therapeutics, 2016, 38 (10), 2265-2276.

Iglarz, M. et al., "At the heart of tissue: endothelin system and end-organ damage," Clinical Science, 2010, 119, 453-463.

Inagaki, N. et al., "Efficacy and safety of canagliflozin alone or as add-on to other oral antihyperglycemic drugs in Japanese patients with type 2 diabetes: A 52-week open-label study," Journal of Diabetes Investigation, 2015, 6, 210-218.

Jandeleit-Dahm, K. et al., "The endothelin system and endothelin receptor antagonists," Current Opinion in Nephrology and Hypertension, 2012, 21 (1), 66-71.

Neal, B. et al., "Canagliflozin and Cardiovascular and Renal Events in Type 2 Diabetes," The New England Journal of Medicine, 2017, 377, 644-657.

Oelze, M. et al., "The Sodium-Glucose Co-Transporter 2 Inhibitor Empagliflozin Improves Diabetes-Induced Vascular Dysfunction in the Streptozotocin Diabetes Rat Model by Interfering with Oxidative Stress and Glucotoxicity," PLoS One, 2014, 9 (11), e112394, 13 pages, doi: 10.1371/journal.pone.0122394.

Rahman, A. et al., "Effects of diuretics on sodium-dependent glucose cotransporter 2 inhibitor-induced changes in blood pressure in obese rats suffering from the metabolic syndrome," Journal of Hypertension, 2016, 34, 893-906.

Sjöström, C. et al., "Dapagliflozin-induced weight loss affects 24-week glycated haemoglobin and blood pressure levels," Diabetes, Obesity and Metabolism, 2015, 17, 809-812.

Tanaka, A. et al., "Increased amputation risk with canagliflozin treatment: behind the large cardiovascular benefit?," Cardiovascular Diabetology, 2017, 16:129, 3 pages, doi: 10.1186/s12933-017-0611-x.

Umanath, K. et al., "Update on Diabetic Nephropathy: Core Curriculum 2018," American Journal of Kidney Diseases, 2018, 71 (6), 884-895.

Weber, M. et al., "Effects of dapagliflozin on blood pressure in hypertensive diabetic patients on renin-angiotensin system blockade," Blood Pressure, 2016, 25 (2), 93-103.

Yuan, Z. et al., "Risk of lower extremity amputations in people with type 2 diabetes mellitus treated with sodium-glucose cotransporter-2 inhibitors in the USA: A retrospective cohort study," Diabetes, Obesity, and Metabolism, 2017, 1-8, https://doi.org/10.1111/dom.13115.

Zell, M. et al., "Metabolism and mass balance of SGLT2 inhibitor tofogliflozin following oral administration to humans," Xenobiotica, 2014, 44 (4), 369-378.

Zinman, B. et al., "Empagliflozin, Cardiovascular Outcomes, and Mortality in Type 2 Diabetes," The New England Journal of Medicine, 2015, 373, 2117-2128.

* cited by examiner

Fig. 1, Form A
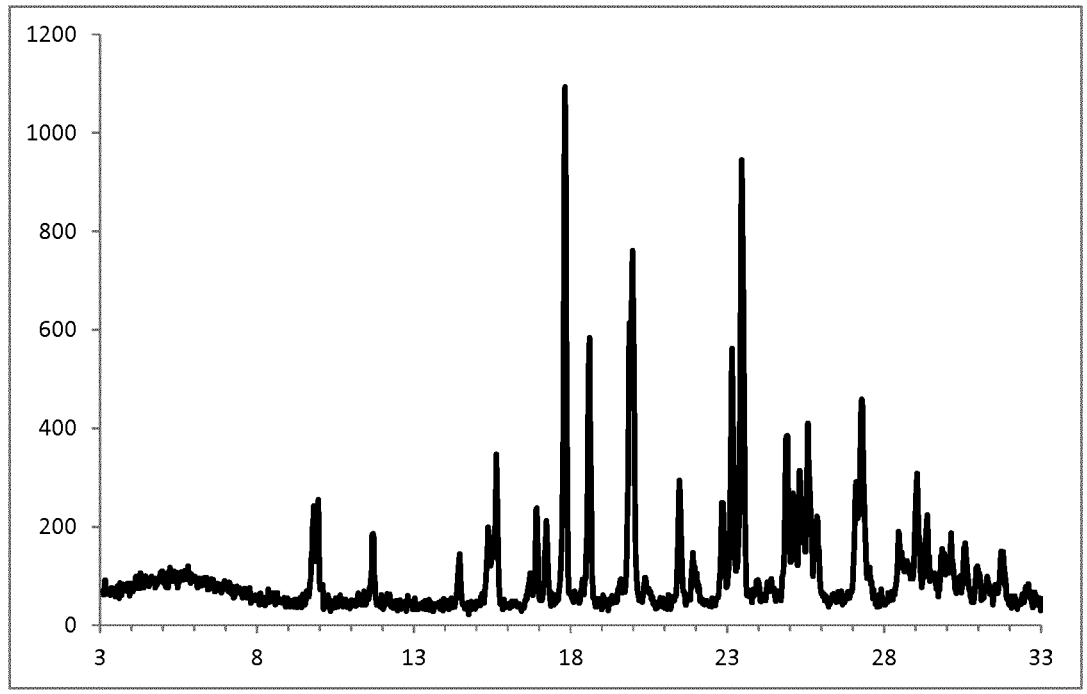
Fig. 2, Form C
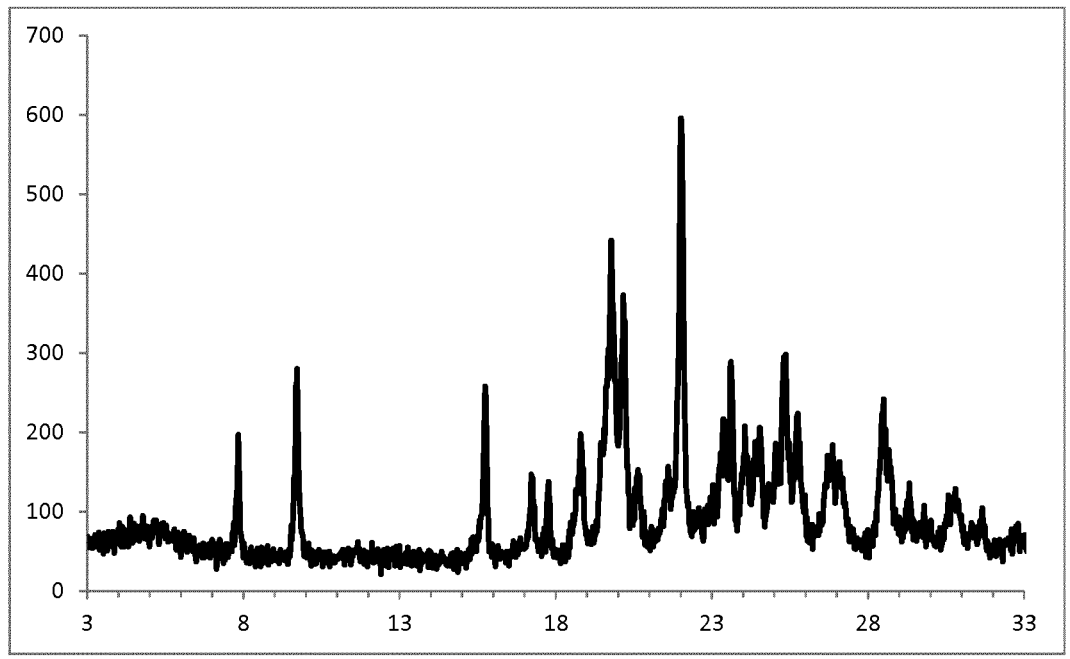

COMBINATION OF A 4-PYRIMIDINESULFAMIDE DERIVATIVE WITH AN SGLT-2 INHIBITOR FOR THE TREATMENT OF ENDOTHELIN RELATED DISEASES

CROSS REFERENCE TO RELATED APPLICATIONS

This application is a United States Application under 35 U.S.C. 371 claiming benefit of PCT Application No. PCT/EP2018/082947, filed on Nov. 29, 2018, which claims the benefit of PCT Application No. PCT/EP2017/081050, filed on Nov. 30, 2017, the contents of each of which are incorporated herein by reference.

The present invention concerns the compound aprocitentan and its use as endothelin receptor antagonist, in combination with other active ingredients or therapeutic agents comprising a sodium glucose cotransporter 2 (SGLT-2) inhibitor the prophylaxis or treatment of certain endothelin related diseases. The invention further relates to pharmaceutical compositions comprising aprocitentan in combination with said other active ingredient(s) or therapeutic agent(s). The invention further relates to such pharmaceutical compositions comprising novel crystalline forms of aprocitentan; pharmaceutical compositions prepared from such crystalline forms, and to the use of such crystalline forms in combination with said other active ingredients or therapeutic agents in the prophylaxis or treatment of said endothelin related diseases.

Aprocitentan, {5-(4-bromo-phenyl)-6-[2-(5-bromo-pyrimidin-2-yloxy)-ethoxy]-pyrimidin-4-yl}-sulfamide (hereinafter also referred to as "COMPOUND"), has the formula I

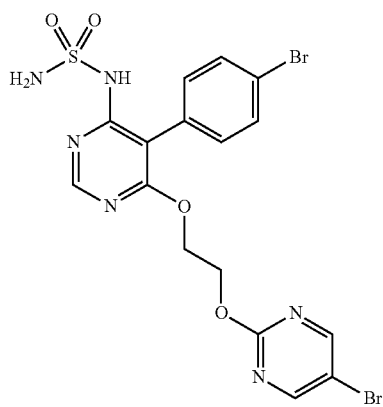 [SMILES: NS(=O)(=O)Nc1ncnc(OCCOc2ncc(Br)cn2)c1-c1ccc(Br)cc1]

Formula I

The compound of formula I, also known under the name, and referred to as ACT-132577, is an endothelin receptor antagonist. The compound of formula I is a member of a structural family that was previously generically disclosed in WO 02/053557. In particular, the compound of formula I, while showing endothelin receptor antagonist activity, exhibits in vivo a much longer half-life and a much shorter clearance in comparison to corresponding alkylated derivatives. This makes the compound of formula I particularly suitable for long-acting pharmaceutical compositions, as disclosed in WO 2009/024906.

Because of its ability to inhibit the endothelin binding, the compound of formula I can be used for treatment of endothelin related diseases which are associated with an increase in vasoconstriction, proliferation or inflammation due to endothelin occurring in many cardio-renal-metabolic diseases. Examples of such endothelin related diseases are hypertension including especially difficult to treat/resistant hypertension; pulmonary hypertension; coronary diseases; cardiac insufficiency; renal and myocardial ischemia; chronic kidney disease (CKD) [especially CKD of stages 1 to 4 as defined by the Kidney Disease Improving Global Outcomes (KDIGO) Guidelines (and notably CKD of stage 3), and in particular CKD (notably of these stages) caused by/associated with hypertension or diabetes (diabetic kidney disease (DKD), including DKD that is associated, in addition, with hypertension); diabetes, and diabetes related diseases such as diabetic arteriopathy, diabetic nephropathy, diabetic retinopathy, or diabetic vasculopathy; reducing the risk of developing a major cardiovascular event (such as heart failure (HF), myocardial infarction, stroke, or death from cardiovascular causes) in patients who have diabetes, especially in patients who have diabetes that is accompanied by at least one other cardiovascular risk factor (such as hypertension, dyslipedemia, thrombotic phenomenom); therapy and prophylaxis of diabetic complications; (acute and chronic) renal failure; glomerulonephritis; connective tissue diseases; atherosclerosis; peripheral arterial disease including chronic peripheral (obliterant) arteriopathy; digital ulcers; diabetic foot ulcers and/or reducing the risk of lower limb/extremety amputations in patients who have diabetes, or who are smokers, or who have atherosclerosis; heart failure (HF) defined as including especially chronic HF, including in particular systolic HF/HF with reduced ejection fraction (HFrEF) (i.e. ejection fraction<about 40%), and diastolic HF/HF with preserved ejection fraction (HFpEF) (i.e. ejection fraction>about 50%); reducing the risk of developing a major cardiovascular event (such as heart failure (HF), myocardial infarction, stroke, or death from cardiovascular causes) in patients who are at cardiovascular risk (such as patients who have coronary artery disease and/or patients who have demonstrated clinical signs of congestive heart failure); angina pectoris; and diastolic dysfunction. The compound of formula I can also be used in the treatment or prevention of cerebral ischemia; dementia; migraine; subarachnoidal hemorrhage; Raynaud's syndrome; portal hypertension; restenosis after balloon or stent angioplasty; inflammation; stomach and duodenal ulcer; cancer; melanoma; prostate cancer; prostatic hypertrophy; erectile dysfunction; eclampsia; hearing loss; amaurosis; chronic bronchitis; asthma; pulmonary fibrosis; gram negative septicemia; shock, sickle cell anemia; renal colic; glaucoma; complications of vascular or cardiac surgery or after organ transplantation; complications of cyclosporin treatment or equivalent therapies showing nephrotoxic profile; pain; dyslipidemia; as well as other diseases presently known to be related to endothelin.

Clinical studies have shown that endothelin receptor antagonists (ERAs) may have significant treatment effect in patients suffering from hypertension and/or renal disease, whether associated or not with diabetes. Endothelin 1 (ET-1) is likely to play a role in the pathogenic mechanisms of chronic diabetic arteriopathy, because of its effects on mediating plaque formation, thrombosis, vasoconstriction, and vascular hypertrophy and because it potentiates the action of other systems, in particular the renin angiotensin and sympathetic systems and/or insulin signalings. Thus, an ERA might be beneficial in the treatment of peripheral arterial obliterant disease including diabetic arteriopathy by having acute (peripheral vasodilation) and chronic (vasodilation, improvement in vascular structure and modulation of sympathetic activity, antithrombotic, antiinflamatory) effects. In a clinical network meta-analysis of studies performed in adults with diabetes and CKD (157 studies comprising 43,256 patients), ERAs were ranked as the most effective agents for the prevention of end-stage kidney disease (S. C. Palmer et al., Lancet (2015), 385 (9982): 2047-2056). However, therapeutic benefit needs to be weighted against potential side effects, such as the potential risk of teratogenic activity generally associated with ERAs. In addition and more importantly, both, selective $ET_A$-antagonists and dual antagonists of both the $ET_A$ and $ET_B$ receptor, may cause fluid retention, a common side effect associated with many previously studied ERAs and sometimes (e.g. if not manageable with diuretics) leading to exaggerated major adverse cardiac events such as heart failure or death. Whereas the risk-benefit balance is in most cases in favor of treatment with an ERA for indications such as pulmonary hypertension (as reflected in the past by successive market approvals e.g. for the ERAs the dual antagonists bosentan and macitentan, and the $ET_A$-selective antagonist ambrisentan), ERAs have no role in the management of primary hypertension (Laffin et al. Seminars in Nephrology 2015, 35, 168-175), and side effects such as fluid retention may remain an issue when a potential treatment of difficult to treat/resistant hypertension (rHT), chronic kidney disease (CKD), whether associated or not with diabetes and/or hypertension, or other hypertension related diseases with an ERA is considered.

The $ET_A$-selective endothelin receptor antagonist darusentan has been in development for the treatment of resistant hypertension (rHT) (Bakris et al., Hypertension 2010, 56,824-830, see also WO2007/098390). In a 14 week phase 3 trial in patients with rHT, it demonstrated efficacy on the reduction of ambulatory blood pressure, but failed to show significant treatment effect on the primary endpoint systolic blood pressure. Patients were eligible to participate if they had treatment resistant hypertension (systolic blood pressure of higher than 140 mm Hg) despite treatment with three or more antihypertensive drugs from different drug classes, including a diuretic, at optimized doses. A minimum dose of 25 mg per day of hydrochlorothiazide (or its equivalent for other thiazide diuretic drugs) was required. Even though during the trial diuretic therapy could be intensified at the discretion of the investigators to manage fluid retention, the most frequent adverse event associated with darusentan was fluid retention/edema at 28% versus 12% in each of the other groups. More patients withdrew because of adverse events on darusentan as compared with placebo.

The $ET_A$-selective ERA avosentan, in a trial that investigated the effects of avosentan on progression of overt diabetic nephropathy in patients with type 2 diabetes, showed significant treatment effect, associated with a significantly increased discontinuation of trial medications due to adverse events, predominantly related to fluid overload and congestive heart failure (Mann et al., "Avosentan for Overt Diabetic Nephropathy", J Am Soc Nephrol. 2010, 21(3): 527-535). The composite primary outcome was the time to doubling of serum creatinine, ESRD, or death. Secondary outcomes included changes in albumin-to-creatinine ratio (ACR) and cardiovascular outcomes. The study did not detect a difference in the frequency of the primary outcome between groups. Avosentan significantly reduced ACR. The trial was terminated prematurely after a median follow-up of 4 months (maximum 16 months) because of an excess of cardiovascular events with avosentan, and the authors conclude that "it may be that at dosages of 25 to 50 mg avosentan is less selective for the $ET_A$ receptor and thus caused sodium and water retention and peripheral vasodilation with a potential fluid shift from the intravascular to extravascular space". The effect on albuminuria was considered likely due to inhibition of the renal $ET_A$ receptor, because it was previously found that the mixed type $ET_{A/B}$ receptor antagonists have a weaker or no effect on proteinuria. According to the authors, the assumption of $ET_B$ receptor blockade with higher dosages of avosentan is further supported by data that showed a natriuretic effect of selective $ET_A$ receptor blockade in people who were treated with ACE inhibitors. Thus, the natriuretic effect/fluid retention that possibly in final consequence lead to the discontinuation of the trial was attributed to a dual blockade of the $ET_A$ and the $ET_B$ receptor, discouraging from using a dual acting ERA in such clinical setting.

Further pre-clinical data showed that the synergistic effect on blood pressure of an $ET_A$-selective ERA in combination with the ACE inhibitor enalapril was abolished by simultaneous blockade of the $ET_B$-receptor (Goddard et al., J. Am. Soc. Nephrol. 2004, 15, 2601-2610), thus, discouraging from using a dual acting ERA in a clinical setting where ACE inhibitors may be required as background therapy.

In a review on "Endothelin antagonists for diabetic and non-diabetic chronic kidney disease" (Br J Clin Pharmacol (2012), 76:4, 573-579), D. E. Kohan et al. state that "in general, the prevailing opinion is that $ET_A$, as opposed to combined $ET_{A/B}$, receptor antagonists are preferred for treating CKD". Three years later Kohan et al. conclude with regard to a study published in Clin J Am Soc Nephrol (2015), 10: 1568-1574 that "the fluid-retaining effect of ERAs is most likely related to direct effects on renal tubular sodium transport, whereas the antiproteinuric effect of ERAs is likely associated with actions on the vasculature and/or glomerulus. Finally, it could be anticipated that ERA mitigation of proteinuria per se would favor renal fluid excretion; however, ERAs could still promote fluid retention through a separate effect on tubule sodium and water reabsorption".

WO2016/073846 provides a comprehensive summary of ERAs tested for various indications including diabetic and non-diabetic CKD and rHT. WO2016/073846 provides further examples where fluid retention may have led to increased side effects for the ERAs bosentan, tezosentan, ambrisentan, and atrasentan. WO2016/073846 concludes in proposing a method of treating CKD with an ERA, especially with the $ET_A$-selective ERA atrasentan, using predictors of fluid retention; said method comprising the determination of a risk of fluid retention if an ERA were administered to the subject; and administering the ERA to the subject if the risk is at an acceptable level. The detailed study protocol of a clinical phase 3 study (SONAR) evaluating the effects of the investigational compound atrasentan—when added to standard of care—on progression of kidney disease in patients with stage 2 to 4 chronic kidney disease and type 2 diabetes was published in Heerspink et al, Diabetes Obes. Metab. 2018, 1-8. The protocol reflects the importance given to dose optimization and simultaneous control of sodium retention/fluid retention in the study design, leading to a study design that requires "the selection of individuals at high risk of disease (prognostic enrichment) who also demonstrate a good response to study treatment (predictive enrichment)". However, on Dec. 1, 2017, AbbVie announced its strategic decision to close the SONAR study. The press release states that "the ongoing monitoring of renal events observed in the study has revealed considerably fewer end-points than expected by this time, which will likely affect the ability to test the SONAR study hypothesis. Therefore, AbbVie has determined that it cannot justify continuing the participation of patients in the study. The decision to close the SONAR study early was not related to any safety concerns."

Contrary to the conclusions drawn from the avosentan trial, preclinical and clinical data suggest that the $ET_A$-selective antagonists sitaxentan and ambrisentan pose a greater risk of fluid retention than the dual ERAs bosentan and macitentan (Vercauteren et al., JPET 2017, 361, 322-333). The authors state that their findings "indicate that in rats, stimulation of the unblocked $ET_B$ receptors in presence of $ET_A$ receptor antagonist, but not functional antagonism of the $ET_A$ receptor per se, can be detrimental, and that blockade of both receptors is less likely to cause water retention than single receptor blockade" and continue to speculate that "plasma volume expansion combined with increased vascular permeability could explain the observations obtained with $ET_A$-selective antagonists". The authors conclude that "several clinical studies with $ET_A$-selective antagonists have resulted in mortality increases in relation to fluid retention issues, whereas this has not been observed with dual ERAs. Dual ERAs, however, in conditions of preexisting fluid retention or arginine vasopressin (AVP) increase, such as chronic heart failure or chronic renal failure, have caused significant fluid retention".

It has been shown in a phase 2 clinical trial that aprocitentan, an ERA resulting in effective dual blockade of the endothelin receptors, may result in efficacious control of blood pressure in subjects having essential hypertension (aprocitentan was administered as monotherapy, i.e. without background anti-hypertensive therapy) (Actelion Pharmaceuticals Ltd, press release May 22, 2017). Even though some indications of potential fluid retention were observed (e.g. increased body weight at higher doses, dose related decrease in the hemoglobin concentration, four cases of peripheral edema at higher doses), the overall frequency of adverse events was similar to those observed in the placebo group. Thus, different from the methods of WO2016/073846 no risk assessment and/or dose reduction to mitigate side effects related to fluid retention may be required for aprocitentan when used in the treatment of hypertension related diseases, especially resistant hypertension. Thus, aprocitentan may have a different pharmacological profile than the predominantly $ET_A$-selective antagonists so far tested in resistant hypertension or chronic kidney disease in diabetic and non-diabetic patients.

Moreover, it has been found in rat models of hypertension that aprocitentan may have synergistic pharmacological effect in combination with the angiotensin receptor blocker (ARB) valsartan, synergistic pharmacological effect in combination with the angiotensin converting enzyme (ACE) inhibitor enalapril, and synergistic pharmacological effect in combination with the calcium channel blocker (CCB) amlodipine, compared to the effect of the respective active ingredients alone. ARBs, ACE inhibitors and CCBs are standard treatments per guideline requirements, generally prescribed, alone or in combination, to hypertensive patients, often in combination with a diuretic, especially a diuretic of the thiazide class such as hydrochlorothiazide.

SGLT-2 inhibitors block glucose reabsorption in the kidney, increase glucose excretion, and lower blood glucose concentration. In addition to this well characterized mode of action, SGLT-2 inhibitors reduce blood pressure, decrease vascular stiffness, improve endothelial function, and have anti-inflammatory and anti-fibrotic properties resembling those of ERAs (H. J. Heerspink et al., Circulation (2016), 134(10): 752-772). This unique mechanism of action lead to the development and market approval of several SGLT-2 inhibitors comprising canagliflozin, dapagliflozin and empagliflozin, all indicated to improve glycemic control in adults with type 2 diabetes mellitus, empagliflozin in addition being indicated to reduce the risk of cardiovascular death in such patients having established cardiovascular disease. Sotagliflozin, a dual SGLT-1 and SGLT-2 inhibitor has been reported to be in clinical trials for type 1 diabetes.

WO2010/138535 claims a method for treating type 2 diabetes in a mammalian patient who has previously been treated with one or more oral anti-diabetic agents and/or one or more injectable anti-diabetic agents, which previous treatment has failed, which comprises administering to said patient in need of treatment a therapeutically effective amount of an SGLT2 inhibitor, especially dapagliflozin. WO2010/138535, among numerous other speculative combinations, further discloses such method using an SGLT2 inhibitor such as dapagliflozin in combination with one or more anti-hypertensive agent, which are for example beta adrenergic blockers, calcium channel blockers (L-type and/or T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-I receptor antagonists (e.g., losartan, irbesartan, valsartan), ET receptor antagonists (e.g. sitaxsentan, atrasentan and compounds disclosed in U.S. Pat. Nos. 5,612,359 and 6,043,265), dual ET/AII antagonist, neutral endopeptidase (NEP) inhibitors, vasopeptidase inhibitors (dual NEP-ACE inhibitors) or nitrates. No data supporting a combination with an anti-hypertensive agent compared to other proposed combinations, nor data supporting any particular combination therapy among the various anti-hypertensive agents are provided. Similarly, Kissei Pharmaceuticals Ltd disclosed in several patent applications SGLT-1 and/or SGLT-2 inhibitors useful for the treatment of hyperglycemia such as diabetes, diabetic complications or obesity (see e.g U.S. Pat. Nos. 7,732,596, 7,989,424) which, among numerous other speculative combinations, are disclosed to be useful in combination with endothelin receptor antagonists such as L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 or the like.

Diabetes often concurs with heart failure (HF) and may contribute to its development. SGLT-2 inhibitors such as empagliflozin may be suitable for the treatment of chronic HF, including especially also HFpEF where treatment options are very limited. The EMPA-REG OUTCOME Trial (Empagliflozin, Cardiovascular Outcomes, and Mortality in Type 2 Diabetes) randomized type II diabetic patients with high cardiovascular risk to empagliflozin or standard of care. The results suggested improvement in cardiovascular death, non-fatal myocardial infarction, nonfatal stroke, hospitalization for HF, and death from any cause. A post hoc study looking at patients with a diagnosis of HF at baseline suggested significantly lowered cardiovascular death, HF hospitalization, and all cause hospitalization (D. H. Kim et al., "Pharmacologic Management for Heart Failure and Emerging Therapies" Curr Cardiol. Rep (2017) 19:94). The mode of action of SGLT-2 leads to simultaneous inhibition of glucose and sodium uptake in the proximal tubules of the nephron, believed to result in a reset of the tubulo-glomerular feedback putatively causing the phenomenon of glomerular hyperfiltration. Efficacy of SGLT-2 inhibitors is believed to decrease with lower plasma glucose levels or a drop in glomerular filtration rate (GFR), thus, SGLT-2 inhibitors have an inherent low risk for developing hypoglycemia. In consequence, the properties of SGLT-2 inhibitors may open a pathway to treat HF including HFpEF even in non-diabetic patients (P. Martens et al., "Promise of SGLT2 Inhibitors in Heart Failure: Diabetes and Beyond", Curr Treat Options Cardio Med (2017) 19: 23).

A side effect associated with the pharmacological effects of SGLT-2 inhibitors is volume depletion/intravascular volume contraction, potentially leading to dehydration, hypovolemia, orthostatic hypotension, or hypotension. Thus, SGLT-2 inhibitors generally induce an increase in hematocrit (Hct) a marker of haemoconcentration and increased blood viscosity, a putative cause of vascular injury in a context of peripheral vascular disease. In two large trials evaluating the SGLT-2 inhibitor canagliflozin in patients with diabetes type 2 (CANVAS and CANVAS-R), an increased risk of lower limb amputations was observed. The European Medicines Agency assessed these findings (EMA/PRAC/637349/2016) in view of a potential class effect linked to volume reduction and impaired tissue perfusion in the lower limb so that patients with already impaired perfusion would likely develop conditions that lead to amputations. The EMA concluded that a class effect could be neither proven nor disproven.

Furthermore, data from large clinical trials suggest that SGLT2 inhibitors may induce acute kidney injury and impairment in renal function, especially in patients predisposed to acute kidney injury where hypovolemia, chronic renal insufficiency, congestive heart failure and concomitant medications (diuretics, ACE inhibitors, ARBs and NSAIDs) are to be considered. The pharmacological action of SGLT-2 inhibitors on the kidney includes an increase of serum creatinine and a decrease eGFR.

Thus, aprocitentan, an ERA resulting in effective dual blockade of the endothelin receptors, may be particularly suited for the treatment of endothelin related diseases when prescribed in combination with SGLT-2 inhibitors such as atigliflozin, bexagliflozin, canagliflozin, dapagliflozin, empagliflozin, ertugliflozin, henagliflozin, ipragliflozin, luseogliflozin, remogliflozin, sotagliflozin, tianagliflozin, or tofogliflozin (especially canagliflozin, dapagliflozin, or empagliflozin; in particular canagliflozin). The use of the dual ERA aprocitentan in combination with an SGLT-2 inhibitor may result in a particularly beneficial complementary pharmacological action of the two modes of action, both in view of complementary, additive or even synergistic treatment effect, as well as complementary mitigation of the respective side effects of each active ingredient of such combination therapy.

When combining an ERA with an SGLT-2 inhibitor, the diuretic effect of such SGLT-2 inhibitor and its potential pharmacological action in reducing the risk of heart failure may be suitable to mitigate the most prominent side effects generally associated with ERAs such as fluid retention and potentially associated increased risk of congestive heart failure. In particular aprocitentan having shown a particularly benign safety profile in a phase II study in (essential) hypertension patients may be suitable for such combination. Such combination treatment may result in pharmacological action on the disclosed endothelin related diseases, while maintaining a benign side effect profile even at optimal efficacious dosages of aprocitentan, potentially even at increased dosages of aprocitentan when compared to maximum tolerated doses of aprocitentan alone, or aprocitentan in combination for example with standard diuretics such as thiazide-like diuretics including hydrochlorothiazide, and/or aldosterone antagonists. Increased doses of aprocitentan that may become accessible, e.g. due to mitigated side effects, when aprocitentan is used in combination with an SGLT-2 inhibitor may allow to amplify the impact on diseases that are caused by deleterious effects of the endothelin paracrine system widely distributed in the organism. Such combination treatment may improve the benefit/risk ratio and e.g. not require the risk assessment methods of WO2016/073846 and/or dose reductions to mitigate side effects, e.g. related to fluid retention.

In addition to the above-mentioned potential effects of an SGLT-2 inhibitor on the pharmacological effect and/or the side effect profile of the ERA aprocitentan, the ERA aprocitentan in turn may have complementary effect on the pharmacological effect and/or the side effect profile of the respective SGLT-2 inhibitor. ERAs have been described to decrease hematocrit (Hct) via hemodilution. Thus, aprocitentan when used in combination with SGLT-2 inhibitors may antagonize the most prominent side effects generally associated with SGLT-2 inhibitors such as hemoconcentration due to volume depleting effect, possibly contributing to an increased risk of lower extremety/limb amputations. Furthermore, ERAs have been described to provide renal protection and improve renal hemodynamics. Thus, aprocitentan when used in combination with SGLT-2 inhibitors may mitigate the risk of acute renal failure, one of the reported risks of currently approved SGLT-2 inhibitors. Furthermore, ERAs are expected to decrease blood pressure by preventing the vasoconstrictive effect of ET-1 resulting from its binding to ET receptors, thus, aprocitentan when used in combination with SGLT-2 inhibitors may contribute its pronounced pharmacological effect on blood pressure reduction and the consequences of thereof (vascular remodelling, end organ damage, decreased cardiovascular risk caused by/associated with diabetes and/or hypertension). Furthermore, ERAs have been described to improve blood sugar levels by various mechanisms (increased blood flow, improvement of insulin signalling). Thus, aprocitentan when used in combination with SGLT-2 inhibitors may have additive, or even synergistic effects on blood sugar reduction. In addition, volume depletion may be associated with increased blood viscosity. Sloop et al. (Ther Adv Cardiovasc Dis (2015), 9(1) 19-25) state that "The reason why the pathogenesis of chronic vascular diseases, including atherosclerosis, hypertension, and the metabolic syndrome, is not fully understood by the mainstream is because the role of blood viscosity has been ignored.", and that "Theoretically, because flow is inversely proportional to viscosity, reducing blood viscosity should improve perfusion of muscle and increase glucose utilization, decreasing blood glucose levels". Thus, the combination of aprocitentan and a SGLT-2 inhibitor may lead, by a complementary normalization of both the volume depleting effect generally associated with SGLT-2 inhibitors, and the fluid retention effect generally associated with ERAs, to the beneficial pharmacological effects mentioned above, and potentially to additional beneficial pharmacological effects associated with blood viscosity. Finally, aprocitentan which has the pharmacological effect of a dual ERA may be particularly suited for such combination therapy when compared to a selective $ET_A$ receptor antagonist, as it may have low counteracting activity on the beneficial effect of SGLT-2 inhibitors on sodium re-uptake that is associated to the principal pharmacological effect of SGLT-2 on glucose re-uptake.

It has further been found that certain crystalline forms of aprocitentan that are suitable for the production of pharmaceutical compositions may under certain conditions be found. Said crystalline forms of aprocitentan may have advantageous properties in view of the potential use of aprocitentan as active pharmaceutical ingredient. Such advantages may include better flow properties; less hygroscopicity; better reproducibiliy in manufacturing (for example better filtration parameters, better reproducibility of formation, and/or better sedimentation); and/or defined morphology. Such crystalline forms of aprocitentan may be particularly suitable in a process of manufacturing certain pharmaceutical compositions. It has also been found that aprocitentan or a pharmaceutically acceptable salt thereof is particularly useful to treat certain disorders, in particular when used in combination with other active ingredients or therapeutic agents.

DESCRIPTION OF THE FIGURES

FIG. 1 shows the X-ray powder diffraction diagram of COMPOUND in a crystalline form A as obtained from Example 1. The X-ray diffraction diagram shows peaks having a relative intensity, as compared to the most intense peak in the diagram, of the following percentages (relative peak intensitites given in parenthesis) at the indicated angles of refraction 2theta (selected peaks from the range 3-33° 2theta with relative intensity larger then 10% are reported): 9.8° (18%), 9.9° (18%), 11.7° (14%), 14.5° (10%), 15.4° (14%), 15.6° (29%), 16.9° (19%), 17.2° (16%), 17.8° (100%), 18.6° (50%), 19.9° (54%), 20.0° (67%), 21.5° (24%), 21.9° (10%), 22.8° (18%), 23.2° (49%), 23.5° (83%), 24.9° (32%), 25.1° (20%), 25.3° (24%), 25.6° (33%), 25.9° (16%), 27.1° (23%), 27.3° (39%), 28.5° (13%), 29.0° (23%), 29.4° (15%), 30.1° (12%) and 30.6° (10%).

FIG. 2 shows the X-ray powder diffraction diagram of COMPOUND in a crystalline form C as obtained from Example 2. The X-ray diffraction diagram shows peaks having a relative intensity, as compared to the most intense peak in the diagram, of the following percentages (relative peak intensitites given in parenthesis) at the indicated angles of refraction 2theta (selected peaks from the range 3-33° 2theta with relative intensity larger then 10% are reported): 7.8° (23%), 9.7° (42%), 15.7° (37%), 17.2° (16%), 17.8° (15%), 18.8° (26%), 19.8° (71%), 20.1° (51%), 20.6° (15%), 21.6° (15%), 22.0° (100%), 23.4° (27%), 23.6° (40%), 24.1° (23%), 24.5° (16%), 25.1° (13%), 25.3° (39%), 25.7° (28%), 26.8° (19%), 27.1° (16%), 28.5° (31%), 30.8° (13%) and 30.8° (13%).

It is understood, that the crystalline forms disclosed herein comprise the COMPOUND in a crystalline form of the free base (i.e. not in form of a salt). Furthermore, said crystalline forms may comprise non-coordinated and/or coordinated solvent. Coordinated solvent is used herein as term for a crystalline solvate. Likewise, non-coordinated solvent is used herein as term for physiosorbed or physically entrapped solvent (definitions according to Polymorphism in the Pharmaceutical Industry (Ed. R. Hilfiker, VCH, 2006), Chapter 8: U. J. Griesser: The Importance of Solvates). Crystalline forms A and C are anhydrate/ansolvate forms.

Figure 3:
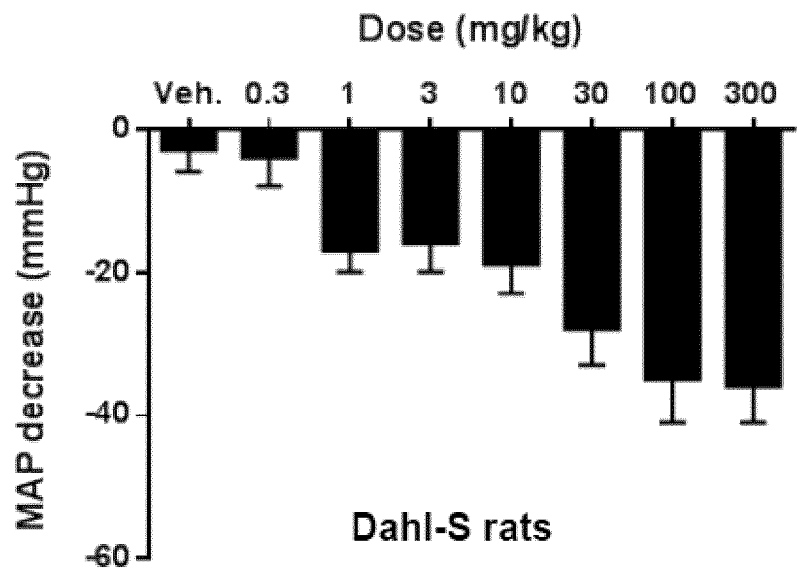

FIG. 3 shows the acute effects of ACT-132577 on mean arterial blood pressure ("MAP") in conscious, male hypertensive Dahl salt sensitive rats.

Figure 4:
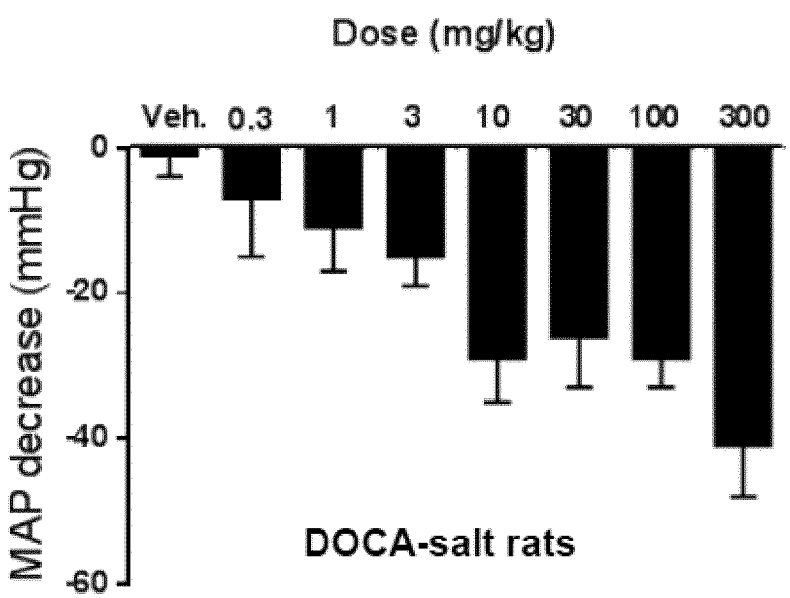

FIG. 4 shows the acute effects of ACT-132577 on MAP in conscious, male hypertensive deoxycorticosterone acetate salt rats.

Figure 5:
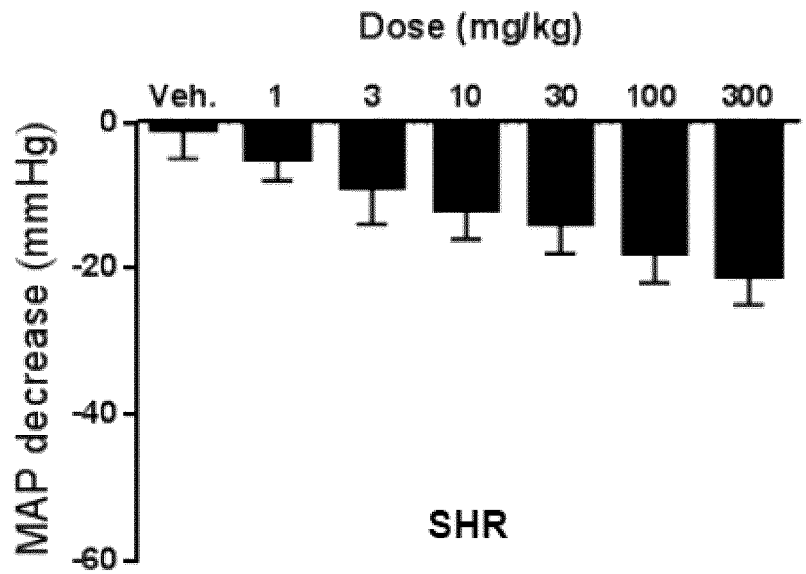

FIG. 5 shows the acute effects of ACT-132577 on MAP in conscious, male spontaneaously hypertensive rats.

Figure 6:
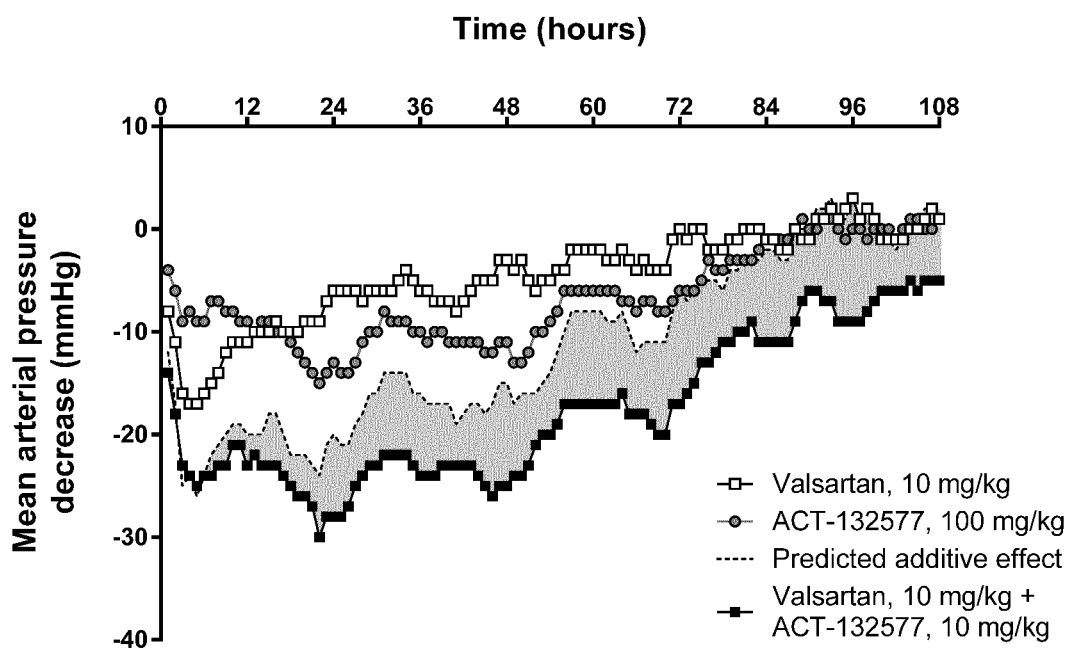

FIG. 6 shows the acute effects of ACT-132577, used alone or in combination with valsartan, on MAP in conscious, male spontaneaously hypertensive rats.

Figure 7:
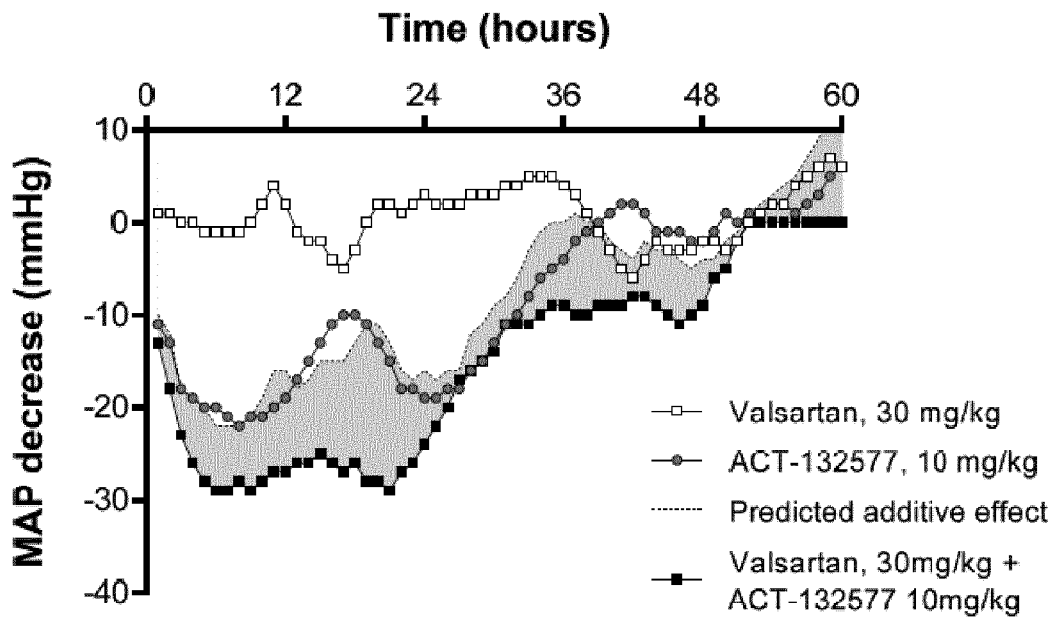

FIG. 7 shows the acute effects of ACT-132577, used alone or in combination with valsartan, on MAP in conscious, male hypertensive deoxycorticosterone acetate salt rats.

Figure 8:
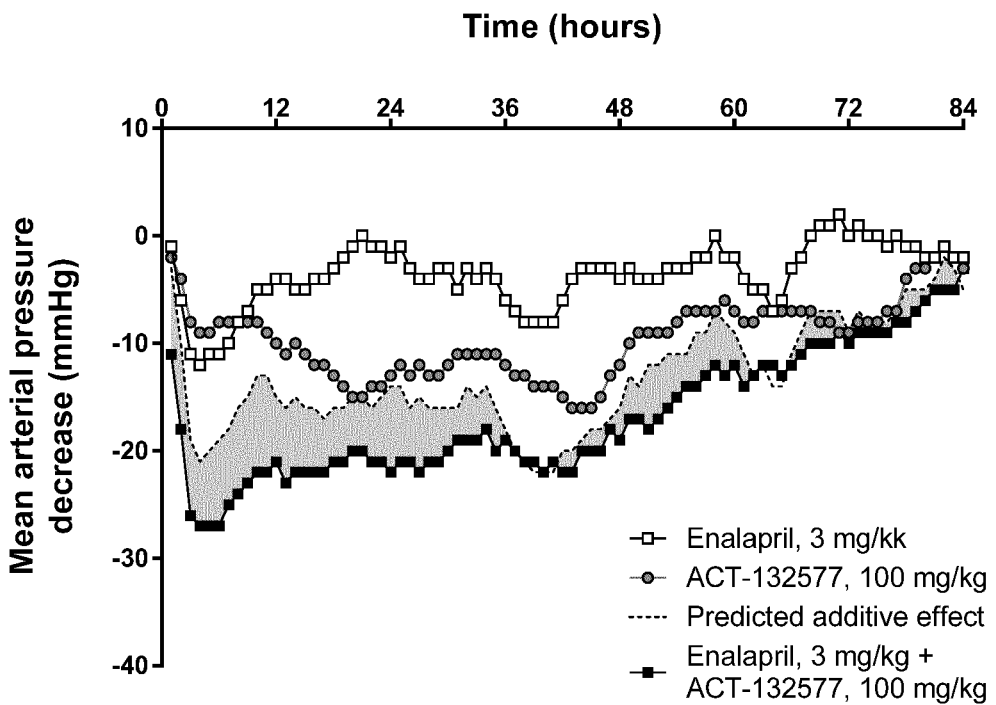

FIG. 8 shows the acute effects of ACT-132577, used alone or in combination with enalapril, on MAP in conscious, male spontaneaously hypertensive rats.

Figure 9:
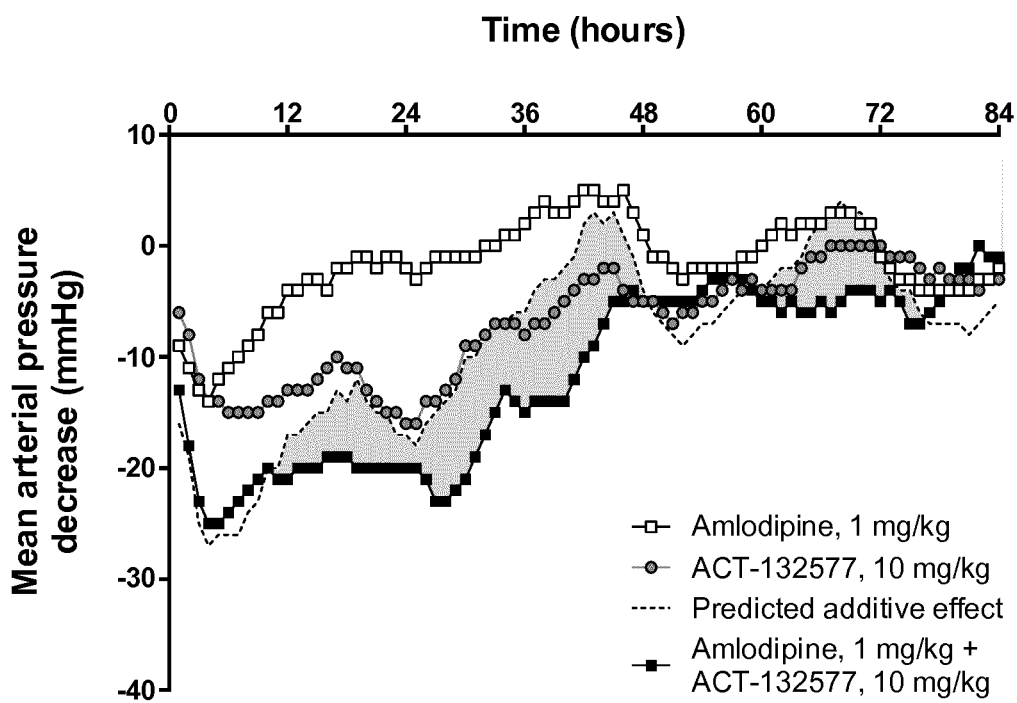

FIG. 9 shows the acute effects of ACT-132577, used alone or in combination with amlodipine, on MAP in conscious, male hypertensive deoxycorticosterone acetate salt rats.

Figure 10:
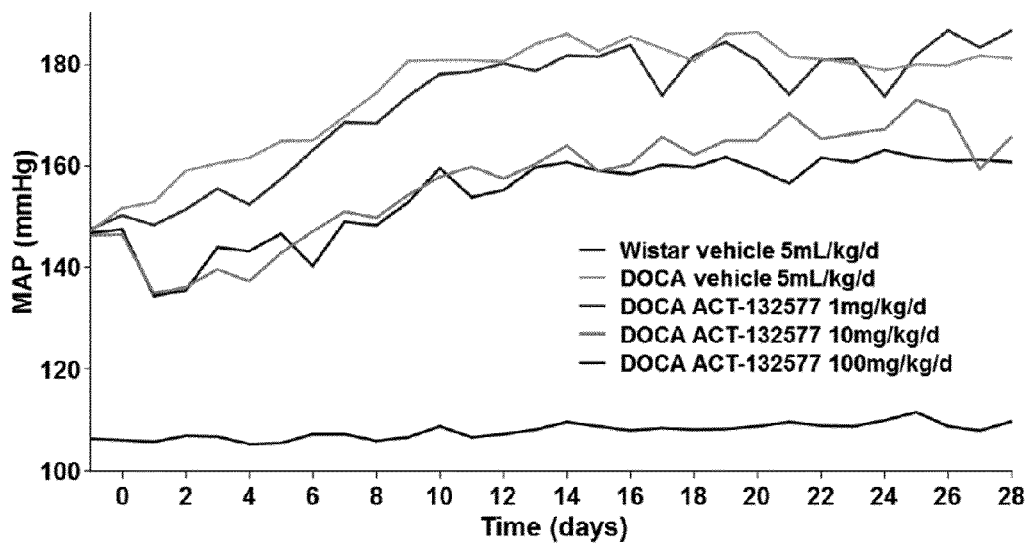

FIG. 10 shows the effects of chronic oral administration of ACT-132577 on MAP in conscious, male hypertensive deoxycorticosterone acetate salt rats.

Figure 11:
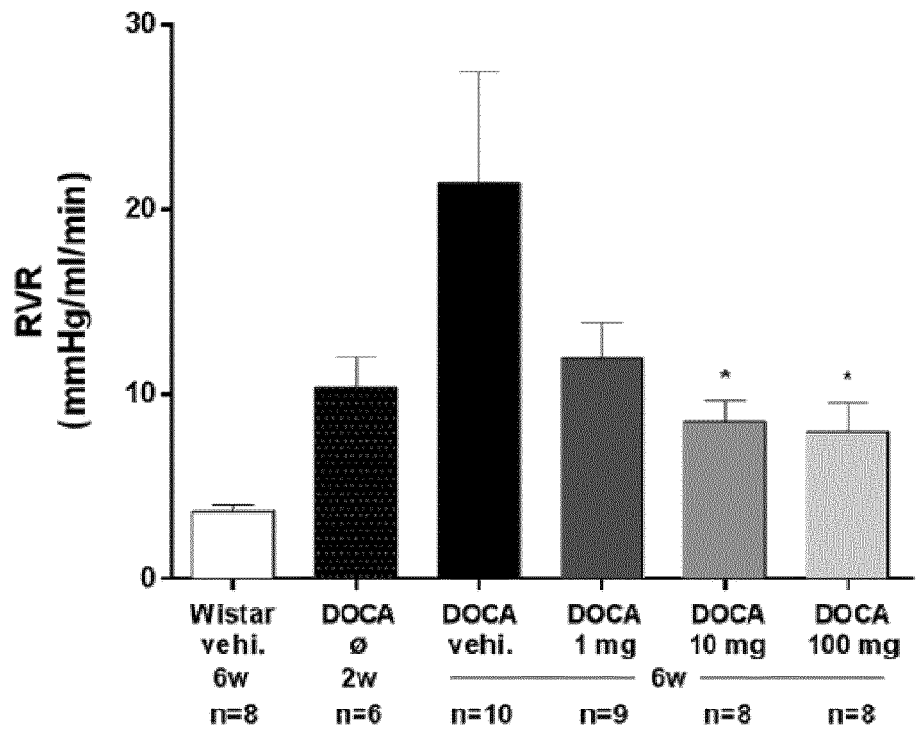

FIG. 11 shows the effects of chronic oral administration of ACT-132577 on renal vascular resistance in conscious, male hypertensive deoxycorticosterone acetate salt rats.

Figure 12:
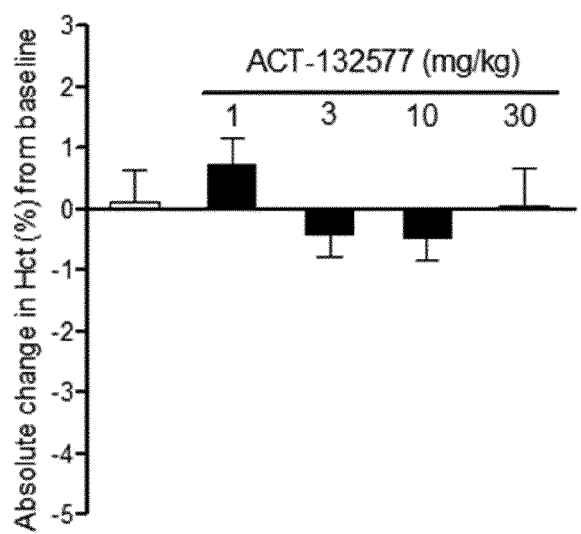

FIG. 12 shows the acute dose-response effect of aprocitentan 1 mg/kg, 3 mg/kg, 10 mg/kg, 30 mg/kg) on haematocrit (Hct) 24 hours after a single oral administration to Wistar rats.

Figure 13:
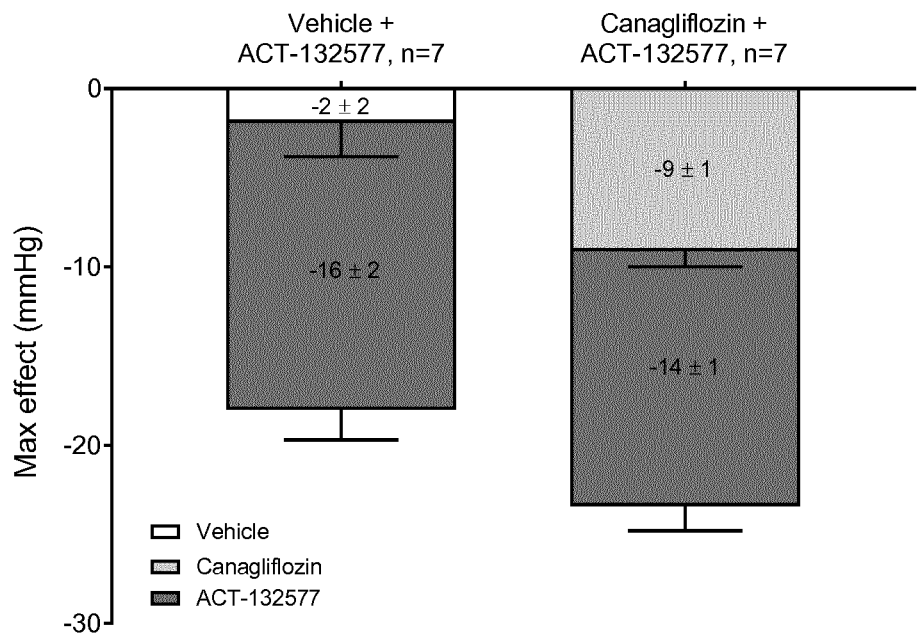

FIG. 13 shows the acute effects of ACT-132577, used alone or in combination with canagliflozin, on maximal effects on MAP in conscious, male spontaneaously hypertensive rats.

Figure 14:
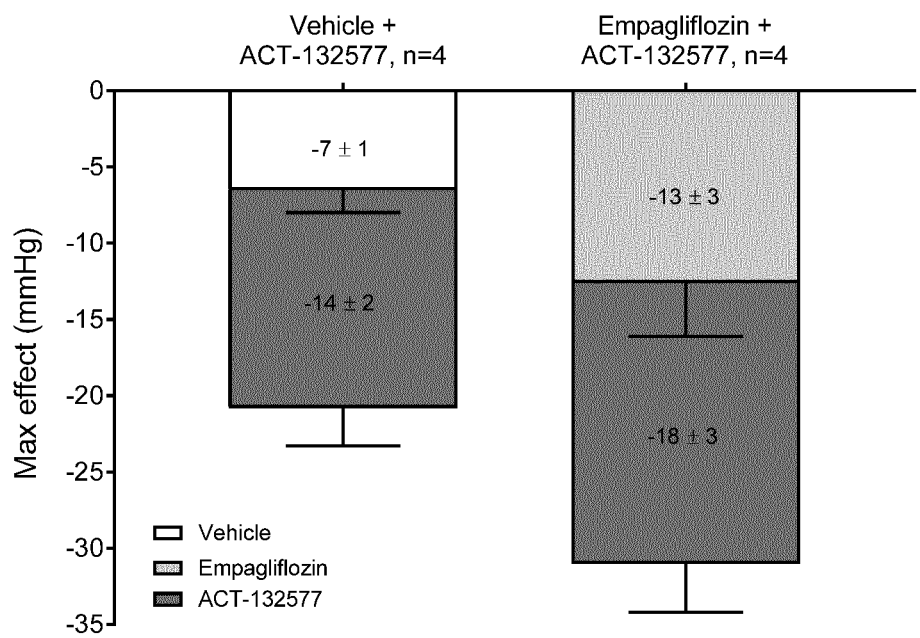

FIG. 14 shows the acute effects of ACT-132577, used alone or in combination with empagliflozin, on maximal effects on MAP in conscious, male spontaneaously hypertensive rats.

Figure 15:
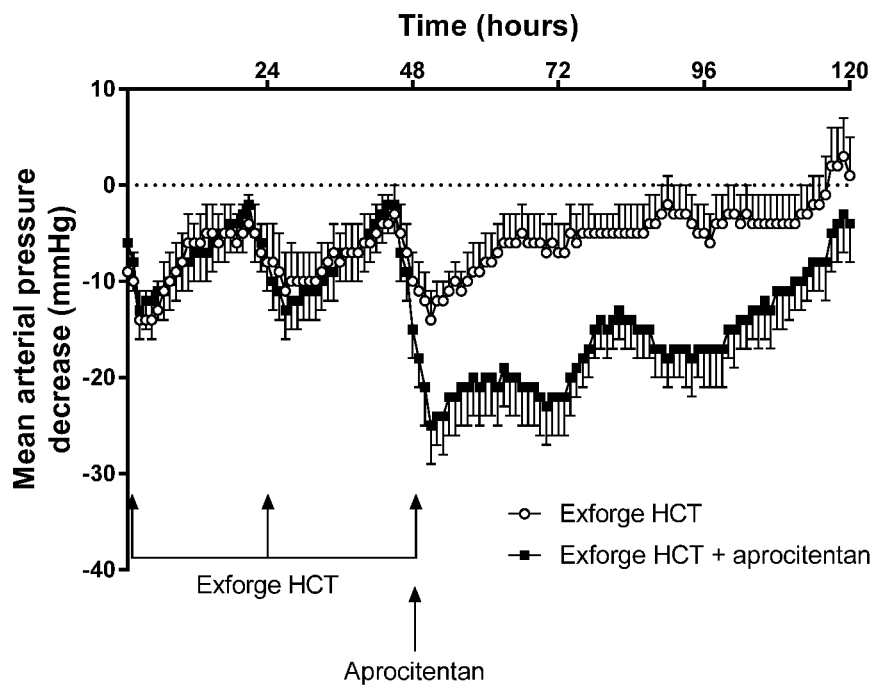

FIG. 15 shows acute effects of EXFORGE HCT® alone, and EXFORGE HCT® in combination with ACT-132577, in male spontaneaously hypertensive rats.

Figure 16:
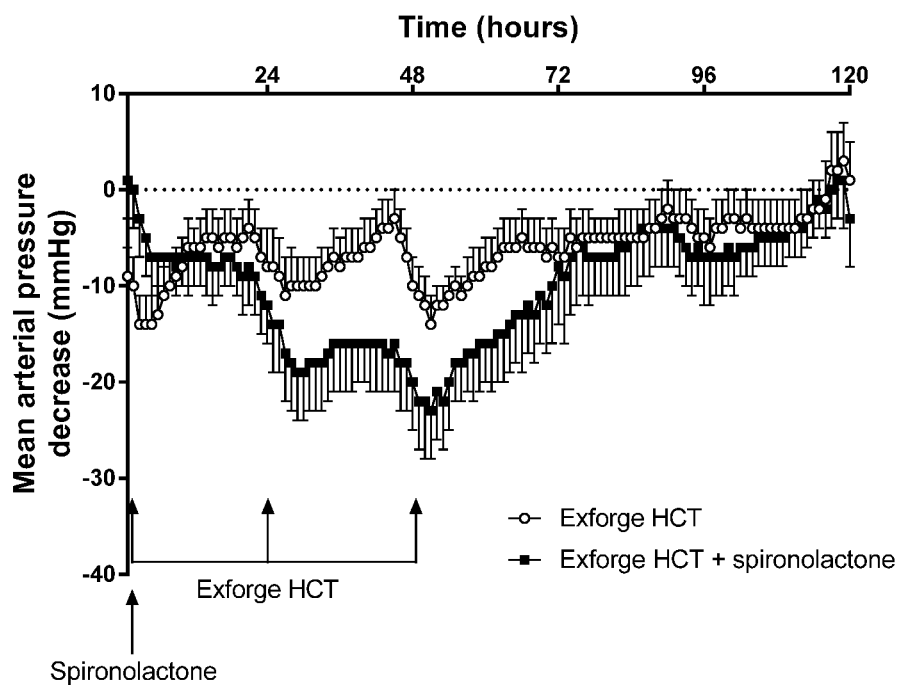

FIG. 16 shows acute effects of EXFORGE HCT® alone, and EXFORGE HCT® in combination with spironolactone, in male spontaneaously hypertensive rats.

Figure 17:
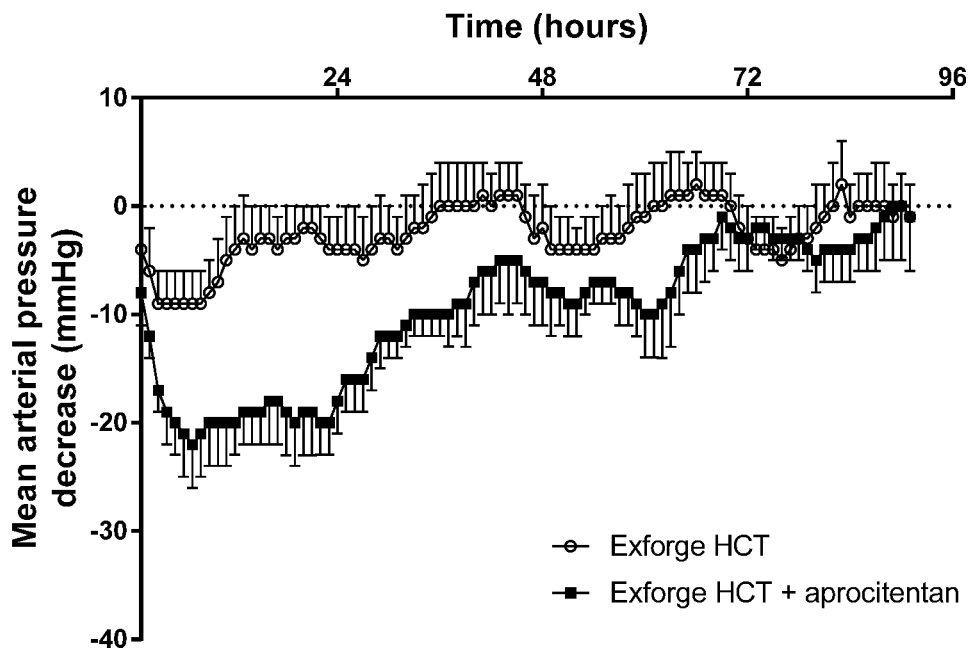

FIG. 17 shows acute effects of EXFORGE HCT® alone, and EXFORGE HCT® in combination with ACT-132577, in male hypertensive deoxycorticosterone acetate salt rats.

Figure 18:
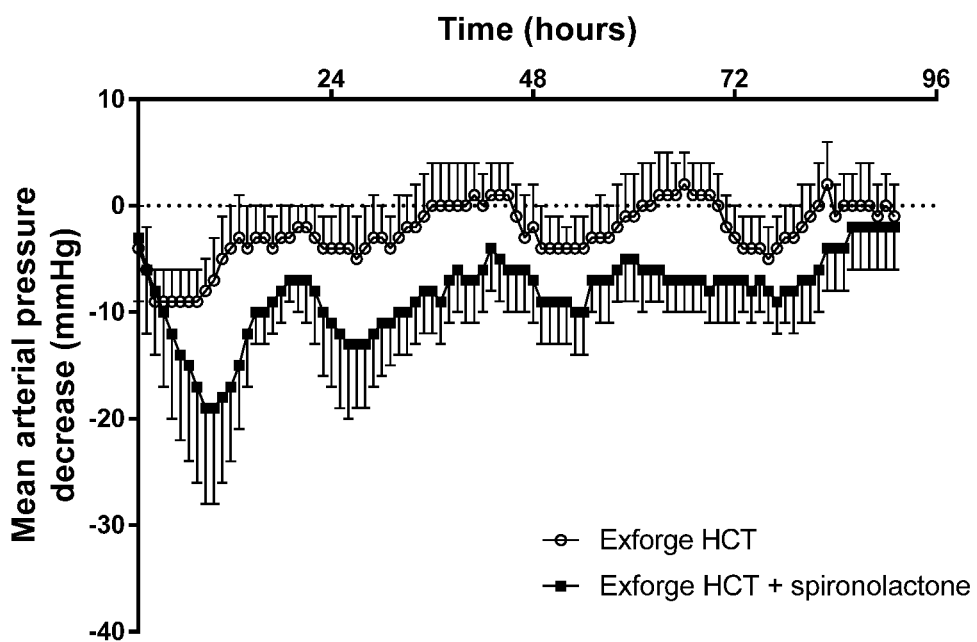

FIG. 18 shows acute effects of EXFORGE HCT® alone, and EXFORGE HCT® in combination with spironolactone, in male hypertensive deoxycorticosterone acetate salt rats.

DETAILED DESCRIPTION OF THE INVENTION

1) A first embodiment relates to a pharmaceutical composition containing, as active principles, aprocitentan, or a pharmaceutically acceptable salt thereof, in combination with an SGLT-2 inhibitor, or a pharmaceutically acceptable salt thereof, as well as at least one pharmaceutically acceptable excipient.

2) A further embodiment relates to a pharmaceutical composition according to embodiment 1), wherein the SGLT-2 inhibitor is atigliflozin, bexagliflozin, canagliflozin, dapagliflozin, empagliflozin, ertugliflozin, henagliflozin, ipragliflozin, luseogliflozin, remogliflozin, sotagliflozin, or tofogliflozin; or a pharmaceutically acceptable salt thereof.
2(i) In a sub-embodiment, the SGLT-2 inhibitor is notably
  bexagliflozin, canagliflozin, dapagliflozin, empagliflozin, ertugliflozin, henagliflozin, ipragliflozin, luseogliflozin, sotagliflozin, or tofogliflozin (especially canagliflozin, dapagliflozin, or empagliflozin; in particular canagliflozin); or a pharmaceutically acceptable salt thereof.

3) A further embodiment relates to a pharmaceutical composition according to embodiment 1), wherein the SGLT-2 inhibitor, or a pharmaceutically acceptable salt thereof, is canagliflozin, dapagliflozin, or empagliflozin (in particular canagliflozin), or a pharmaceutically acceptable salt thereof.

4) A further embodiment relates to a pharmaceutical composition according to embodiment 1), wherein the SGLT-2 inhibitor, or a pharmaceutically acceptable salt thereof, is canagliflozin, or a pharmaceutically acceptable salt thereof.

5) A further embodiment relates to a pharmaceutical composition according to any one of embodiments 1) to 4), wherein aprocitentan, or a pharmaceutically acceptable salt thereof, is comprised in a pharmaceutical unit dosage form suitable for the oral administration of 1 to 100 mg, preferably 2.5 to 100 mg (notably 10 to 50 mg); especially 10 mg, 12.5 mg, 20 mg, 25 mg, 30 mg, 40 mg, or 50 mg; in particular 12.5 mg, 25 mg or 50 mg; per day of aprocitentan;
5(i) wherein in a sub-embodiment said dose of aprocitentan is a dose which may be expected to be a tolerated efficacious dose of aprocitentan when given as a single therapy (for example with regard to the treatment of hypertension) (in particular such dose would be 10 to 25 mg, especially 10 mg, 12.5 mg, or 25 mg),
5(ii) wherein in another sub-embodiment said dose of aprocitentan is a dose which may be expected to be a tolerated efficacious dose or higher than a tolerated efficacious dose of aprocitentan when given as a single therapy (for example with regard to the treatment of hypertension) (in particular such dose would be 40 to 100 mg, especially 50 mg per day of aprocitentan);
5(iii) wherein in another sub-embodiment said dose of aprocitentan is a dose which may be expected to be a tolerated efficacious dose or lower than a tolerated efficacious dose of aprocitentan when given as a single therapy (for example with regard to the treatment of hypertension) (in particular such dose would be 1 mg, 2.5 mg or 5 mg per day of aprocitentan).

6) A further embodiment relates to a pharmaceutical composition according to any one of embodiments 1) to 4), wherein aprocitentan, or a pharmaceutically acceptable salt thereof, is comprised in a pharmaceutical unit dosage form suitable for the oral administration of 1 mg, 2.5 mg, 5 mg, 10 mg, 12.5 mg, 20 mg, 25 mg, 30 mg, 40 mg, or 50 mg; (especially 10 mg, 12.5 mg, 20 mg, 25 mg, 30 mg, 40 mg, or 50 mg; notably 12.5 mg, 25 mg or 50 mg) per day of aprocitentan;
6(i) wherein in a sub-embodiment aprocitentan, or a pharmaceutically acceptable salt thereof, is comprised in a pharmaceutical unit dosage form suitable for the oral administration of 12.5 mg per day of aprocitentan (i.e. a dose which may be expected to be a tolerated efficacious dose of aprocitentan when given as a single therapy (for example with regard to the treatment of hypertension));
6(ii) wherein in another sub-embodiment aprocitentan, or a pharmaceutically acceptable salt thereof, is comprised in a pharmaceutical unit dosage form suitable for the oral administration of 25 mg per day of aprocitentan (i.e. a dose which may be expected to be a tolerated efficacious dose of aprocitentan when given as a single therapy (for example with regard to the treatment of hypertension));
6(iii) wherein in another sub-embodiment aprocitentan, or a pharmaceutically acceptable salt thereof, is comprised in a pharmaceutical unit dosage form suitable for the oral administration of 50 mg per day of aprocitentan (i.e. a dose which may be expected to be a tolerated efficacious dose or higher than a tolerated efficacious dose of aprocitentan when given as a single therapy (for example with regard to the treatment of hypertension));
6(iv) wherein in another sub-embodiment aprocitentan, or a pharmaceutically acceptable salt thereof, is comprised in a pharmaceutical unit dosage form suitable for the oral administration of 10 mg per day of aprocitentan (i.e. a dose which may be expected to be a tolerated efficacious dose of aprocitentan when given as a single therapy (for example with regard to the treatment of hypertension));
6(v) wherein in another sub-embodiment aprocitentan, or a pharmaceutically acceptable salt thereof, is comprised in a pharmaceutical unit dosage form suitable for the oral administration of 5 mg per day of aprocitentan (i.e. a dose which may be expected to be a tolerated efficacious dose or lower than a tolerated efficacious dose of aprocitentan when given as a single therapy (for example with regard to the treatment of hypertension));
6(vi) wherein in another sub-embodiment aprocitentan, or a pharmaceutically acceptable salt thereof, is comprised in a pharmaceutical unit dosage form suitable for the oral administration of 2.5 mg per day of aprocitentan (i.e. a dose which may be expected to be lower than a tolerated efficacious dose of aprocitentan when given as a single therapy (for example with regard to the treatment of hypertension));
6(vii) wherein in another sub-embodiment aprocitentan, or a pharmaceutically acceptable salt thereof, is comprised in a pharmaceutical unit dosage form suitable for the oral administration of 1 mg per day of aprocitentan (i.e. a dose which may be expected to be lower than a tolerated efficacious dose of aprocitentan when given as a single therapy (for example with regard to the treatment of hypertension)).

7) A further embodiment relates to a pharmaceutical composition according to any one of embodiments 1) to 6), wherein said SGLT-2 inhibitor, or a pharmaceutically acceptable salt thereof, is comprised in a pharmaceutical unit dosage form suitable for the oral administration of said SGLT-2 inhibitor, wherein
bexagliflozin, or a pharmaceutically acceptable salt thereof, if present, is comprised in a pharmaceutical unit dosage form suitable for the oral administration of 5 to 50 mg (in particular 20 mg) per day of bexagliflozin;
canagliflozin, or a pharmaceutically acceptable salt thereof, if present, is comprised in a pharmaceutical unit dosage form suitable for the oral administration of 50 to 400 mg (in particular 50 mg, 100 mg, 150 mg, or 300 mg; notably 100 mg, or 300 mg; especially 100 mg) per day of canagliflozin;
dapagliflozin, or a pharmaceutically acceptable salt thereof, if present, is comprised in a pharmaceutical unit dosage form suitable for the oral administration of 1 to 20 mg (in particular 5 mg or 10 mg) per day of dapagliflozin;
empagliflozin, or a pharmaceutically acceptable salt thereof, if present, is comprised in a pharmaceutical unit dosage form suitable for the oral administration of 5 to 50 mg (in particular 10 mg or 25 mg) per day of empagliflozin;
ertugliflozin, or a pharmaceutically acceptable salt thereof, if present, is comprised in a pharmaceutical unit dosage form suitable for the oral administration of 2.5 to 50 mg (in particular 5 mg or 15 mg) per day of ertugliflozin;

henagliflozin, or a pharmaceutically acceptable salt thereof, if present, is comprised in a pharmaceutical unit dosage form suitable for the oral administration of 5 to 100 mg (in particular 25 mg) per day of henagliflozin;

ipragliflozin, or a pharmaceutically acceptable salt thereof, if present, is comprised in a pharmaceutical unit dosage form suitable for the oral administration of 10 to 100 mg (in particular 25 mg or 50 mg) per day of ipragliflozin;

luseogliflozin, or a pharmaceutically acceptable salt thereof, if present, is comprised in a pharmaceutical unit dosage form suitable for the oral administration of 1 to 10 mg (in particular 2.5 mg or 5 mg) per day of luseogliflozin;

sotagliflozin, or a pharmaceutically acceptable salt thereof, if present, is comprised in a pharmaceutical unit dosage form suitable for the oral administration of 50 to 500 mg (in particular 75 mg, 200 mg or 400 mg) per day of sotagliflozin, tofogliflozin, or a pharmaceutically acceptable salt thereof, if present, is comprised in a pharmaceutical unit dosage form suitable for the oral administration of 10 to 50 mg (in particular 20 mg) per day of tofogliflozin.

8) A further embodiment relates to a pharmaceutical composition according to embodiment 4), wherein aprocitentan, or a pharmaceutically acceptable salt thereof, is comprised in a pharmaceutical unit dosage form suitable for the oral administration of 1 to 100 mg, preferably 2.5 to 100 mg (notably 10 to 50 mg); especially 10 mg, 12.5 mg, 20 mg, 25 mg, 30 mg, 40 mg, or 50 mg; in particular 12.5 mg, 25 mg or 50 mg; per day of aprocitentan; and canagliflozin, or a pharmaceutically acceptable salt thereof, is comprised in a pharmaceutical unit dosage form suitable for the oral administration of 50 to 400 mg (in particular 50 mg, 100 mg, 150 mg, or 300 mg; notably 100 mg, or 300 mg; especially 100 mg) per day of canagliflozin;

8(i) wherein in a sub-embodiment aprocitentan, or a pharmaceutically acceptable salt thereof, is comprised in a pharmaceutical unit dosage form suitable for the oral administration of 12.5 mg per day of aprocitentan; and canagliflozin, or a pharmaceutically acceptable salt thereof, is comprised in a pharmaceutical unit dosage form suitable for the oral administration of 50 mg, 100 mg, 150 mg, or 300 mg (notably 100 mg, or 300 mg, especially 100 mg) per day of canagliflozin;

8(ii) wherein in another sub-embodiment aprocitentan, or a pharmaceutically acceptable salt thereof, is comprised in a pharmaceutical unit dosage form suitable for the oral administration of 25 mg per day of aprocitentan; and canagliflozin, or a pharmaceutically acceptable salt thereof, is comprised in a pharmaceutical unit dosage form suitable for the oral administration of 50 mg, 100 mg, 150 mg, or 300 mg (notably 100 mg, or 300 mg, especially 100 mg) per day of canagliflozin;

8(iii) wherein in another sub-embodiment aprocitentan, or a pharmaceutically acceptable salt thereof, is comprised in a pharmaceutical unit dosage form suitable for the oral administration of 10 mg per day of aprocitentan; and canagliflozin, or a pharmaceutically acceptable salt thereof, is comprised in a pharmaceutical unit dosage form suitable for the oral administration of 50 mg, 100 mg, 150 mg, or 300 mg (notably 100 mg, or 300 mg, especially 100 mg) per day of canagliflozin;

8(iv) wherein in another sub-embodiment aprocitentan, or a pharmaceutically acceptable salt thereof, is comprised in a pharmaceutical unit dosage form suitable for the oral administration of 5 mg per day of aprocitentan; and canagliflozin, or a pharmaceutically acceptable salt thereof, is comprised in a pharmaceutical unit dosage form suitable for the oral administration of 50 mg, 100 mg, 150 mg, or 300 mg (notably 100 mg, or 300 mg, especially 100 mg) per day of canagliflozin;

8(v) wherein in another sub-embodiment aprocitentan, or a pharmaceutically acceptable salt thereof, is comprised in a pharmaceutical unit dosage form suitable for the oral administration of 2.5 mg per day of aprocitentan; and canagliflozin, or a pharmaceutically acceptable salt thereof, is comprised in a pharmaceutical unit dosage form suitable for the oral administration of 50 mg, 100 mg, 150 mg, or 300 mg (notably 100 mg, or 300 mg, especially 100 mg) per day of canagliflozin;

8(vi) wherein in another sub-embodiment aprocitentan, or a pharmaceutically acceptable salt thereof, is comprised in a pharmaceutical unit dosage form suitable for the oral administration of 1 mg per day of aprocitentan; and canagliflozin, or a pharmaceutically acceptable salt thereof, is comprised in a pharmaceutical unit dosage form suitable for the oral administration of 50 mg, 100 mg, 150 mg, or 300 mg (notably 100 mg, or 300 mg, especially 100 mg) per day of canagliflozin;

8(vii) wherein in another sub-embodiment aprocitentan, or a pharmaceutically acceptable salt thereof, is comprised in a pharmaceutical unit dosage form suitable for the oral administration of 50 mg per day of aprocitentan; and canagliflozin, or a pharmaceutically acceptable salt thereof, is comprised in a pharmaceutical unit dosage form suitable for the oral administration of 50 mg, 100 mg, 150 mg, or 300 mg (notably 100 mg, or 300 mg, especially 100 mg) per day of canagliflozin.

Likewise, when combined with dapagliflozin or empagliflozin, aprocitentan, or a pharmaceutically acceptable salt thereof, is comprised as set out in embodiment 8) and its sub-embodiments 8(i) to 8(vii) above; and dapagliflozin, or a pharmaceutically acceptable salt thereof, if present, is comprised in a pharmaceutical unit dosage form suitable for the oral administration of 1 to 20 mg (in particular 5 mg or 10 mg) per day of dapagliflozin; and empagliflozin, or a pharmaceutically acceptable salt thereof, if present, is comprised in a pharmaceutical unit dosage form suitable for the oral administration of 5 to 50 mg (in particular 10 mg or 25 mg) per day of empagliflozin.

9) A second aspect of the present invention relates to a pharmaceutical composition according to any one of embodiments 1) to 8); wherein said pharmaceutical composition is (intended) to be administered in combination/co-therapy to conventional background therapy (or first line therapy) suitable for the prevention or treatment of hypertension including especially difficult to treat/resistant hypertension; chronic kidney disease (CKD) [notably CKD of stages 1 to 4 as defined by the Kidney Disease Improving Global Outcomes (KDIGO) Guidelines (and especially CKD of stage 3)], and in particular CKD (notably of these stages) caused by/associated with hypertension and/or caused by/associated with diabetes (diabetic kidney disease (DKD)); or diabetes.

9(i) In a first sub-embodiment, such conventional background therapy may notably comprise:
- an ACE inhibitor (especially enalapril, as well as ramipril, quinapril, perindopril, lisinopril, benazepril, imidapril, trandolapril, cilazapril), or a pharmaceutically acceptable salt thereof; and/or
- an angiotenin receptor blocker (especially valsartan, as well as losartan, candesartan, irbesartan, telmisartan, eprosartan, olmesartan, azilsartan, fimasartan), or a pharmaceutically acceptable salt thereof; and/or
- a calcium channel blocker (especially amlodipine, as well as aranidipine, azelnidipine, barnidipine, benidipine, cilnidipine, clevidipine, efonidipine, felodipine, isradipine, lacidipine, lercanidipine, manidipine, nicardipine, nifedipine, nilvadipine, nimodipine, nisoldipine, nitrendipine, pranidipine), or a pharmaceutically acceptable salt thereof; and/or
- metformin; and/or
- insulin; and/or
- a sulfonylurea (especially glibenclamide), or a pharmaceutically acceptable salt thereof; and/or
- a DPP-4 inhibitor (especially sitagliptin, vildagliptin, saxagliptin, or linagliptin), or a pharmaceutically acceptable salt thereof; and/or
- a GLP-1 receptor agonist (especially exenatide, liraglutide, lixisenatide, albiglutide, dulaglutide, taspoglutide, semaglutide); and/or
- a thiazolidinedione, or a pharmaceutically acceptable salt thereof.

9(ii) In second sub-embodiment, preferred are conventional background therapies which are first line therapies suitable for the prevention or treatment of hypertension and/or diabetes, such as especially an ACE inhibitor or an angiotenin receptor blocker as hypertension treatments; and/or metformin, and/or a DPP-4 inhibitor as diabetes treatment.

9(iii) In third sub-embodiment, said background therapy according to any one of embodiments 9), 9(i), or 9(ii) is to be administered in a dosage corresponding to a tolerated efficacious dose of the respective active ingredient, e.g. when given as a single therapy, or in diabetes patients, when given in combination with the respective SGLT-2 inhibitor. In particular, valsartan, or a pharmaceutically acceptable salt thereof, if present, is to be administered in a dosage form suitable for the oral administration of 160 mg or 320 mg per day of valsartan; losartan, or a pharmaceutically acceptable salt thereof, if present, is to be administered in a dosage form suitable for the oral administration of 50 mg or 100 mg per day of losartan; irbesartan, or a pharmaceutically acceptable salt thereof, if present, is to be administered in a dosage form suitable for the oral administration of 75 mg, 150 mg, or 300 mg per day of irbesartan; amlodipine, or a pharmaceutically acceptable salt thereof, if present, is to be administered in a dosage form suitable for the oral administration of 5 mg or 10 mg per day of amlodipine; enalapril, or a pharmaceutically acceptable salt thereof, if present, is to be administered in a dosage form suitable for the oral administration of 2.5 mg to 40 mg per day of enalapril; lisinopril, or a pharmaceutically acceptable salt thereof, if present, is to be administered in a dosage form suitable for the oral administration of 2.5 mg to 40 mg per day of lisinopril; ramipril, or a pharmaceutically acceptable salt thereof, if present, is to be administered in a dosage form suitable for the oral administration of 2.5 mg to 20 mg per day of ramipril; metformin, if present, is to be administered in a dosage form suitable for the oral administration of 500 mg to 2000 mg per day of metformin; glibenclamide if present, is to be administered in a dosage form suitable for the oral administration of 1.25 mg to 5 mg per day of glibenclamide; sitagliptin if present, is to be administered in a dosage form suitable for the oral administration of 25 mg to 100 mg per day of sitagliptin; vildagliptin if present, is to be administered in a dosage form suitable for the oral administration of two times 50 mg per day of vildagliptin; saxagliptin if present, is to be administered in a dosage form suitable for the oral administration of 2.5 mg or 5 mg per day of saxagliptin; linagliptin if present, is to be administered in a dosage form suitable for the oral administration of two times 5 mg per day of linagliptin.

"Angiotensin Receptor Blocker" or "ARB" in particular means in the present application valsartan, losartan, telmisartan, irbesartan, candesartan, olmesartan, azilsartan, or a pharmaceutically acceptable salt of one of these. A preferred ARB is valsartan or a pharmaceutically acceptable salt thereof.

"Calcium Channel Blocker" or "CCB" in particular means in the present application amlodipine, aranidipine, azelnidipine, barnidipine, benidipine, cilnidipine, clevidipine, isradipine, efonidipine, felodipine, lacidipine, lercanidipine, manidipine, nicardipine, nifedipine, nilvadipine, nimodipine, nisoldipine, nitrendipine, pranidipine, verapamil or diltiazem or a pharmaceutically acceptable salt of one of these. A preferred CCB is amlodipine or a pharmaceutically acceptable salt thereof.

"Angiotensin Converting Enzyme inhibitor" or "ACE inhibitor" in particular means in the present application captopril, enalapril, ramipril, quinapril, perindopril, lisinopril, imidapril or cilazapril, or a pharmaceutically acceptable salt of one of these. A preferred ACE inhibitor is enalapril, or a pharmaceutically acceptable salt thereof.

The term "DPP-4 inhibitor" or "DPP-IV inhibitor" refers to inhibitors of dipeptidyl peptidase 4 such as especially sitagliptin, vildagliptin, saxagliptin, and linagliptin, as well as gemigliptin, anagliptin, teneligliptin, alogliptin, trelagliptin, omarigliptin, evogliptin, and dutogliptin.

The term "GLP-1 receptor agonist" refers to agonists of the glucagon-like peptide-1 receptor such as especially exenatide, liraglutide, lixisenatide, albiglutide, dulaglutide, taspoglutide, semaglutide.

The term "sulfonylurea" refers especially to glibenclamide (glyburide), glibornuride, gliclazide, glipizide, gliquidone, glisoxepide, glyclopyramide, or glimepiride.

The term "thiazolidinediones" abbreviated as TZD, also known as glitazones, refers to agonists of the PPARγ (peroxisome proliferator-activated receptor gamma), and refers especially to pioglitazone, rosiglitazone, or lobeglitazone.

A further conventional background therapy, in particular for the treatment of a patient having a history of hypertension, may be a diuretic. Such diuretic may especially be prescribed in addition to the above-mentioned conventional background therapies of hypertension. The term "diuretic" in the present application refers to loop diuretics including furosemide, bumetanide, ethacrynic acid, torsemide; potassium-sparing diuretics including aldosterone antagonists such as spironolactone, eplerenone, or finerenone, or aldosterone synthase inhibitors; carbonic anhydrase inhibitors including acetazolamide and methazolamide; and in particular to diuretics of the thiazide class (thiazide-like diuretics) such as especially chlorthalidone, hydrochlorothiazide, chlorothiazide, indapamide, or metolazone. Preferred thiazide-like diuretic are chlorthalidone or hydrochlorothiazide. For avoidance of doubt, even though having a diuretic pharmacological effect, SGLT-2 inhibitors are not encompassed in the term "diuretic" as used herein.

10) A third aspect of the invention relates to a pharmaceutical composition according to any one of embodiments 1) to 9), said composition comprising aprocitentan in crystalline Form A characterized by the presence of peaks in the X-ray powder diffraction diagram at the following angles of refraction 2θ: 17.8°, 20.0°, and 23.5°; wherein said X-ray powder diffraction diagram is obtained by using combined Cu Kα1 and Kα2 radiation, without Kα2 stripping; and the accuracy of the 2θ values is in the range of 2θ+/−0.2°.

11) A further embodiment relates to a pharmaceutical composition according to any one of embodiments 1) to 9), said composition comprising aprocitentan in crystalline Form A characterized by the presence of peaks in the X-ray powder diffraction diagram at the following angles of refraction 2θ: 17.8°, 18.6°, 20.0°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°.

12) A further embodiment relates to a pharmaceutical composition according to any one of embodiments 1) to 9), said composition comprising aprocitentan in crystalline Form A characterized by the presence of peaks in the X-ray powder diffraction diagram at the following angles of refraction 2θ: 9.8°, 9.9°, 11.7°, 17.8°, 18.6°, 20.0°, 21.5°, 22.8°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°.

13) A further embodiment relates to a pharmaceutical composition according to any one of embodiments 1) to 9), said composition comprising aprocitentan in crystalline Form A characterized by the presence of peaks in the X-ray powder diffraction diagram at the following angles of refraction 2θ: 9.8°, 9.9°, 11.7°, 14.5°, 15.4°, 15.6°, 16.9°, 17.2°, 17.8°, 18.6°, 19.9°, 20.0°, 21.5°, 21.9°, 22.8°, 23.2°, 23.5°, 24.9°, 25.1°, 25.3°, 25.6°, 25.9°, 27.1°, 27.3°, 28.5°, 29.0°, 29.4°, 30.1° and 30.6°; wherein said X-ray powder diffraction diagram is obtained by using combined Cu Kα1 and Kα2 radiation, without Kα2 stripping; and the accuracy of the 20 values is in the range of 2θ+/−0.2°.

14) A further embodiment relates to a pharmaceutical composition according to any one of embodiments 1) to 9), said composition comprising aprocitentan in crystalline Form A characterized by the presence of peaks in the X-ray powder diffraction diagram at the following angles of refraction 2θ: 9.8° (18%), 9.9° (18%), 11.7° (14%), 14.5° (10%), 15.4° (14%), 15.6° (29%), 16.9° (19%), 17.2° (16%), 17.8° (100%), 18.6° (50%), 19.9° (54%), 20.0° (67%), 21.5° (24%), 21.9° (10%), 22.8° (18%), 23.2° (49%), 23.5° (83%), 24.9° (32%), 25.1° (20%), 25.3° (24%), 25.6° (33%), 25.9° (16%), 27.1° (23%), 27.3° (39%), 28.5° (13%), 29.0° (23%), 29.4° (15%), 30.1° (12%) and 30.6° (10%); wherein said X-ray powder diffraction diagram is obtained by using combined Cu Kα1 and Kα2 radiation, without Kα2 stripping; and the accuracy of the 2θ values is in the range of 2θ+/−0.2°.

The present data show peaks having a relative intensity, as compared to the most intense peak in the diagram, of the following percentages (relative peak intensitites given in parentheses) at the indicated angles of refraction 2theta (selected peaks from the range 3-33° 2theta with relative intensity larger then 10% are reported).

15) A further embodiment relates to a pharmaceutical composition according to any one of embodiments 1) to 9), said composition comprising aprocitentan in crystalline Form A which essentially shows the X-ray powder diffraction pattern as depicted in FIG. 1, wherein said X-ray powder diffraction diagram is obtained by using combined Cu Kα1 and Kα2 radiation, without Kα2 stripping; and the accuracy of the 2θ values is in the range of 2θ+/−0.2°.

In this context the term "essentially" means that at least the major peaks of the diagram depicted in said figures, i.e. those having a relative intensity of more than 10%, especially more than 20%, as compared to the most intense peak in the diagram, have to be present. However, the person skilled in the art of X-ray powder diffraction will recognize that relative intensities in X-ray powder diffraction diagrams may be subject to strong intensity variations due to preferred orientation effects.

16) A further embodiment relates to a pharmaceutical composition according to any one of embodiments 1) to 9), said composition comprising aprocitentan in crystalline Form A obtainable by crystallisation of the COMPOUND in an aqueous solution at pH 6.2 to 6.8.

For avoidance of any doubt, whenever one of the above embodiments refers to "peaks in the X-ray powder diffraction diagram at the following angles of refraction 2θ", said X-ray powder diffraction diagram is obtained by using combined Cu Kα1 and Kα2 radiation, without Kα2 stripping; and it should be understood that the accuracy of the 2θ values as provided herein is in the range of +/−0.1-0.2°. Notably, when specifying an angle of refraction 2theta (2θ) for a peak in the invention embodiments and the claims, the 2θ value given is to be understood as an interval from said value minus 0.2° to said value plus 0.2° (2θ+/−0.2°); and preferably from said value minus 0.1° to said value plus 0.1° (2θ+/−0.1°).

When defining the presence of peak in e.g. an X-ray powder diffraction diagram, a common approach is to do this in terms of the S/N ratio (S=signal, N=noise). According to this definition, when stating that a peak has to be present in an X-ray powder diffraction diagram, it is understood that the peak in the X-ray powder diffraction diagram is defined by having an S/N ratio (S=signal, N=noise) of greater than x (x being a numerical value greater than 1), usually greater than 2, especially greater than 3.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., preferably to an interval extending from Y minus 5° C. to Y plus 5° C., notably to an interval extending from Y minus 3° C. to Y plus 3° C. Room temperature means a temperature of about 25° C. When in the current application the term n equivalent(s) is used wherein n is a number, it is meant and within the scope of the current application that n is referring to about the number n, preferably n is referring to the exact number n.

Whenever the word "between" or "to" is used to describe a numerical range, it is to be understood that the end points of the indicated range are explicitly included in the range. For example: if a temperature range is described to be between 40° C. and 80° C. (or 40° C. to 80° C.), this means that the end points 40° C. and 80° C. are included in the range; or if a variable is defined as being an integer between 1 and 4 (or 1 to 4), this means that the variable is the integer 1, 2, 3, or 4.

17) A fourth aspect of the invention relates to a pharmaceutical composition according to any one of embodiments 1) to 9), said composition comprising aprocitentan in crystalline Form C characterized by the presence of peaks in the X-ray powder diffraction diagram at the following angles of refraction 2θ: 9.7°, 15.7°, and 22.0°; wherein said X-ray powder diffraction diagram is obtained by using combined Cu Kα1 and Kα2 radiation, without Kα2 stripping; and the accuracy of the 2θ values is in the range of 2θ+/−0.2°.

18) A further embodiment relates to a pharmaceutical composition according to any one of embodiments 1) to 9), said composition comprising aprocitentan in crystalline Form C characterized by the presence of peaks in the X-ray powder diffraction diagram at the following angles of refraction 2θ: 7.8°, 9.7°, 15.7°, 19.8° and 22.0°; wherein said X-ray powder diffraction diagram is obtained by using combined Cu Kα1 and Kα2 radiation, without Kα2 stripping; and the accuracy of the 2θ values is in the range of 2θ+/−0.2°.

19) A further embodiment relates to a pharmaceutical composition according to any one of embodiments 1) to 9), said composition comprising aprocitentan in crystalline Form C characterized by the presence of peaks in the X-ray powder diffraction diagram at the following angles of refraction 2θ: 7.8°, 9.7°, 15.7°, 17.2°, 17.8°, 18.8°, 19.8°, 22.0°, 23.6°, and 25.3°; wherein said X-ray powder diffraction diagram is obtained by using combined Cu Kα1 and Kα2 radiation, without Kα2 stripping; and the accuracy of the 2θ values is in the range of 2θ+/−0.2°.

20) A further embodiment relates to a pharmaceutical composition according to any one of embodiments 1) to 9), said composition comprising aprocitentan in crystalline Form C characterized by the presence of peaks in the X-ray powder diffraction diagram at the following angles of refraction 2θ: 7.8°, 9.7°, 15.7°, 17.2°, 17.8°, 18.8°, 19.8°, 20.1°, 20.6°, 21.6°, 22.0°, 23.4°, 23.6°, 24.1°, 24.5°, 25.1°, 25.3°, 25.7°, 26.8°, 27.1°, 28.5°, 30.8° and 30.8°; wherein said X-ray powder diffraction diagram is obtained by using combined Cu Kα1 and Kα2 radiation, without Kα2 stripping; and the accuracy of the 2θ values is in the range of 2θ+/−0.2°.

21) A further embodiment relates to a pharmaceutical composition according to any one of embodiments 1) to 9), said composition comprising aprocitentan in crystalline Form C characterized by the presence of peaks in the X-ray powder diffraction diagram at the following angles of refraction 2θ: 7.8° (23%), 9.7° (42%), 15.7° (37%), 17.2° (16%), 17.8° (15%), 18.8° (26%), 19.8° (71%), 20.1° (51%), 20.6° (15%), 21.6° (15%), 22.0° (100%), 23.4° (27%), 23.6° (40%), 24.1° (23%), 24.5° (16%), 25.1° (13%), 25.3° (39%), 25.7° (28%), 26.8° (19%), 27.1° (16%), 28.5° (31%), 30.8° (13%) and 30.8° (13%); wherein said X-ray powder diffraction diagram is obtained by using combined Cu Kα1 and Kα2 radiation, without Kα2 stripping; and the accuracy of the 2θ values is in the range of 2θ+/−0.2°.

The present data show peaks having a relative intensity, as compared to the most intense peak in the diagram, of the following percentages (relative peak intensitites given in parentheses) at the indicated angles of refraction 2theta (selected peaks from the range 3-33° 2theta with relative intensity larger then 10% are reported).

22) A further embodiment relates to a pharmaceutical composition according to any one of embodiments 1) to 9), said composition comprising aprocitentan in crystalline Form C which essentially shows the X-ray powder diffraction pattern as depicted in FIG. 3, wherein said X-ray powder diffraction diagram is obtained by using combined Cu Kα1 and Kα2 radiation, without Kα2 stripping; and the accuracy of the 2θ values is in the range of 2θ+/−0.2°.

In this context the term "essentially" means that at least the major peaks of the diagram depicted in said figures, i.e. those having a relative intensity of more than 10%, especially more than 20%, as compared to the most intense peak in the diagram, have to be present. However, the person skilled in the art of X-ray powder diffraction will recognize that relative intensities in X-ray powder diffraction diagrams may be subject to strong intensity variations due to preferred orientation effects.

23) A further embodiment relates to a pharmaceutical composition according to any one of embodiments 1) to 9), said composition comprising aprocitentan in crystalline Form C obtainable by crystallisation of the COMPOUND from MeOH, EtOH or propan-2-ol.

24) A further embodiment relates to a pharmaceutical composition according to any one of embodiments 1) to 9), said composition comprising aprocitentan in amorphous form. Such amorphous form may be obtained by milling form A. For Example, the amorphous form is obtainable by milling in a ball mill (MM200 Retsch Ball Mill, 2 agate beads), 30 min at 30 Hz at ambient temperature.

The production of the pharmaceutical compositions can be effected in a manner which will be familiar to any person skilled in the art (see for example Remington, The Science and Practice of Pharmacy, 21st Edition (2005), Part 5, "Pharmaceutical Manufacturing" [published by Lippincott Williams & Wilkins]) by bringing the crystalline forms of the present invention, optionally in combination with other therapeutically valuable substances, into a galenical administration form together with suitable, non-toxic, inert, pharmaceutically acceptable solid or liquid carrier materials and, if desired, usual pharmaceutical adjuvants.

25) A further embodiment relates to a solid pharmaceutical composition (in particular in the form of a tablet) according to any one of embodiments 1) to 24), especially according to any one of embodiments 10) to 16), or according to any one of embodiments 17) to 22), comprising as pharmaceutically acceptable excipient inert microcrystalline cellulose, lactose, hydroxypropylcellulose, croscarmellose sodium and magnesium stearate.

26) Especially, the solid pharmaceutical composition of embodiment 25) will comprise aprocitentan in a total amount from 5 to 25% in weight based on the total weight of the pharmaceutical composition, microcrystalline cellulose in a total amount from 20 to 30% in weight based on the total weight of the pharmaceutical composition, lactose in a total amount from 40 to 65% in weight based on the total weight of the pharmaceutical composition, hydroxypropylcellulose in a total amount from 1 to 3% in weight based on the total weight of the pharmaceutical composition, croscarmellose sodium in a total amount from 2 to 8% in weight based on the total weight of the pharmaceutical composition and magnesium stearate in a total amount from 0.2 to 2% in weight based on the total weight of the pharmaceutical composition, whereby the total percent in weight of the solid pharmaceutical composition will always be 100; the aforementioned solid pharmaceutical composition will particularly be in the form of a tablet.

27) A further embodiment of the invention relates to a pharmaceutical composition according to embodiments 25) or 26), wherein said pharmaceutical composition is in form of a tablet. In a sub-embodiment, the pharmaceutically active ingredients are comprised in granules prior to compression to said tablet.

A tablet according to embodiment 27) can optionally be coated with a suitable protective pellicle. Said protective pellicle will notably prevent direct contact of the pharmaceutical composition with moisture; it may also ease imprints that may be desired to be used in order to distinguish the pharmaceutical composition from others.

The coating material for making such protective pellicle may include a low water vapour permeability polymer (such as a polyvinyl alcohol (e.g. Aquapolish® white PVA from manufacturer Biogrund) or dimethylaminoethyl methacrylate (e.g. EUDRAGIT® E PO)). The coating material can further include a plasticizing agent (e.g. propylene glycol, triacetyne, dibutyl phthalate or dibutyl sebacate), a surfactant (e.g. sodium lauryl sulphate or a polysorbate such as Tween) and/or a lubricant/glidant (e.g. stearic acid, magnesium or calcium stearate or talc). Moreover, the coating material can also include a pigment (e.g. iron(II) oxide, iron(III) oxide or titanium oxide) to give the tablet a coloured aspect.

28) A further embodiment of the invention relates to a pharmaceutical composition according to any one of embodiments 25) to 26), wherein said pharmaceutical composition is in form of a capsule. In a sub-embodiment, the pharmaceutically active ingredients are comprised in granules prior to filling into said capsules.

For avoidance of any doubt, the invention further relates to the crystalline forms of aprocitentan, especially to crystalline form A, disclosed herein wherein such crystalline form is suitable/is used as final isolation step of aprocitentan (e.g. in order to meet the purity requirements of pharmaceutical production), whereas the final pharmaceutical composition according to embodiments 1 to 28) may or may not contain said crystalline form (e.g. because the originally crystalline form of aprocitentan is further transformed during the manufacturing process and/or is dissolved in the pharmaceutically acceptable carrier material(s); thus, in the final pharmaceutical composition, aprocitentan may be present in non-crystalline form, in another crystalline form, or in dissolved form, or the like).

Such combination pharmaceutical compositions according to embodiments 1) to 28) are especially useful for the treatment of endothelin related diseases and in a method for the treatment of endothelin related diseases in a subject in need for an ERA.

Such endothelin related diseases may in particular be defined as including hypertension including especially difficult to treat/resistant hypertension; ischemic heart diseases including angina pectoris, coronary diseases, and myocardial ischemia; cardiac insufficiency; chronic kidney disease (CKD) [especially CKD of stages 1 to 4 as defined by the Kidney Disease Improving Global Outcomes (KDIGO) Guidelines (and notably CKD of stage 3)], and in particular CKD (notably of these stages) caused by/associated with hypertension, or caused by/associated with diabetes (also referred to as diabetic kidney disease (DKD), wherein especially such diabetes is type 2 diabetes); diabetes, and diabetes related diseases such as diabetic arteriopathy, diabetic nephropathy, diabetic retinopathy, or diabetic vasculopathy; reducing the risk of developing a major cardiovascular event (such as HF, myocardial infarction, stroke, or death from cardiovascular causes) in patients who have diabetes, especially in patients who have diabetes that is accompanied by at least one other cardiovascular risk factor (such as especially hypertension); therapy and prophylaxis of diabetic complications; (acute and chronic) renal failure; glomerulonephritis; connective tissue diseases; atherosclerosis; peripheral arterial obliterant disease including chronic peripheral arteriopathy; digital ulcers; diabetic foot ulcers and/or reducing the risk of lower extremety/limb amputations in patients who have diabetes; heart failure (HF) defined as including especially chronic HF, including in particular systolic HF/HF with reduced ejection fraction (HFrEF) (i.e. ejection fraction<about 40%), and diastolic HF/HF with preserved ejection fraction (HFpEF) (i.e. ejection fraction>about 50%); reducing the risk of developing a major cardiovascular event (such as HF, myocardial infarction, stroke, or death from cardiovascular causes) in patients who are at cardiovascular risk (such as patients who have coronary artery disease and/or patients who have demonstrated clinical signs of congestive HF); and diastolic dysfunction.

For avoidance of doubt, the term CKD caused by/associated with diabetes (diabetic kidney disease, DKD) may also include such DKD associated, in addition, with hypertension; wherein especially the diabetes is type 2 diabetes.

Especially, in the context of the present invention, endothelin related diseases include chronic kidney disease (CKD) [especially CKD of stages 1 to 4 as defined by the Kidney Disease Improving Global Outcomes (KDIGO) Guidelines (and notably CKD of stage 3)], and in particular CKD (notably of these stages) caused by/associated with hypertension, and/or caused by/associated with diabetes (diabetic kidney disease (DKD)); as well as (acute and chronic) renal failure; diabetic nephropathy; and glomerulonephritis;

in a sub-embodiment, DKD as defined before especially refers to DKD in a patient diagnosed with type 2 diabetes mellitus; in particular to the reduction of the rate of progression of DKD e.g. in a patient diagnosed with type 2 diabetes mellitus, wherein such reduced rate of progression may especially be expressed by a reduction in eGFR, a reduction of events of end-stage kidney disease (ESKD), or a reduction of events of renal death; wherein especially said patient presents in addition a history of hypertension;

in a further sub-embodiment, DKD as defined before especially refers to diabetic nephropathy associated with an elevated serum creatinine and/or proteinuria [especially corresponding to CKD of stages 1 to 4 as defined by the Kidney Disease Improving Global Outcomes (KDIGO) Guidelines (and notably to CKD of stage 3)] in patients with type 2 diabetes, especially in such patients presenting in addition a history of hypertension;

in a further sub-embodiment, DKD as defined before especially refers to such DKD associated, in addition, with hypertension; wherein especially the diabetes is type 2 diabetes;

diabetes, and diabetes related diseases such as diabetic arteriopathy, diabetic retinopathy, or diabetic vasculopathy; as well as therapy and prophylaxis of diabetic complications; and reducing the risk of developing a major cardiovascular event (such as HF, myocardial infarction, stroke, or death from cardiovascular causes) in patients who have diabetes, especially in patients who have diabetes that is accompanied by at least one other cardiovascular risk factor (such as especially hypertension); as well as diabetic foot ulcers and/or reducing the risk of lower extremety amputations in patients who have diabetes; and heart failure (HF) defined as including especially chronic HF, including in particular systolic HF/HF with reduced ejection fraction (HFrEF) (i.e. ejection fraction<about 40%), and diastolic HF/HF with preserved ejection fraction (HFpEF) (i.e. ejection fraction>about 50%); as well as reducing the risk of developing a major cardiovascular event (such as HF, myocardial infarction, stroke, or death from cardiovascular causes) in patients who are at cardiovascular risk (such as patients who have coronary artery disease and/or patients who have demonstrated clinical signs of congestive HF); angina pectoris; coronary diseases; cardiac insufficiency; and diastolic dysfunction.

Essential hypertension (also called primary hypertension or idiopathic hypertension) is the form of hypertension that by definition has no identifiable cause. It represents a significant global public health concern, contributing to vascular and renal morbidity and to cardiovascular mortality. The diagnosis of essential hypertension is made when the average of multiple systolic blood pressure measurements on 2 or more subsequent visits is consistently equal to or above a certain threshold value $T_{SBP}$. Individuals with high normal blood pressure tend to maintain pressures that are above average for the general population and are at greater risk for development of definite hypertension and cardiovascular events than the general population. The threshold value $T_{SBP}$ above which treatment is recommended is regularly discussed among clinicians (see e.g. Mancia et al, *J. Hypertens.* (2013), 31, 1281-1357); accordingly, depending on the patient's general condition and age, $T_{SBP}$ could be 140 or 130 mm Hg, or another suitable value.

The term "resistant hypertension" [equivalent to the term "difficult to treat hypertension"] in the present invention is defined as blood pressure that remains above goal in spite of the concurrent use of three antihypertensive agents of different classes. One of the three therapeutic agents should be a diuretic and all agents should be prescribed at optimal/maximal dose amounts. As defined, resistant hypertension patients include patients whose blood pressure is controlled with use of more than three medications. That is, patients whose blood pressure is controlled but require four or more medications to do so should be considered resistant to treatment (see e.g. Mancia et al, *J. Hypertens.* (2013), 31, 1281-1357).

The term "diabetes" as used herein refers to all types of diabetes, especially to type 2 diabetes; as well as type 1 diabetes and latent autoimmune diabetes of adulthood, a form of diabetes mellitus type 1 that occurs in adulthood, often with a slower course of onset than type 1 diabetes diagnosed in juveniles.

29) A fifth aspect of the invention, thus, relates to aprocitentan, or a pharmaceutically acceptable salt thereof,
  for use in the prophylaxis/prevention or treatment of CKD [especially CKD of stages 1 to 4, notably CKD of stage 3]; and in particular CKD (notably of these stages) caused by/associated with hypertension, and/or caused by/associated with diabetes (DKD); as well as in the prophylaxis/prevention or treatment of acute or chronic renal failure; diabetic nephropathy; or glomerulonephritis;
  wherein, in a first sub-embodiment, such use is especially for the treatment of such DKD in a patient diagnosed with type 2 diabetes mellitus, wherein in particular aprocitentan reduces the rate of progression of DKD, wherein such reduced rate of progression may especially be expressed by a reduction in eGFR, a reduction of events of end-stage kidney disease (ESKD), or a reduction of events of renal death; wherein notably said patient presents in addition a history of hypertension;
  wherein, in a second sub-embodiment, such use is especially for the treatment of such DKD, including treatment of diabetic nephropathy associated with an elevated serum creatinine and/or proteinuria [especially corresponding to CKD of stages 1 to 4 as defined by the Kidney Disease Improving Global Outcomes (KDIGO) Guidelines (and notably to such CKD of stage 3)], in patients with type 2 diabetes, especially in such patients presenting in addition a history of hypertension;
  for use in the prophylaxis/prevention or treatment of diabetes, and diabetes related diseases such as diabetic arteriopathy, diabetic retinopathy, or diabetic vasculopathy; as well as diabetic complications; for reducing the risk of developing a major cardiovascular event (such as HF, myocardial infarction, stroke, or death from cardiovascular causes) in patients who have diabetes, especially in patients who have diabetes that is accompanied by at least one other cardiovascular risk factor (such as especially hypertension); as well as for use in the prophylaxis/prevention or treatment of diabetic foot ulcers and/or for reducing the risk of lower extremety amputations in patients who have diabetes;
  for use in the prophylaxis/prevention or treatment of heart failure (HF) including especially chronic HF, including in particular systolic HF and diastolic HF; for reducing the risk of developing a major cardiovascular event (such as HF, myocardial infarction, stroke, or death from cardiovascular causes) in patients who are at cardiovascular risk (such as patients who have coronary artery disease and/or patients who have demonstrated clinical signs of congestive HF); as well as for use in the prophylaxis/prevention or treatment of ischemic heart diseases including angina pectoris, coronary diseases, and myocardial ischemia; cardiac insufficiency; or diastolic dysfunction;
  for use in the treatment of hypertension including especially difficult to treat/resistant hypertension;
  for use in the prophylaxis/prevention or treatment of atherosclerosis; as well as of peripheral arterial obliterant disease including chronic peripheral arteriopathy;
  for use in the prophylaxis/prevention or treatment of digital ulcers; or
  for use in the prophylaxis/prevention or treatment of connective tissue diseases;
wherein aprocitentan is (intended) to be administered in combination with an SGLT-2 inhibitor, or a pharmaceutically acceptable salt thereof.

30) A further embodiment relates to aprocitentan, or a pharmaceutically acceptable salt thereof, for use according to embodiment 29); wherein aprocitentan is
  for use in the prophylaxis/prevention or treatment of CKD [especially CKD of stages 1 to 4, notably CKD of stage 3], including CKD [especially CKD of stages 1 to 4, notably CKD of stage 3] caused by/associated with hypertension, and CKD [especially CKD of stages 1 to 4, notably CKD of stage 3] caused by/associated with diabetes (diabetic kidney disease, DKD);
  wherein such use is especially for the treatment of such DKD in a patient diagnosed with type 2 diabetes mellitus, wherein in particular aprocitentan reduces the rate of progression of DKD, wherein such reduced rate of progression may especially be expressed by a reduction in eGFR, a reduction of events of end-stage kidney disease (ESKD), or a reduction of events of renal death; wherein notably said patient presents in addition a history of hypertension;

for use prophylaxis/prevention or treatment of acute renal failure;
for use prophylaxis/prevention or treatment of chronic renal failure;
for use prophylaxis/prevention or treatment of diabetic nephropathy;
for use prophylaxis/prevention or treatment of glomerulonephritis;
for reducing the risk of developing a major cardiovascular event (such as HF, myocardial infarction, stroke, or death from cardiovascular causes) in patients who have diabetes, especially in patients who have diabetes that is accompanied by at least one other cardiovascular risk factor (such as especially hypertension);
for use in the prophylaxis/prevention or treatment of diabetic foot ulcers and/or for reducing the risk of lower extremety amputations in patients who have diabetes;
for use in the prophylaxis/prevention or treatment of heart failure (HF) including especially chronic HF; in particular systolic HF or diastolic HF;
for reducing the risk of developing a major cardiovascular event such as HF, myocardial infarction, stroke, or death from cardiovascular causes in patients who are at cardiovascular risk (such as patients who have coronary artery disease and/or patients who have demonstrated clinical signs of congestive HF);
for use in the prophylaxis/prevention or treatment of diastolic dysfunction;
for use in the treatment of hypertension including especially difficult to treat/resistant hypertension; or
for use in the prophylaxis/prevention or treatment of atherosclerosis; as well as of peripheral arterial obliterant disease including chronic peripheral arteriopathy;
wherein aprocitentan is (intended) to be administered in combination with an SGLT-2 inhibitor, or a pharmaceutically acceptable salt thereof.

31) A further embodiment relates to aprocitentan, or a pharmaceutically acceptable salt thereof, for use according to embodiment 29); wherein aprocitentan is
for use in the prophylaxis/prevention or treatment of CKD [especially CKD of stages 1 to 4, notably CKD of stage 3] caused by/associated with hypertension;
for use in the prophylaxis/prevention or treatment of CKD [especially CKD of stages 1 to 4, notably CKD of stage 3] caused by/associated with diabetes (DKD);
wherein such use is especially for the treatment of such DKD in a patient diagnosed with type 2 diabetes mellitus, wherein in particular aprocitentan reduces the rate of progression of DKD, wherein such reduced rate of progression may especially be expressed by a reduction in eGFR, a reduction of events of end-stage kidney disease (ESKD), or a reduction of events of renal death; wherein notably said patient presents in addition a history of hypertension;
for use prophylaxis/prevention or treatment of chronic renal failure caused by/associated with hypertension or caused by/associated with diabetes; diabetic nephropathy; or glomerulonephritis caused by/associated with hypertension;
for reducing the risk of developing a major cardiovascular event (such as HF, myocardial infarction, stroke, or death from cardiovascular causes) in patients who have diabetes, especially in patients who have diabetes that is accompanied by at least one other cardiovascular risk factor (such as especially hypertension);
for use in the prophylaxis/prevention or treatment of diabetic foot ulcers and/or for reducing the risk of lower extremety amputations in patients who have diabetes; or
for use in the prophylaxis/prevention or treatment of heart failure (HF) including especially chronic HF; in particular systolic HF or diastolic HF;
wherein aprocitentan is (intended) to be administered in combination with an SGLT-2 inhibitor, or a pharmaceutically acceptable salt thereof.

32) A further embodiment relates to aprocitentan, or a pharmaceutically acceptable salt thereof, for use according to embodiment 29); wherein aprocitentan is
for use in the prophylaxis/prevention or treatment of CKD [especially CKD of stages 1 to 4, notably CKD of stage 3] caused by/associated with hypertension; and/or
for use in the prophylaxis/prevention or treatment of CKD [especially CKD of stages 1 to 4, notably CKD of stage 3] caused by/associated with diabetes (DKD);
wherein such use is especially for the treatment of such DKD in a patient diagnosed with type 2 diabetes mellitus, wherein in particular aprocitentan reduces the rate of progression of DKD, wherein such reduced rate of progression may especially be expressed by a reduction in eGFR, a reduction of events of end-stage kidney disease (ESKD), or a reduction of events of renal death; wherein notably said patient presents in addition a history of hypertension; and/or
for reducing the risk of developing a major cardiovascular event (such as HF, myocardial infarction, stroke, or death from cardiovascular causes) in patients who have diabetes, especially in patients who have diabetes that is accompanied by at least one other cardiovascular risk factor (such as especially hypertension);
wherein aprocitentan is (intended) to be administered in combination with an SGLT-2 inhibitor, or a pharmaceutically acceptable salt thereof.

33) A further embodiment relates to aprocitentan, or a pharmaceutically acceptable salt thereof, for use according to embodiment 29); wherein aprocitentan is
for use in the prophylaxis/prevention or treatment of CKD [especially CKD of stages 1 to 4, notably CKD of stage 3] caused by/associated with hypertension; and/or
for use in the prophylaxis/prevention or treatment of CKD [especially CKD of stages 1 to 4, notably CKD of stage 3] caused by/associated with diabetes (DKD);
wherein such use is especially for the treatment of such DKD in a patient diagnosed with type 2 diabetes mellitus, wherein in particular aprocitentan reduces the rate of progression of DKD, wherein such reduced rate of progression may especially be expressed by a reduction in eGFR, a reduction of events of end-stage kidney disease (ESKD), or a reduction of events of renal death; wherein notably said patient presents in addition a history of hypertension;
wherein aprocitentan is (intended) to be administered in combination with an SGLT-2 inhibitor, or a pharmaceutically acceptable salt thereof.

34) A further embodiment relates to aprocitentan, or a pharmaceutically acceptable salt thereof, for use according to embodiment 29); wherein aprocitentan is
for use in the prophylaxis/prevention or treatment of CKD [especially CKD of stages 1 to 4, notably CKD of stage 3] caused by/associated with diabetes (DKD);
wherein, in a first sub-embodiment, such use is especially for the treatment of such DKD in a patient diagnosed with type 2 diabetes mellitus, wherein in particular aprocitentan reduces the rate of progression of DKD, wherein such reduced rate of progression may especially be expressed by a reduction in eGFR, a reduction of events of end-stage kidney disease (ESKD), or a reduction of events of renal death; wherein notably said patient presents in addition a history of hypertension;

wherein, in a second sub-embodiment, such use is especially for the treatment of such DKD, including treatment of diabetic nephropathy associated with an elevated serum creatinine and/or proteinuria [especially corresponding to CKD of stages 1 to 4 as defined by the Kidney Disease Improving Global Outcomes (KDIGO) Guidelines (and notably to such CKD of stage 3)], in patients with type 2 diabetes, especially in such patients presenting in addition a history of hypertension;

wherein aprocitentan is (intended) to be administered in combination with an SGLT-2 inhibitor, or a pharmaceutically acceptable salt thereof.

35) A further embodiment relates to aprocitentan, or a pharmaceutically acceptable salt thereof, for use according to embodiment 29); wherein aprocitentan is for reducing the risk of developing a major cardiovascular event (such as HF, myocardial infarction, stroke, or death from cardiovascular causes) in patients who have diabetes, especially in patients who have diabetes that is accompanied by at least one other cardiovascular risk factor (such as especially hypertension);

wherein aprocitentan is (intended) to be administered in combination with an SGLT-2 inhibitor, or a pharmaceutically acceptable salt thereof.

36) A further embodiment relates to aprocitentan, or a pharmaceutically acceptable salt thereof, for use according to any one of embodiments 29) to 35); wherein the SGLT-2 inhibitor, or a pharmaceutically acceptable salt thereof, is atigliflozin, bexagliflozin, canagliflozin, dapagliflozin, empagliflozin, ertugliflozin, henagliflozin, ipragliflozin, luseogliflozin, remogliflozin, sotagliflozin, or tofogliflozin, or a pharmaceutically acceptable salt thereof.

36(i) In a sub-embodiment, the SGLT-2 inhibitor is notably bexagliflozin, canagliflozin, dapagliflozin, empagliflozin, ertugliflozin, henagliflozin, ipragliflozin, luseogliflozin, sotagliflozin, or tofogliflozin (especially canagliflozin, dapagliflozin, or empagliflozin; in particular canagliflozin), or a pharmaceutically acceptable salt thereof.

37) A further embodiment relates to aprocitentan, or a pharmaceutically acceptable salt thereof, for use according to any one of embodiments 29) to 35); wherein the SGLT-2 inhibitor, or a pharmaceutically acceptable salt thereof, is canagliflozin, dapagliflozin, or empagliflozin (in particular canagliflozin), or a pharmaceutically acceptable salt thereof.

38) A further embodiment relates to aprocitentan, or a pharmaceutically acceptable salt thereof, for use according to any one of embodiments 29) to 35); wherein the SGLT-2 inhibitor, or a pharmaceutically acceptable salt thereof, is canagliflozin, or a pharmaceutically acceptable salt thereof.

39) A further embodiment relates to aprocitentan, or a pharmaceutically acceptable salt thereof, for use according to any one of embodiments 29) to 35); wherein the SGLT-2 inhibitor, or a pharmaceutically acceptable salt thereof, is dapagliflozin, or a pharmaceutically acceptable salt thereof.

40) A further embodiment relates to aprocitentan, or a pharmaceutically acceptable salt thereof, for use according to any one of embodiments 29) to 35); wherein the SGLT-2 inhibitor, or a pharmaceutically acceptable salt thereof, is empagliflozin, or a pharmaceutically acceptable salt thereof.

41) A further embodiment relates to aprocitentan, or a pharmaceutically acceptable salt thereof, for use according to any one of embodiments 29) to 40), wherein, mutatis mutandis, the pharmaceutically active ingredients are to be administered in a pharmaceutical unit dosage form as disclosed in any one of embodiments 5), 6), 7), or 8), or any one of their respective sub-embodiments 5(i), 5(ii), 5(iii), 6(i), 6(ii), 6(iii), 6(iv), 6(v), 6(vi), 6(vii), 8(i), 8(ii), 8(iii), 8(iv), 8(v), 8(vi), or 8(vii).

42) A further embodiment relates to aprocitentan, or a pharmaceutically acceptable salt thereof, for use in combination with an SGLT-2 inhibitor according to any one of embodiments 29) to 41), wherein aprocitentan is used in a crystalline form as defined in any one of embodiments 10) to 16), or 17) to 23) [especially as defined in embodiment 10), 11) or 12); or 17), 18), or 19), respectively].

43) A further embodiment relates to aprocitentan, or a pharmaceutically acceptable salt thereof, for use in combination with an SGLT-2 inhibitor according to any one of embodiments 29) to 41), wherein aprocitentan is used in a crystalline form as defined in any one of embodiments 10) to 16) [especially as defined in embodiment 10), 11) or 12)].

44) A further embodiment relates to aprocitentan, or a pharmaceutically acceptable salt thereof, for use in combination with an SGLT-2 inhibitor according to any one of embodiments 29) to 41), wherein, mutatis mutandis, aprocitentan is to be administered in combination to a suitable conventional background therapy, wherein said background therapy is especially as defined in embodiment 9) or its sub-embodiments 9(i), 9(ii) or 9(iii).

45) One important aspect of the invention, thus, relates to aprocitentan, or a pharmaceutically acceptable salt thereof, for use in combination/co-therapy with an SGLT-2 inhibitor according to any one of embodiments 29) to 44). In particular, based on the dependencies of the different embodiments (or their respective sub-embodiments) as disclosed hereinabove, the following embodiments are, mutatis mutandis, possible and intended and herewith specifically disclosed in individualized form:

29+5, 29+6, 29+7, 29+8, 29+9+5, 29+9+6, 29+9+7, 29+9+8, 29+12+5, 29+12+6, 29+12+7, 29+12+8, 29+12+9+5, 29+12+9+6, 29+12+9+7, 29+12+9+8, 31+5, 31+6, 31+7, 31+8, 31+9+5, 31+9+6, 31+9+7, 31+9+8, 31+12+5, 31+12+6, 31+12+7, 31+12+8, 31+12+9+5, 31+12+9+6, 31+12+9+7, 31+12+9+8, 32+5, 32+6, 32+7, 32+8, 32+9+5, 32+9+6, 32+9+7, 32+9+8, 32+12+5, 32+12+6, 32+12+7, 32+12+8, 32+12+9+5, 32+12+9+6, 32+12+9+7, 32+12+9+8, 33+5, 33+6, 33+7, 33+8, 33+9+5, 33+9+6, 33+9+7, 33+9+8, 33+12+5, 33+12+6, 33+12+7, 33+12+8, 33+12+9+5, 33+12+9+6, 33+12+9+7, 33+12+9+8, 34+5, 34+6, 34+7, 34+8, 34+9+5, 34+9+6, 34+9+7, 34+9+8, 34+12+5, 34+12+6, 34+12+7, 34+12+8, 34+12+9+5, 34+12+9+6, 34+12+9+7, 34+12+9+8, 36+5, 36+6, 36+7, 36+9+5, 36+9+6, 36+9+7, 36+9+8, 36+12+5, 36+12+6, 36+12+7, 36+12+8, 36+12+9+5, 36+12+9+6, 36+12+9+7, 36+12+9+8, 36+29+5, 36+29+6, 36+29+7, 36+29+8, 36+29+9+5, 36+29+9+6, 36+29+9+7, 36+29+9+8, 36+29+12+5, 36+29+12+6, 36+29+12+7, 36+29+12+8, 36+29+12+9+5, 36+29+12+9+6, 36+29+12+9+7, 36+29+12+9+8, 36+31+5, 36+31+6, 36+31+7, 36+31+8, 36+31+9+5, 36+31+9+6, 36+31+9+7, 36+31+9+8, 36+31+12+5, 36+31+12+6, 36+31+12+7, 36+31+12+8, 36+31+12+9+5, 36+31+12+9+6, 36+31+12+9+7, 36+31+12+9+8, 36+32+5, 36+32+6, 36+32+7, 36+32+8, 36+32+9+5, 36+32+9+6, 36+32+9+7, 36+32+9+8, 36+32+12+5, 36+32+12+6, 36+32+12+7, 36+32+12+8, 36+32+12+9+5, 36+32+12+9+6, 36+32+12+9+7, 36+32+12+9+8, 36+33+5, 36+33+6, 36+33+7, 36+33+8, 36+33+9+5, 36+33+9+6, 36+33+9+7, 36+33+9+8, 36+33+12+5, 36+33+12+6, 36+33+12+7, 36+33+12+8, 36+33+12+9+5,

36+33+12+9+6, 36+33+12+9+7, 36+33+12+9+8, 36+34+5, 36+34+6, 36+34+7, 36+34+8, 36+34+9+5, 36+34+9+6, 36+34+9+7, 36+34+9+8, 36+34+12+5, 36+34+12+6, 36+34+12+7, 36+34+12+8, 36+34+12+9+5, 36+34+12+9+6, 36+34+12+9+7, 36+34+12+9+8, 37+5, 37+6, 37+7, 37+9+5, 37+9+6, 37+9+7, 37+9+8, 37+12+5, 37+12+6, 37+12+7, 37+12+8, 37+12+9+5, 37+12+9+6, 37+12+9+7, 37+12+9+8, 37+29+5, 37+29+6, 37+29+7, 37+29+8, 37+29+9+5, 37+29+9+6, 37+29+9+7, 37+29+9+8, 37+29+12+5, 37+29+12+6, 37+29+12+7, 37+29+12+8, 37+29+12+9+5, 37+29+12+9+6, 37+29+12+9+7, 37+29+12+9+8, 37+31+5, 37+31+6, 37+31+7, 37+31+8, 37+31+9+5, 37+31+9+6, 37+31+9+7, 37+31+9+8, 37+31+12+5, 37+31+12+6, 37+31+12+7, 37+31+12+8, 37+31+12+9+5, 37+31+12+9+6, 37+31+12+9+7, 37+31+12+9+8, 37+32+5, 37+32+6, 37+32+7, 37+32+8, 37+32+9+5, 37+32+9+6, 37+32+9+7, 37+32+9+8, 37+32+12+5, 37+32+12+6, 37+32+12+7, 37+32+12+8, 37+32+12+9+5, 37+32+12+9+6, 37+32+12+9+7, 37+32+12+9+8, 37+33+5, 37+33+6, 37+33+7, 37+33+8, 37+33+9+5, 37+33+9+6, 37+33+9+7, 37+33+9+8, 37+33+12+5, 37+33+12+6, 37+33+12+7, 37+33+12+8, 37+33+12+9+5, 37+33+12+9+6, 37+33+12+9+7, 37+33+12+9+8, 37+34+5, 37+34+6, 37+34+7, 37+34+8, 37+34+9+5, 37+34+9+6, 37+34+9+7, 37+34+9+8, 37+34+12+5, 37+34+12+6, 37+34+12+7, 37+34+12+8, 37+34+12+9+5, 37+34+12+9+6, 37+34+12+9+7, 37+34+12+9+8, 38+5, 38+6, 38+8, 38+9+5, 38+9+6, 38+9+7, 38+9+8, 38+12+5, 38+12+6, 38+12+7, 38+12+8, 38+12+9+5, 38+12+9+6, 38+12+9+7, 38+12+9+8, 38+29+5, 38+29+6, 38+29+7, 38+29+8, 38+29+9+5, 38+29+9+6, 38+29+9+7, 38+29+9+8, 38+29+12+5, 38+29+12+6, 38+29+12+7, 38+29+12+8, 38+29+12+9+5, 38+29+12+9+6, 38+29+12+9+7, 38+29+12+9+8, 38+31+5, 38+31+6, 38+31+7, 38+31+8, 38+31+9+5, 38+31+9+6, 38+31+9+7, 38+31+9+8, 38+31+12+5, 38+31+12+6, 38+31+12+7, 38+31+12+8, 38+31+12+9+5, 38+31+12+9+6, 38+31+12+9+7, 38+31+12+9+8, 38+32+5, 38+32+6, 38+32+7, 38+32+8, 38+32+9+5, 38+32+9+6, 38+32+9+7, 38+32+9+8, 38+32+12+5, 38+32+12+6, 38+32+12+7, 38+32+12+8, 38+32+12+9+5, 38+32+12+9+6, 38+32+12+9+7, 38+32+12+9+8, 38+33+5, 38+33+6, 38+33+7, 38+33+8, 38+33+9+5, 38+33+9+6, 38+33+9+7, 38+33+9+8, 38+33+12+5, 38+33+12+6, 38+33+12+7, 38+33+12+8, 38+33+12+9+5, 38+33+12+9+6, 38+33+12+9+7, 38+33+12+9+8, 38+34+5, 38+34+6, 38+34+7, 38+34+8, 38+34+9+5, 38+34+9+6, 38+34+9+7, 38+34+9+8, 38+34+12+5, 38+34+12+6, 38+34+12+7, 38+34+12+8, 38+34+12+9+5, 38+34+12+9+6, 38+34+12+9+7, 38+34+12+9+8.

In the list above, the numbers refer to the embodiments according to their numbering provided hereinabove whereas "+" indicates the dependency from another embodiment. The different individualised embodiments are separated by commas. In other words, "34+9+8" for example refers to embodiment 34) depending, mutatis mutandis, on embodiment 9), depending on embodiment 8), i.e. embodiment "34+9+8" corresponds to embodiment 34) further limited by the features as defined in embodiments 9) and 8) (or their respective sub-embodiments).

Accordingly, aprocitentan or a pharmaceutically acceptable salt thereof according to this invention is for use in combination (or co-therapy) with said further pharmaceutically active ingredients.

A combined treatment (or co-therapy) may be effected simultaneously, separately, or over a period of time (especially simultaneously).

"Simultaneously", when referring to an administration type, means in the present application that the administration type concerned consists in the administration of two or more active ingredients and/or treatments at approximately the same time; wherein it is understood that a simultaneous administration will lead to exposure of the subject to the two or more active ingredients and/or treatments at the same time. When administered simultaneously, said two or more active ingredients may be administered in a fixed dose combination, or in an equivalent non-fixed dose combination (e.g. by using two or more different pharmaceutical compositions to be administered by the same route of administration at approximately the same time), or by a non-fixed dose combination using two or more different routes of administration; wherein said administration leads to essentially simultaneous exposure of the subject to the two or more active ingredients and/or treatments. When used in combination with an SGLT-2 inhibitor the aprocitentan would possibly be used "simultaneously".

"Fixed dose combination", when referring to an administration type, means in the present application that the administration type concerned consists in the administration of one single pharmaceutical composition comprising the two or more active ingredients, such as especially the pharmaceutical compositions of any one of embodiments 1) to 28).

"Separately", when referring to an administration type, means in the present application that the administration type concerned consists in the administration of two or more active ingredients and/or treatments at different points in time; wherein it is understood that a separate administration will lead to a treatment phase (e.g. at least 1 hour, notably at least 6 hours, especially at least 12 hours) where the subject is exposed to the two or more active ingredients and/or treatments at the same time; but a separate administration may also lead to a treatment phase where for a certain period of time (e.g. at least 12 hours, especially at least one day) the subject is exposed to only one of the two or more active ingredients and/or treatments. Separate administration especially refers to situations wherein at least one of the active ingredients and/or treatments is given with a periodicity substantially different from daily (such as once or twice daily) administration (e.g. wherein one active ingredient and/or treatment is given e.g. once or twice a day, and another is given e.g. every other day, or once a week or at even longer distances).

By administration "over a period of time" is meant in the present application the subsequent administration of two or more active ingredients and/or treatments at different times. The term in particular refers to an administration method according to which the entire administration of one of the active ingredients and/or treatments is completed before the administration of the other/the others begins. In this way it is possible to administer one of the active ingredients and/or treatments for several months before administering the other active ingredient(s) and/or treatment(s).

It is understood that any embodiment relating to aprocitentan, or a pharmaceutically acceptable salt thereof, for use in the treatment of certain endothelin related diseases as specifically defined herein, wherein aprocitentan is (intended) to be administered in combination with an SGLT-2 inhibitor (especially an SGLT-2 inhibitor as specifically defined in such embodiment) also relates to such SGLT-2 inhibitor as disclosed herein (intended) to be administered in combination with aprocitentan, or a pharmaceutically acceptable salt thereof, for use in the treatment of said endothelin related diseases;
  to the use of aprocitentan for the manufacture of a medicament/a pharmaceutical composition comprising aprocitentan, or a pharmaceutically acceptable salt thereof, and said SGLT-2 inhibitor as disclosed herein, for use in the treatment of said endothelin related diseases;

to the use of aprocitentan for the manufacture of a medicament/pharmaceutical composition comprising, as active ingredient, aprocitentan, or a pharmaceutically acceptable salt thereof, for use in the treatment of said endothelin related diseases; wherein said medicament/pharmaceutical composition is (intended) to be used in combination with an SGLT-2 inhibitor as disclosed herein;

to the use of an SGLT-2 inhibitor as disclosed herein for the manufacture of a medicament/pharmaceutical composition comprising, as active ingredient, such SGLT-2 inhibitor as disclosed herein, for use in the treatment of said endothelin related diseases; wherein said medicament/pharmaceutical composition is (intended) to be used in combination with aprocitentan;

to the use of a pharmaceutical composition comprising aprocitentan, or a pharmaceutically acceptable salt thereof, and such SGLT-2 inhibitor as disclosed herein for the treatment of said endothelin related diseases;

to a medicament for the prevention or treatment said endothelin related diseases, said medicament comprising aprocitentan, or a pharmaceutically acceptable salt thereof; wherein said medicament is (intended) to be administered in combination with said SGLT-2 inhibitor;

to a method of treating said endothelin related diseases comprising administering to a subject (preferably a human) in need thereof an effective amount of aprocitentan, or a pharmaceutically acceptable salt thereof, to be administered in combination with an effective amount of said SGLT-2 inhibitor;

to a method of treating said endothelin related diseases comprising administering to a subject in need thereof an effective amount of a pharmaceutical composition comprising aprocitentan, or a pharmaceutically acceptable salt thereof, and said SGLT-2 inhibitor as disclosed herein; and to a method of treating said endothelin related diseases comprising administering to a subject (preferably a human) in need thereof an effective amount of said SGLT-2 inhibitor as disclosed herein to be administered in combination with an effective amount of aprocitentan, or a pharmaceutically acceptable salt thereof.

46) A further embodiment relates to aprocitentan, or a pharmaceutically acceptable salt thereof, for use in a method for reducing fluid retention and/or reducing the risk of congestive heart failure in a subject (preferably a human) in need of an ERA, comprising administering to said subject an effective amount of aprocitentan, wherein aprocitentan is to be administered in combination with an SGLT-2 inhibitor as disclosed herein, wherein the characteristics of any one of embodiments 1) to 45) apply mutatis mutandis;

for reducing volume depletion, and/or normalizing blood viscosity, and/or reducing the risk of lower extremity amputations in a subject (preferably a human) in need of an SGLT-2 inhibitor (such as especially a subject diagnosed with type 2 diabetes and/or DKD), comprising administering to said subject an effective amount of said SGLT-2 inhibitor as disclosed herein, wherein said SGLT-2 inhibitor is to be administered in combination with an effective amount of aprocitentan wherein the characteristics of any one of embodiments 1) to 45) apply mutatis mutandis;

for protecting the kidney and/or to improve renal hemodynamics, and/or reducing the risk of acute renal failure in a subject (preferably a human) in need of an SGLT-2 inhibitor (such as especially a subject diagnosed with type 2 diabetes and/or DKD), comprising administering to said subject an effective amount of said SGLT-2 inhibitor as disclosed herein, wherein said SGLT-2 inhibitor is to be administered in combination with an effective amount of aprocitentan wherein the characteristics of any one of embodiments 1) to 45) apply mutatis mutandis;

for reducing blood pressure in a subject (preferably a human), comprising administering to said subject an effective amount of aprocitentan, wherein aprocitentan is to be administered in combination with an SGLT-2 inhibitor as disclosed herein, wherein the characteristics of any one of embodiments 1) to 45) apply mutatis mutandis;

for reducing blood sugar levels in a subject (preferably a human), comprising administering to said subject an effective amount of aprocitentan, wherein aprocitentan is to be administered in combination with an SGLT-2 inhibitor as disclosed herein, wherein the characteristics of any one of embodiments 1) to 45) apply mutatis mutandis; and/or for the prevention or treatment of an endothelin related disease as defined herein, comprising administering to said subject an effective amount of said SGLT-2 inhibitor as disclosed herein, wherein said SGLT-2 inhibitor is to be administered in combination with an effective amount of aprocitentan wherein the characteristics of any one of embodiments 1) to 45) apply mutatis mutandis; wherein the beneficial effect said SGLT-2 inhibitor on sodium re-uptake remains unaffected by aprocitentan.

47) A further aspect of the invention relates to aprocitentan, or a pharmaceutically acceptable salt thereof, for use in the treatment of CKD [especially CKD of stages 1 to 4, notably CKD of stage 3] caused by/associated with diabetes (DKD) [including diabetic nephropathy associated with an elevated serum creatinine and/or proteinuria [especially corresponding to CKD of such stages]; wherein, in a sub-embodiment, such use is especially for the treatment of such DKD in a patient diagnosed with type 2 diabetes mellitus [notably in such patients presenting in addition a history of hypertension], wherein in particular aprocitentan reduces the rate of progression of DKD, wherein such reduced rate of progression may especially be expressed by a reduction in eGFR, a reduction of events of end-stage kidney disease (ESKD), or a reduction of events of renal death;

wherein aprocitentan is used as single therapy; or (preferably) in combination/co-therapy [effected simultaneously, separately, or over a period of time (especially simultaneously)] with an SGLT-2 inhibitor, and/or conventional background therapy (or first line therapy) as defined before;

wherein said aprocitentan is to be administered in a suitable pharmaceutically efficacious unit dosage form as defined in embodiments 5) or 6) and their respective sub-embodiments 5(i), 5(ii), 5(iii), 6(i), 6(ii), 6(iii), 6(iv), 6(v), 6(vi), or 6(vii); [in particular in a unit dosage form suitable for the oral administration of 1 mg, 2.5 mg, 5 mg, 10 mg, 12.5 mg, 20 mg, 25 mg, 30 mg, 40 mg, or 50 mg; (especially 10 mg, 12.5 mg, 20 mg, 25 mg, 30 mg, 40 mg, or 50 mg; notably 12.5 mg, 25 mg or 50 mg) per day of aprocitentan];
wherein said SGLT-2 inhibitor, if present, is especially as defined in embodiments 7) or 8); wherein said SGLT-2 inhibitor is especially to be administered in a suitable pharmaceutically efficacious unit dosage form as defined in embodiments 7) or 8) and its sub-embodiments 8(i), 8(ii), 8(iii), 8(iv), 8(v), 8(vi), or 8(vii);
wherein said conventional background therapy, if present, is especially as defined in embodiment 9) and its sub-embodiments; wherein said conventional background therapy is especially to be administered in a suitable pharmaceutically efficacious unit dosage form as defined in embodiment 9) and its sub-embodiments 9(i), 9(ii) or 9(iii);
and wherein said conventional background therapy is suitable, preferably said conventional background therapy is indicated (i.e. approved by a national health authority such as the FDA or the EMA) for the treatment of such DKD according to this embodiment.

Particular embodiments of the invention are described in the following Examples, which serve to illustrate the invention in more detail without limiting its scope in any way.

EXPERIMENTAL PROCEDURES

Abbreviations

The following abbreviations are used throughout the specification and the examples:
Ac acetyl
AcOH acetic acid
aq. aqueous
DCM dichloromethane
DMSO dimethylsulfoxide
EtOAc ethyl acetate
eq. equivalent(s)
FTIR Fourier Transform Infrared Spectroscopy or Spectrum
HPLC High Performance Liquid Chromatography
iPrOAc isopropyl acetate
MeOH methanol
MIBK methyl iso-butyl ketone
org. organic
rt room temperature
THF tetrahydrofuran
vol. volume(s)
w/w weight-per-weight ratio
wt. weight unit
XRPD X-ray powder diffraction

EXAMPLES

Method for Obtaining XRPD Patterns

All XRPD patterns for the solid forms described herein have been obtained as described hereafter. X-ray powder diffraction patterns were collected on a Bruker D8 Advance X-ray diffractometer equipped with a Lynxeye detector operated with CuKα-radiation in reflection mode (coupled two Theta/Theta). Typically, the X-ray tube was run at of 40 kV/40 mA. A step size of 0.02° (2θ) and a step time of 76.8 sec over a scanning range of 3-50° in 2θ were applied. The divergence slit was set to fixed 0.3. Powders were slightly pressed into a silicon single crystal sample holder with depth of 0.5 mm and samples were rotated in their own plane during the measurement. Diffraction data are reported using combined Cu Kα1 and Kα2 radiation, without Kα2 stripping. The accuracy of the 2θ values as provided herein is in the range of +/−0.1-0.2° as it is generally the case for conventionally recorded X-ray powder diffraction patterns.

Example 1: Form A 1.1. A 3 L double jacketed reactor was charged with 5-(4-bromophenyl)-4-(2-((5-bromopyrimidin-2-yl)oxy) ethoxy)-6 fluoropyrimidine (100 g, 0.213 mol, 1 eq.), sulfamide (40.9 g, 0.425 mol, 2.0 eq.), $K_2CO_3$ (147 g, 1.06 mol, 5 eq.) and DMSO (500 mL, 5 vol.) doped with water (2 mL, 0.111 mol, 0.5 eq.). The heterogeneous mixture was heated to 70° C. during ca. 3 h, after which time complete conversion was observed. After cooling to 20° C., most of the inorganic salt freight was removed by filtration. The filter cake was washed with EtOAc/iPrOAc 1:1 (300 mL, 3 vol.). Celite (100 g, 1 wt.) topped with a layer of charcoal (20 g, 0.2 wt.) was preconditioned with EtOAc/iPrOAc 1:1 (500 mL, 5 vol.) (filtrate discarded). The reaction mixture was filtered over this cake and rinsed with EtOAc/iPrOAc 1:1 (300 mL, 3 vol.). Then 1M aq. NaOAc solution (500 mL, 0.5 mol, 2.3 eq, 5 vol.) was added while keeping the temperature at 25-35° C. The aq. phase was washed a second time with EtOAc/iPrOAc 1:1 (500 mL, 5 vol.). To the aq. phase, 1M $H_2SO_4$ (200 mL, 0.2 mol, 1 eq., 2 vol.) was added during 1 h at 25-30° C. Crystallization started at pH 8.5-8.0. The crude product was filtered off as XRPD pattern form K (DMSO solvate) or a mixture of form A and form K. It was washed twice with water (2×1000 mL, 2×10 vol.). The solid was slurried in water (1000 mL, 10 vol.) at rt for 3 h. The solid was filtered off and slurried a second time in water (1000 mL, 10 vol.) at rt for 3 h. After washing with water (1000 mL, 10 vol.), the pure product was dried in vacuum at 40° C. to afford {5-(4-bromo-phenyl)-6-[2-(5-bromo-pyrimidin-2-yloxy)-ethoxy]-pyrimidin-4-yl}-sulfamide as a white to off-white solid (75 g, 65% yield, XRPD pattern form A).

1.2. A reactor (200 L Hastelloy) was charged with 5-(4-bromophenyl)-4-(2-((5-bromopyrimidin-2-yl)oxy) ethoxy)-6 fluoropyrimidine (24.2 kg, 51.5 mol), sulfamide (9.7 kg, 100.9 mol, 1.96 eq.), potassium carbonate (35.5 kg, 256.9 mol, 5.0 eq.), DMSO (133 kg, 5 vol.) and water (490 g, 27.2 mol, 0.53 eq.). The contents of the reactor were heated to 70-75° C. Monitoring by HPLC showed complete conversion in 4 hours. The contents were cooled to 20-25° C. and the solids were centrifuged off. Each load was washed with EtOAc/iPrOAc 1:1 (65 kg, 3 vol.). The filtrate was re-charged in the reactor and charcoal (2.4 kg, 10% w/w) and Celite® (4.8 kg, 20% w/w) were added. The contents were agitated for 1 h at 15-20° C. and filtered through a cartridge filter back into the reactor. The filters were rinsed with EtOAc/iPrOAc 1:1 (43 kg, 2 vol.). NaOAc (8% in water) (124 kg, 5 vol.) was added over 2 h, keeping the temperature below 25° C. After phase separation, the aq. layer was washed with EtOAc/iPrOAc 1:1 (109 kg, 5 vol.) at 20-25° C. Sulfuric acid (5% in water; 64 L, 32.6 mol, 0.63 eq.) was added to the aq. layer at 25-30° C. over 2 hours to reach pH 6.4. The contents were then cooled to 15-20° C. for 1 h. The solids were filtered off and washed twice with water (2×24 L, 2×1 vol.). The solid was slurried twice in water (2×242 kg, 2×10 vol.) at 15-20° C. for 3 hours each, filtered and dried, to yield 5-(4-bromo-phenyl)-6-[2-(5-bromo-pyrimidin-2-yloxy)-ethoxy]-pyrimidin-4-yl}-sulfamide as a white solid (21.6 g, 77% yield, XRPD pattern Form A).

Example 2: Form C 0.2 mL of a stock solution of {5-(4-bromo-phenyl)-6-[2-(5-bromo-pyrimidin-2-yloxy)-ethoxy]-pyrimidin-4-yl}-sulfamide dissolved in THF at 50 mg/mL was dispensed to 3 vials. The solvent was evaporated for 90 min in a Combidancer device from Hettich AG (Bäch, Switzerland) operated at 35° C. and 200 mbar. Immediately thereafter 0.015 mL of MeOH for the first vial, EtOH for the second vial and iPrOH for the third vial was added and the vials were allowed to stand closed for 3 days. Solid residue of {5-(4-bromo-phenyl)-6-[2-(5-bromo-pyrimidin-2-yloxy)-ethoxy]-pyrimidin-4-yl}-sulfamide in Form C was obtained for each of these solvents.

Example 3: ACT-132577 Tablets

Tablets containing each 50 mg of ACT-132577 can be prepared using a wet granulation process. The tablet composition is the following:

| ACT-132577 tablets (250 mg) | | | |
|---|---|---|---|
| | MATERIAL (CHEMICAL NAME) | mg/tablet | Weight %/tablet |
| Intra-ingranular | ACT-132577 (amorphous, solid form A or solid form C, as described herein) | 50.00 | 20.00 |
| | Microcrystalline cellulose | 61.50 | 24.60 |
| | Lactose (200M) | 122.25 | 48.90 |
| | Hydroxypropylcellulose | 5.50 | 2.20 |
| | Croscarmellose sodium | 4.50 | 1.80 |
| | Water | qs | qs |
| Extra-granular | Croscarmellose sodium | 5.00 | 2.00 |
| | Magnesium stearate | 1.25 | 0.50 |
| | Total | 250.00 | 100.00 | qs = quantity sufficient
Perferably, ACT-132577 Form A (as described herein) will be used for making the tablets.

Example 4: ACT-132577 Tablets

The tablets of Example 3 can be coated with a layer of Aquapolish® white MS or Aquapolish® white PVA (coating manufacturer: Biogrund).

Example 5: ACT-132577 Tablets

Tablets containing each 50 mg of ACT-132577 can be prepared using a wet granulation process. The tablet composition is the following:

| ACT-132577 tablets (250 mg) | | | |
|---|---|---|---|
| | MATERIAL (CHEMICAL NAME) | mg/tablet | Weight %/tablet |
| Intra-ingranular | ACT-132577 (amorphous, solid form A or solid form C, as described herein) | 50.00 | 20.00 |
| | Microcrystalline cellulose | 61.25 | 24.50 |
| | Lactose (200M) | 122.50 | 49.00 |
| | Hydroxypropylcellulose | 5.00 | 2.00 |
| | Croscarmellose sodium | 5.00 | 2.00 |
| | Water | qs | qs |
| Extra-granular | Croscarmellose sodium | 5.00 | 2.00 |
| | Magnesium stearate | 1.25 | 0.50 |
| | Total | 250.00 | 100.00 | qs = quantity sufficient
Perferably, ACT-132577 Form A (as described herein) will be used for making the tablets.

Example 6

The tablets of Example 5 can be coated with a layer of Aquapolish® white MS or Aquapolish® white PVA (coating manufacturer: Biogrund).

Example 7: ACT-132577 Tablets

Tablets containing each 12.5 mg of ACT-132577 can be prepared using a wet granulation process. The tablet composition is the following:

| ACT-132577 tablets (100 mg) | | | |
|---|---|---|---|
| | Material (Chemical name) | mg/tablet | Weight %/tablet |
| Intra-ingranular | ACT-132577 (amorphous, solid form A or solid form C, as described herein) | 12.50 | 12.50 |
| | Microcrystalline cellulose | 27.00 | 27.00 |
| | Lactose (200M) | 54.00 | 54.00 |
| | Hydroxypropylcellulose | 2.00 | 2.00 |
| | Croscarmellose sodium | 2.00 | 2.00 |
| | Water | qs | qs |
| Extra-granular | Croscarmellose sodium | 2.00 | 2.00 |
| | Magnesium stearate | 0.50 | 0.50 |
| | Total | 100.00 | 100.00 | qs = quantity sufficient
Perferably, ACT-132577 Form A (as described herein) will be used for making the tablets.

Example 8: ACT-132577 Tablets

The tablets of Example 7 can be coated with a layer of Aquapolish® white MS or Aquapolish® white PVA (coating manufacturer: Biogrund).

Example 9: ACT-132577 Tablets

Tablets containing each 12.5 mg of ACT-132577 can be prepared using a wet granulation process. The tablet composition is the following:

| ACT-132577 tablets (100 mg) | | | |
|---|---|---|---|
| | Material (Chemical name) | mg/tablet | Weight %/tablet |
| Intra-ingranular | ACT-132577 (amorphous, solid form A or solid form C, as described herein) | 12.50 | 12.50 |
| | Microcrystalline cellulose | 27.50 | 27.50 |
| | Lactose (200M) | 53.50 | 53.50 |
| | Hydroxypropylcellulose | 2.20 | 2.20 |
| | Croscarmellose sodium | 1.80 | 1.80 |
| | Water | qs | qs |

-continued

ACT-132577 tablets (100 mg)

| | Material (Chemical name) | mg/tablet | Weight %/tablet |
|---|---|---|---|
| Extra-granular | Croscarmellose sodium | 2.00 | 2.00 |
| | Magnesium stearate | 0.50 | 0.50 |
| | Total | 100.00 | 100.00 | qs = quantity sufficient
Perferably, ACT-132577 Form A (as described herein) will be used for making the tablets.

Example 10: ACT-132577 Tablets

The tablets of Example 9 can be coated with a layer of Aquapolish® white MS or Aquapolish® white PVA (coating manufacturer: Biogrund).
Properties of the Crystal Forms Example 11: Storage at Room Temperature A sample of Form A crystals of the COMPOUND (as obtained according to Example 1 above) has been stored at a temperature of 20-25° C. at 92% relative humidity for 2 months. X-ray powder diffraction performed on that sample at the end of the 2 months showed that the sample was still consisting only in Form A crystals of the COMPOUND. The same result was obtained after storage for 8 weeks under the above conditions. HPLC control of the sample after 8 weeks storage revealed no significant change in peak area %, i.e. no significant degradation was observed under such conditions.

Example 12: Hygroscopicity

Form A is considered to be slightly hygroscopic as determined by gravimetric vapor sorption (GVS). Mass increase of a sample as obtained according to Example 1 in the first cycle from 40% r.h. to 80% r.h. corresponds to 0.4%. At 95% r.h. 2.2% moisture were taken up in a reversible way without hysteresis upon drying.
Examples of Therapeutic Uses of ACT-132577

Therapeutic effects can be modeled in multiple animal models. For example, the spontaneously hypertensive rat (SHR) is the most extensively used animal model for genetic hypertension. It is characterized by increased stroke damage, insulin resistance syndrome and renal impairment. Renal impairment comprises arteriolar damage, glomerular injury and proteinuria. Therefore, the SHR model can be used to mimic a cardiovascular condition associated with several risk factors, namely hypertension, insulin resistance and renal failure (M. A. Poteza et al. Am J Physiol Heart Circ Physiol (2005) 289: H813-H822; L. G. Feld et al. Kidney International (1981), 20, 606-614). The Dahl salt-sensitive rat and DOCA-salt rat are models of salt-sensitive hypertension associated with either strong mineralocorticoid receptors stimulation (DOCA-salt model) or low/moderate mineralocorticoid receptors stimulation (Dahl-salt model). Both models are characterized by high blood pressure, endothelial dysfunction, end organ damage involving the heart, the brain and the kidney (Y. M. Pinto et al. Cardiovascular Research 1998, 39, 77-88).

Example A: Acute Effects of ACT-132577 in Dahl Salt-Sensitive Rats

The acute effects of ACT-132577 on blood pressure, in particular on mean arterial blood pressure (hereafter "MAP"), and heart rate (hereafter "HR") can be evaluated by means of telemetry in conscious, male hypertensive Dahl salt-sensitive rats (hereafter "Dahl-S rats"—see details about this model in Rapp, *Hypertension* (1982), 4, 753-763).

Elevated blood pressure is induced in Dahl-S rats by providing 1% sodium chloride in drinking water. Groups of 6-7 Dahl-S rats are used for the vehicle (7.5% gelatin aqeuous solution) and each dose of ACT-132577 tested (0.3, 1, 3, 10, 30, 100, and 300 mg/kg). Effects of ACT-132577 on HR and MAP are calculated for individual animals relative to the 24 h period before administering. The results obtained regarding MAP (maximal MAP decrease observed over 6 consecutive hours) are summarised in FIG. 3 (data are presented as mean±standard error of the mean). In summary, a dose of 10 mg/kg ACT-132577 decreased MAP by 19±4 mm Hg in Dahl-S rats. In contrast to MAP, HR was not affected.

Example B: Acute Effects of ACT-132577 in Deoxycorticosterone Acetate Salt Rats

The acute effects of ACT-132577 on blood pressure, in particular on mean arterial blood pressure (hereafter "MAP"), and heart rate (hereafter "HR") can be evaluated by means of telemetry in conscious, male hypertensive deoxycorticosterone acetate salt rats (hereafter "DOCA-salt rats"—see details about this model in Gavras et al., *Circ. Res.* (1975), 36, 300-309).

In the DOCA-salt rats, hypertension is induced by the combination of unilateral nephrectomy, implantation of pellets of the mineralocorticoid analog DOCA, and provision of 1% sodium chloride in drinking water. Groups of 6-11 DOCA-salt rats are used for the vehicle (7.5% gelatin aqeuous solution) and each dose of ACT-132577 tested (0.3, 1, 3, 10, 30, 100, and 300 mg/kg). Effects of ACT-132577 on HR and MAP are calculated for individual animals relative to the 24 h period before administering. The results obtained regarding MAP (maximal MAP decrease observed over 6 consecutive hours) are summarised in FIG. 4 (data are presented as mean±standard error of the mean). In summary, a dose of 10 mg/kg ACT-132577 decreased MAP by 29±6 mm Hg in DOCA-salt rats. In contrast to MAP, HR was not affected.

Example C: Acute Effects of ACT-132577 in Spontaneaously Hypertensive Rats

The acute effects of ACT-132577 on blood pressure, in particular on mean arterial blood pressure (hereafter "MAP"), and heart rate (hereafter "HR") can be evaluated by means of telemetry in conscious, male spontaneaously hypertensive rats (hereafter "SHRs"—see details about this model in Atanur et al., *Genome Res*. (2010), 20, 791-803).

Groups of 4-6 SHRs are used for the vehicle (7.5% gelatin aqeuous solution) and each dose of ACT-132577 tested (1, 3, 10, 30, 100, and 300 mg/kg). Effects of ACT-132577 on HR and MAP are calculated for individual animals relative to the 24 h period before administering. The results obtained regarding MAP (maximal MAP decrease observed over 6 consecutive hours) are summarised in FIG. 5 (data are presented as mean±standard error of the mean). In summary, a dose of 100 mg/kg ACT-132577 decreased MAP by 18±4 mm Hg in SHRs. In contrast to MAP, HR was not affected.

Example D: Acute Effects of ACT-132577, Alone or in Combination with Valsartan, in Spontaneaously Hypertensive Rats The acute effects of ACT-132577 administered orally at a single dose of 100 mg/kg on blood pressure, in particular on mean arterial blood pressure (hereafter "MAP"), and heart rate (hereafter "HR"), with ACT-132577 being used either alone or in combination with valsartan administered orally at a single dose of 10 mg/kg, can be evaluated by means of telemetry in conscious, male spontaneaously hypertensive rats (hereafter "SHRs"—see details about this model in Atanur et al., Genome Res. (2010), 20, 791-803).

6 SHRs per treatment group are used for this test. The results obtained regarding MAP are summarised in FIG. 6 wherein each data point is presented as a 6-hour mean (NB: the expected additive effect of the combination of the two drugs, referred to as "Predicted additive effect", is calculated by adding the decreases in blood pressure values obtained after administration of each compound separately); the vehicle (7.5% gelatin aqeuous solution) treatment had no effect on MAP or HR and the results obtained are therefore not represented in the figure. In brief, co-administration of ACT-132577 and valsartan decreased MAP beyond the predicted (calculated) values, demonstrating synergism between the two molecules. In contrast to MAP, HR was not affected in any of the treatment groups.

Example E: Acute Effects of ACT-132577, Alone or in Combination with Valsartan, in Deoxycorticosterone Acetate Salt Rats The acute effects of ACT-132577 administered orally at a single dose of 10 mg/kg on blood pressure, in particular on mean arterial blood pressure (hereafter "MAP"), and heart rate (hereafter "HR"), with ACT-132577 being used either alone or in combination with valsartan administered orally at a single dose of 30 mg/kg, can be evaluated by means of telemetry in conscious, male hypertensive deoxycorticosterone acetate salt rats (hereafter "DOCA-salt rats"—see details about this model in Gavras et al., Circ. Res. (1975), 36, 300-309).

In the DOCA-salt rats, hypertension is induced by the combination of unilateral nephrectomy, implantation of pellets of the mineralocorticoid analog DOCA, and provision of 1% sodium chloride in drinking water. 7-8 DOCA-salt rats per treatment group are used for this test. The results obtained regarding MAP are summarised in FIG. 7 wherein each data point is presented as a 6-hour mean (NB: the expected additive effect of the combination of the two drugs, referred to as "Predicted additive effect", is calculated by adding the decreases in blood pressure values obtained after administration of each compound separately); the vehicle (4% gelatin aqeuous solution) treatment had no effect on MAP or HR and the results obtained are therefore not represented in the figure. In brief, co-administration of ACT-132577 and valsartan decreased MAP beyond the predicted (calculated) values, demonstrating synergism between the two molecules. In contrast to MAP, HR was not affected in any of the treatment groups.

Example F: Acute Effects of ACT-132577, Alone or in Combination with Enalapril, in Spontaneaously Hypertensive Rats The acute effects of ACT-132577 administered orally at a single dose of 100 mg/kg on blood pressure, in particular on mean arterial blood pressure (hereafter "MAP"), and heart rate (hereafter "HR"), with ACT-132577 being used either alone or in combination with enalapril administered orally at a single dose of 3 mg/kg, can be evaluated by means of telemetry in conscious, male spontaneaously hypertensive rats (hereafter "SHRs"—see details about this model in Atanur et al., Genome Res. (2010), 20, 791-803).

7 SHRs per treatment group are used for this test. The results obtained regarding MAP are summarised in FIG. 8 wherein each data point is presented as a 6-hour mean (NB: the expected additive effect of the combination of the two drugs, referred to as "Predicted additive effect", is calculated by adding the decreases in blood pressure values obtained after administration of each compound separately); the vehicle (4% gelatin aqeuous solution) treatment had no effect on MAP or HR and the results obtained are therefore not represented in the figure. In brief, co-administration of ACT-132577 and enalapril decreased MAP beyond the predicted (calculated) values, demonstrating synergism between the two molecules. In contrast to MAP, HR was not affected in any of the treatment groups.

Example G: Acute Effects of ACT-132577, Alone or in Combination with Amlodipine, in Deoxycorticosterone Acetate Salt Rats The acute effects of ACT-132577 administered orally at a single dose of 10 mg/kg on blood pressure, in particular on mean arterial blood pressure (hereafter "MAP"), and heart rate (hereafter "HR"), with ACT-132577 being used either alone or in combination with amlodipine administered orally at a single dose of 1 mg/kg, can be evaluated by means of telemetry in conscious, male hypertensive deoxycorticosterone acetate salt rats (hereafter "DOCA-salt rats"—see details about this model in Gavras et al., Circ. Res. (1975), 36, 300-309).

In the DOCA-salt rats, hypertension is induced by the combination of unilateral nephrectomy, implantation of pellets of the mineralocorticoid analog DOCA, and provision of 1% sodium chloride in drinking water. 6-8 DOCA-salt rats per treatment group are used for this test. The results obtained regarding MAP are summarised in FIG. 9 wherein each data point is presented as a 6-hour mean (NB: the expected additive effect of the combination of the two drugs, referred to as "Predicted additive effect", is calculated by adding the decreases in blood pressure values obtained after administration of each compound separately); the vehicle (4% gelatin aqueous solution) treatment had no effect on MAP or HR and the results obtained are therefore not represented in the figure. In brief, co-administration of ACT-132577 and amlodipine decreased MAP beyond the predicted (calculated) values, demonstrating synergism between the two molecules. In contrast to MAP, HR was not affected in any of the treatment groups.

Example H: Chronic Effects of ACT-132577 in Deoxycorticosterone Acetate Salt Rats The chronic effects of repeated administrations of doses of 1, 10 and 100 mg/kg/day of ACT-132577, in particular mean arterial blood pressure (hereafter "MAP"), and heart rate (hereafter "HR"), can be evaluated in conscious, male hypertensive deoxycorticosterone acetate salt rats (hereafter "DOCA-salt rats"—see details about this model in Gavras et al., Circ. Res. (1975), 36, 300-309). In the DOCA-salt rats, hypertension is induced by the combination of unilateral nephrectomy, implantation of pellets of the mineralocorticoid analog DOCA, and provision of 1% sodium chloride in drinking water. The results of the DOCA-salt rats treated with ACT-132577 can be compared to those obtained for Wistar rats or for DOCA-salt rats that received only the vehicle (4% gelatin aqueous solution).

a) The results obtained regarding MAP are summarised in FIG. 10 wherein each data point is presented as a 24-hour mean. 6 rats were used for each of the 5 test groups (Wistar control rats (bottom line in FIG. 10), DOCA-salt control rats (top line in FIG. 10) and DOCA-salt rats receiving repeated administrations of doses of 1, 10 and 100 mg/kg/day of ACT-132577 (second to third line from top, respectively, in FIG. 10)). In brief, oral administration of ACT-132577 for 4 weeks dose-dependently attenuated the DOCA-salt-induced increase in MAP without changing HR.

b) The results obtained regarding renal vascular resistance are summarised in FIG. 11 wherein:
  DOCA Ø 2w represents DOCA-salt rats sacrificed just before initiation of treatment with ACT-132577; and
  the "*" symbol in represents a statistical significance factor $p<0.05$ when using a one way ANOVA followed by a Newmal-Keuls multiple comparisons post-hoc test.

In summary, based on these tests, chronic oral administration of ACT-132577 to DOCA-salt rats dose-dependently increased renal blood flow and decreased renal vascular resistance. ACT-132577 also tended to decrease left ventricular hypertrophy, as suggested by the dose-dependent decrease in plasma concentrations of N-terminal pro-brain natriuretic peptide (NTproBNP).

Example I: Effects of ACT-132577, Alone or in Combination with an ACE Inhibitor or an ARB, in Animal Models of Diabetes The effects of ACT-132577 can be assessed in diabetic rodent models (in this regard, see the models described in the following references: Sen et al, *Life Sci.* (2012), 91(13-14), 658-668; Janiak et al., *Eur. J. Pharmacol.* (2006), 534, 271-279; and Iglarz et al, *J. Pharmacol. Exp. Ther.* (2008), 327(3), 736-745). In particular, the effect of ACT-132577, alone or in combination, on glucose tolerance, insulinemia and end organ damage can be investigated. End organ damage includes: vascular function, renal function (e.g. proteinuria), cardiac function and remodelling and any other target organ affected by diabetes (e.g. the eye).

Example J: Evaluation of the Effect of ACT-132577 on Fluid Retention

A decrease in haematocrit (Hct) or haemoglobin occurs secondary to an increase in plasma volume and can be used as a marker of fluid retention. A single oral dose of ACT 132577 (1-30 mg/kg) or vehicle (gelatin) is administered by gavage to male Wistar rats. Twenty-four hours after administration, sublingual blood was sampled under isoflurane-induced anesthesia. Haematocrit is measured using a hematology analyser. ACT-132577 did not impact on haematocrit (Hct) in this assay, suggesting low liability on fluid retention (FIG. 12).

Example K: Hematocrit Measurements, Effects of an SGLT-2 Inhibitor, Alone or in Combination with ACT-132577

Eight- to 12-week-old Male Wistar rats [healthy or diseased (streptozotocyn diabetic rats), or under diuretic treatment (loop diuretic, e.g. furosemide)] are assigned to groups (n=12) in a stratified random manner according to their body weight and baseline Hematocrit (Hct). SGLT-2 inhibitor (e.g. canagliflozin) is administered orally daily at a dose of 30 mg/kg (for canagliflozin) for one week. Then the combination of the same dose of SGLT-2 inhibitor and ACT-132577 (1 to 30 mg/kg) or vehicle (gelatin), n=6/group, is administered by gavage. Sublingual blood is sampled twice a week under isoflurane-induced anesthesia (Attane™, MIN RAD INC. Buffalo, N.Y.). Hematocrit (Hct), hemoglobin (Hb) and erythrocyte indices are measured using a hematology analyzer (Coulter AcT, Beckman Coulter, Nyon, Switzerland and Advia 2120i, Siemens Healthcare Diagnostics GmBH, Zurich, Switzerland).

Example L: Blood Pressure Measurements, Effects of an SGLT-2 Inhibitor, Alone or in Combination with ACT-132577

Spontaneously hypertensive rats (SHR) are instrumented micro-surgically with a telemetry pressure transmitter implanted in the peritoneal cavity (Data Science International, Minnesota, USA) under isoflurane-induced narcosis. In brief, the pressure catheter is inserted into the aorta, below the renal artery pointing upstream. The abdomen is closed and the transmitter sutured to the abdominal musculature. Blood pressure is collected continuously using the Dataquest ART Platinum acquisition system (version 4.36). Drugs (ACT-132577 or SGLT2 inhibitors) or vehicle are administered by gavage (n=4-7 per group) alone or in combination. Systolic, mean and diastolic arterial pressures, and heart rate are collected at 5-minute intervals until the blood pressure curve comes back to baseline.

Results: Maximal effects on MAP are summarized on FIGS. 13 and 14. Because it takes several days for the SGLT2 inhibitors to exert an effect on blood pressure, rats are treated first for 12 days with either vehicle (5 ml/kg/day), or canagliflozin (30 mg/kg/day) or empagliflozin (30 mg/kg/day), then ACT-132577 (30 mg/kg/day) is co-administered for 3 additional days. Canagliflozin and empagliflozin decreased MAP by −9±1 and −13±3 mmHg, respectively. Data demonstrate that ACT-132577, when administered on top of canagliflozin or empagliflozin, further decreased blood pressure by −14±1 and −18±3 mmHg, respectively. These decreases in blood pressure were similar to those obtained when ACT-132577 was administered on top of vehicle without canagliflozin or empagliflozin (−16±2 and −14±2 mmHg respectively).

In summary, based on these results, ACT-132577 at least maintained its hemodynamic efficacy when combined with two different SGLT2 inhibitors in a model of hypertension associated with insulinoresistance.

Example M: Isolated Kidney Preparation, Effects of an SGLT-2 Inhibitor, Alone or in Combination with ACT-132577

Kidneys from healthy or diabetic rats are removed and mounted in a perfusion system to monitor renal pressures. Male Wistar rats are euthanized, the lower abdomen is exposed and surrounding fatty tissue excised around the left kidney and major vessels (aorta, vena cava, renal artery and vein). The kidney and associated vessels are removed en bloc, and the renal vein and then renal artery are cannulated using inox cannulae (O.D. 1 mm, I.D. 0.7 mm, Hugo Sachs) and secured with silk suture. The cannulated kidney is then connected to the perfusion system equipped with pressure sensors (perfused kidney apparatus size 2, Hugo Sachs, Germany). The perfusion buffer is a modified Krebs-Henseleit buffer. The initial perfusion flow rate is 2 ml/minute which is then increased incrementally to 5 ml/minute. Experimental protocols are performed when the perfusion pressure has stabilized at 15-25 mm Hg. Drugs (SGLT2 inhibitor, ACT-132577, their combination) are administered to the perfusion buffer via the perfusion reservoir (200 ml volume) and pressure is recorded continuously.

Example N: Acute Effects of EXFORGE HCT® Alone, and EXFORGE HCT® in Combination with ACT-132577 or Spironolactone, in Spontaneaously Hypertensive Rats The acute effects of Exforge HCT® (i.e. a fixed dose combination of valsartan/amlodipine/hydrochlorothiazide; dosage adapted for 1.6 mg/kg/0.1 mg/kg/0.25 mg/kg for valsartan/amlodipine/hydrochlorothiazide, respectively) on blood pressure, in particular on mean arterial blood pressure (hereafter "MAP"), and heart rate (hereafter "HR") in combination with ACT-132577 or spironolactone can be evaluated by means of telemetry in conscious, male spontaneaously hypertensive rats (hereafter "SHRs"—see details about this model in Atanur et al., *Genome Res.* (2010), 20, 791-803).

9 SHRs per treatment group are used for this test. To match the maximal effect on blood pressure of co-administereds drug in this model, aprocitentan 100 mg/kg is administrated orally on the 3$^{rd}$ day following 3-day oral administration of Exforge HCT® mg/kg and spironolactone 300 mg/kg is co-administered orally with Exforge HCT® on the 1$^{st}$ day followed by 2 days of Exforge HCT® administration. The results obtained regarding MAP are summarised in FIGS. 15 and 16 wherein each data point is presented as a 6-hour mean.

When added on top of Exforge HCT®, aprocitentan or spironolactone further reduced blood pressure. However, aprocitentan induced a greater blood pressure reduction than spironolactone. In contrast to MAP, HR was not affected in any of the treatment groups.

Example O: Acute Effects of EXFORGE HCT® Alone, and EXFORGE HCT® in Combination with ACT-132577 or Spironolactone, in Deoxycorticosterone Acetate Salt Rats The acute effects of Exforge HCT® (dosage adapted for 3.2 mg/kg/0.2 mg/kg/0.5 mg/kg for valsartan/amlodipine/hydrochlorothiazide, respectively) on blood pressure, in particular on mean arterial blood pressure (hereafter "MAP"), and heart rate (hereafter "HR") in combination with ACT-132577 (10 mg/kg) or spironolactone (300 mg/kg), each administered orally as single doses, can be evaluated by means of telemetry in conscious, male hypertensive deoxycorticosterone acetate salt rats (hereafter "DOCA-salt rats"—see details about this model in Gavras et al., *Circ. Res.* (1975), 36, 300-309).

In the DOCA-salt rats, hypertension is induced by the combination of unilateral nephrectomy, implantation of pellets of the mineralocorticoid analog DOCA, and provision of 1% sodium chloride in drinking water. 7-9 DOCA-salt rats per treatment group are used for this test. The results obtained regarding MAP are summarised in FIGS. 17 and 18 wherein each data point is presented as a 6-hour mean.

When added on top of Exforge HCT®, aprocitentan 10 mg/kg or spironolactone 300 mg/kg further reduced blood pressure. However, aprocitentan induced a greater blood pressure reduction than spironolactone. In contrast to MAP, HR was not affected in any of the treatment groups.

Example P: Effects of ACT-132577, Alone or in Combination with a SGLT2 Inhibitor, in an Animal Model of Diabetic Kidney Disease The effects of ACT-132577, alone or in combination with a SGLT2 inhibitor, can be assessed in an animal model of diabetic kidney disease such as the ZDF-1 rat (Su et al. Am J Nephrol. 2016 November; 44(5): 339-353), a diabetic rodent model with renal impairment. In particular, the effect of ACT-132577, alone or in combination with a SGLT2 inhibitor, on blood pressure, glycemia and blood HBA1c, insulinemia and renal damage can be investigated. Renal damage includes: proteinuria, measurement of glomerular filtration rate via metabolic cages, biomarkers (e.g. Kim-1), urinary and plasma ketone bodies and creatinine, terminal hispothological examination of the kidney (glomerular damage, vasculopathy, fibrosis).

The invention claimed is:

1. A pharmaceutical composition containing, as active principles, aprocitentan, or a pharmaceutically acceptable salt thereof, in combination with an SGLT-2 inhibitor, which is atigliflozin, bexagliflozin, canagliflozin, dapagliflozin, empagliflozin, ertugliflozin, henagliflozin, ipragliflozin, luseogliflozin, remogliflozin, sotagliflozin, or tofogliflozin, or a pharmaceutically acceptable salt thereof, as well as at least one pharmaceutically acceptable excipient;
   wherein said composition comprises aprocitentan in crystalline form, wherein said crystalline form is characterized by the presence of peaks in the X-ray powder diffraction diagram at the following angles of refraction 2θ: 17.8°, 18.6°, 20.0°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°.

2. A pharmaceutical composition according to claim 1, wherein the SGLT-2 inhibitor, or a pharmaceutically acceptable salt thereof, is canagliflozin, dapagliflozin, or empagliflozin, or a pharmaceutically acceptable salt thereof.

3. A pharmaceutical composition according to claim 1, wherein the SGLT-2 inhibitor, or a pharmaceutically acceptable salt thereof, is canagliflozin, or a pharmaceutically acceptable salt thereof.

4. A pharmaceutical composition according to claim 1 wherein aprocitentan, or a pharmaceutically acceptable salt thereof, is comprised in a pharmaceutical unit dosage form suitable for the oral administration of 10 to 50 mg per day of aprocitentan, wherein aprocitentan is comprised in said pharmaceutical unit dosage form in crystalline form, wherein said crystalline form is characterized by the presence of peaks in the X-ray powder diffraction diagram at the following angles of refraction 2θ: 17.8°, 18.6°, 20.0°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°.

5. A pharmaceutical composition according to claim 3, wherein
   aprocitentan, or a pharmaceutically acceptable salt thereof, is comprised in a pharmaceutical unit dosage form suitable for the oral administration of 10 to 50 mg per day of aprocitentan, wherein aprocitentan is comprised in said pharmaceutical unit dosage form in crystalline form, wherein said crystalline form is characterized by the presence of peaks in the X-ray powder diffraction diagram at the following angles of refraction 2θ: 17.8°, 18.6°, 20.0°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°; and canagliflozin, or a pharmaceutically acceptable salt thereof, is comprised in a pharmaceutical unit dosage form suitable for the oral administration of 50 to 400 mg per day of canagliflozin.

6. A pharmaceutical composition according to claim 1, wherein the SGLT-2 inhibitor, or a pharmaceutically acceptable salt thereof, is dapagliflozin, or a pharmaceutically acceptable salt thereof.

7. A pharmaceutical composition according to claim 6, wherein aprocitentan, or a pharmaceutically acceptable salt thereof, is comprised in a pharmaceutical unit dosage form suitable for the oral administration of 10 to 50 mg per day of aprocitentan, wherein aprocitentan is comprised in said pharmaceutical unit dosage form in crystalline form, wherein said crystalline form is characterized by the presence of peaks in the X-ray powder diffraction diagram at the following angles of refraction 2θ: 17.8°, 18.6°, 20.0°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°; and dapagliflozin, or a pharmaceutically acceptable salt thereof, is comprised in a pharmaceutical unit dosage form suitable for the oral administration of 1 to 20 mg per day of dapagliflozin.

8. A pharmaceutical composition according to claim 1, wherein the SGLT-2 inhibitor, or a pharmaceutically acceptable salt thereof, is empagliflozin, or a pharmaceutically acceptable salt thereof.

9. A pharmaceutical composition according to claim 8, wherein aprocitentan, or a pharmaceutically acceptable salt thereof, is comprised in a pharmaceutical unit dosage form suitable for the oral administration of 10 to 50 mg per day of aprocitentan, wherein aprocitentan is comprised in said pharmaceutical unit dosage form in crystalline form, wherein said crystalline form is characterized by the presence of peaks in the X-ray powder diffraction diagram at the following angles of refraction 2θ: 17.8°, 18.6°, 20.0°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°; and empagliflozin, or a pharmaceutically acceptable salt thereof, is comprised in a pharmaceutical unit dosage form suitable for the oral administration of 5 to 50 mg per day of empagliflozin.

10. A pharmaceutical composition according to claim 1, wherein the SGLT-2 inhibitor, or a pharmaceutically acceptable salt thereof, is ertugliflozin, or a pharmaceutically acceptable salt thereof.

11. A pharmaceutical composition according to claim 10, wherein aprocitentan, or a pharmaceutically acceptable salt thereof, is comprised in a pharmaceutical unit dosage form suitable for the oral administration of 10 to 50 mg per day of aprocitentan, wherein aprocitentan is comprised in said pharmaceutical unit dosage form in crystalline form, wherein said crystalline form is characterized by the presence of peaks in the X-ray powder diffraction diagram at the following angles of refraction 2θ: 17.8°, 18.6°, 20.0°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°; and ertugliflozin, or a pharmaceutically acceptable salt thereof, is comprised in a pharmaceutical unit dosage form suitable for the oral administration of 2.5 to 50 mg per day of ertugliflozin.

12. A pharmaceutical composition according to claim 1, wherein said aprocitentan in crystalline form is characterized by the presence of peaks in the X-ray powder diffraction diagram at the following angles of refraction 2θ: 9.8°, 9.9°, 11.7°, 17.8°, 18.6°, 20.0°, 21.5°, 22.8°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°.

13. A pharmaceutical composition according to claim 3, wherein said aprocitentan in crystalline form is characterized by the presence of peaks in the X-ray powder diffraction diagram at the following angles of refraction 2θ: 9.8°, 9.9°, 11.7°, 17.8°, 18.6°, 20.0°, 21.5°, 22.8°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°.

14. A pharmaceutical composition according to claim 4, wherein said aprocitentan in crystalline form is characterized by the presence of peaks in the X-ray powder diffraction diagram at the following angles of refraction 2θ: 9.8°, 9.9°, 11.7°, 17.8°, 18.6°, 20.0°, 21.5°, 22.8°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°.

15. A pharmaceutical composition according to claim 5, wherein said aprocitentan in crystalline form is characterized by the presence of peaks in the X-ray powder diffraction diagram at the following angles of refraction 2θ: 9.8°, 9.9°, 11.7°, 17.8°, 18.6°, 20.0°, 21.5°, 22.8°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°.

16. A pharmaceutical composition according to claim 6, wherein said aprocitentan in crystalline form is characterized by the presence of peaks in the X-ray powder diffraction diagram at the following angles of refraction 2θ: 9.8°, 9.9°, 11.7°, 17.8°, 18.6°, 20.0°, 21.5°, 22.8°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°.

17. A pharmaceutical composition according to claim 7, wherein said aprocitentan in crystalline form is characterized by the presence of peaks in the X-ray powder diffraction diagram at the following angles of refraction 2θ: 9.8°, 9.9°, 11.7°, 17.8°, 18.6°, 20.0°, 21.5°, 22.8°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°.

18. A pharmaceutical composition according to claim 8, wherein said aprocitentan in crystalline form is characterized by the presence of peaks in the X-ray powder diffraction diagram at the following angles of refraction 2θ: 9.8°, 9.9°, 11.7°, 17.8°, 18.6°, 20.0°, 21.5°, 22.8°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°.

19. A pharmaceutical composition according to claim 9, wherein said aprocitentan in crystalline form is characterized by the presence of peaks in the X-ray powder diffraction diagram at the following angles of refraction 2θ: 9.8°, 9.9°, 11.7°, 17.8°, 18.6°, 20.0°, 21.5°, 22.8°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°.

20. A pharmaceutical composition according to claim 10, wherein said aprocitentan in crystalline form is characterized by the presence of peaks in the X-ray powder diffraction diagram at the following angles of refraction 2θ: 9.8°, 9.9°, 11.7°, 17.8°, 18.6°, 20.0°, 21.5°, 22.8°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°.

21. A pharmaceutical composition according to claim 11, wherein said aprocitentan in crystalline form is characterized by the presence of peaks in the X-ray powder diffraction diagram at the following angles of refraction 2θ: 9.8°, 9.9°, 11.7°, 17.8°, 18.6°, 20.0°, 21.5°, 22.8°, 23.2° and 23.5°; wherein said X-ray powder diffraction diagram is obtained by using combined Cu Kα1 and Kα2 radiation, without Kα2 stripping; and the accuracy of the 2θ values is in the range of 2θ+/−0.2°.

22. A pharmaceutical composition according to claim 1, wherein said aprocitentan in crystalline form essentially shows the X-ray powder diffraction pattern as depicted in FIG. 1, wherein said X-ray powder diffraction diagram is obtained by using combined Cu Kα1 and Kα2 radiation, without Kα2 stripping; and the accuracy of the 2θ values is in the range of 2θ+/−0.2°.

23. A pharmaceutical composition according to claim 3, wherein said aprocitentan in crystalline form essentially shows the X-ray powder diffraction pattern as depicted in FIG. 1, wherein said X-ray powder diffraction diagram is obtained by using combined Cu Kα1 and Kα2 radiation, without Kα2 stripping; and the accuracy of the 2θ values is in the range of 2θ+/−0.2°.

24. A pharmaceutical composition according to claim 4, wherein said aprocitentan in crystalline form essentially shows the X-ray powder diffraction pattern as depicted in FIG. 1, wherein said X-ray powder diffraction diagram is obtained by using combined Cu Kα1 and Kα2 radiation, without Kα2 stripping; and the accuracy of the 2θ values is in the range of 2θ+/−0.2°.

25. A pharmaceutical composition according to claim 5, wherein said aprocitentan in crystalline form essentially shows the X-ray powder diffraction pattern as depicted in FIG. 1, wherein said X-ray powder diffraction diagram is obtained by using combined Cu Kα1 and Kα2 radiation, without Kα2 stripping; and the accuracy of the 2θ values is in the range of 2θ+/−0.2°.

26. A pharmaceutical composition according to claim 6, wherein said aprocitentan in crystalline form essentially shows the X-ray powder diffraction pattern as depicted in FIG. 1, wherein said X-ray powder diffraction diagram is obtained by using combined Cu Kα1 and Kα2 radiation, without Kα2 stripping; and the accuracy of the 2θ values is in the range of 2θ+/−0.2°.

27. A pharmaceutical composition according to claim 7, wherein said aprocitentan in crystalline form essentially shows the X-ray powder diffraction pattern as depicted in FIG. 1, wherein said X-ray powder diffraction diagram is obtained by using combined Cu Kα1 and Kα2 radiation, without Kα2 stripping; and the accuracy of the 2θ values is in the range of 2θ+/−0.2°.

28. A pharmaceutical composition according to claim 8, wherein said aprocitentan in crystalline form essentially shows the X-ray powder diffraction pattern as depicted in FIG. 1, wherein said X-ray powder diffraction diagram is obtained by using combined Cu Kα1 and Kα2 radiation, without Kα2 stripping; and the accuracy of the 2θ values is in the range of 2θ+/−0.2°.

29. A pharmaceutical composition according to claim 9, wherein said aprocitentan in crystalline form essentially shows the X-ray powder diffraction pattern as depicted in FIG. 1, wherein said X-ray powder diffraction diagram is obtained by using combined Cu Kα1 and Kα2 radiation, without Kα2 stripping; and the accuracy of the 2θ values is in the range of 2θ+/−0.2°.

30. A pharmaceutical composition according to claim 10, wherein said aprocitentan in crystalline form essentially shows the X-ray powder diffraction pattern as depicted in FIG. 1, wherein said X-ray powder diffraction diagram is obtained by using combined Cu Kα1 and Kα2 radiation, without Kα2 stripping; and the accuracy of the 2θ values is in the range of 2θ+/−0.2°.

31. A pharmaceutical composition according to claim 11, wherein said aprocitentan in crystalline form essentially shows the X-ray powder diffraction pattern as depicted in FIG. 1, wherein said X-ray powder diffraction diagram is obtained by using combined Cu Kα1 and Kα2 radiation, without Kα2 stripping; and the accuracy of the 2θ values is in the range of 2θ+/−0.2°.

* * * * *